US006953783B1

(12) United States Patent
Besterman et al.

(10) Patent No.: US 6,953,783 B1
(45) Date of Patent: Oct. 11, 2005

(54) MODULATION OF GENE EXPRESSION BY COMBINATION THERAPY

(75) Inventors: Jeffrey M. Besterman, Baie D'Urfe (CA); Robert A. Macleod, Westmount (CA); William M. Siders, Watertown, MA (US); Zuomei Li, Kirkland (CA)

(73) Assignee: MethylGene, Inc., St. Laurent (CA)

( * ) Notice: Subject to any disclaimer, the term of this patent is extended or adjusted under 35 U.S.C. 154(b) by 0 days.

(21) Appl. No.: 09/420,692

(22) Filed: Oct. 19, 1999

Related U.S. Application Data
(60) Provisional application No. 60/104,804, filed on Oct. 19, 1998.

(51) Int. Cl.[7] ......................... A01N 43/04; C12Q 1/68; C12P 19/34; C12N 5/00; C07H 21/02
(52) U.S. Cl. ........................ 514/44; 435/6; 435/91.1; 435/455; 435/375; 536/23.1; 536/24.5
(58) Field of Search ................... 435/6, 91.1, 91.31, 435/455, 458, 375, 325; 536/23.1, 24.5, 24.3, 24.31, 24.33; 514/44

(56) References Cited

U.S. PATENT DOCUMENTS 5,578,716 A * 11/1996 Szyf et al.
6,268,137 B1 * 7/2001 Szyf et al. ..................... 435/6

FOREIGN PATENT DOCUMENTS

| WO | WO 94 08625 A | 4/1994 |
| WO | WO94/08625 | 4/1994 |
| WO | WO97/32589 | 9/1997 |
| WO | WO 97 32589 A | 9/1997 |
| WO | WO 97 32604 A | 9/1997 |
| WO | WO97/32604 | 9/1997 |
| WO | WO 97 35990 A | 10/1997 |
| WO | WO97/44346 | 11/1997 |
| WO | WO 97/44346 * | 11/1997 |
| WO | WO 99 15648 A | 4/1999 |

OTHER PUBLICATIONS

Fournel et al. Journal of Biological Chemistry. August 20, 1999, vol. 274, No. 34, pp. 24250–24256.*
Branch, A. D. A good antisense molecule is hard to find. Feb. 1998. TIBS vol. 23, pp. 45–50.*
Crooke, S. T. Antisense Research and Application, Chapter 1, Basic Principles of Antisense Therapeutics, (1998) pp. 1–50. Springer-Verlag Press. Berlin. Heidelberg, New York.*
Jen et al. Suppression of Gene Expression by Targeted Disruption of Messenger RNA: Available Options and Current Stategies. (2000) Stem Cells. vol. 18, pp. 307–319.*
Ju et al. "Increased Drug Sensitivity of Tumor Cells by Manipulation of Cell Cycle Control Genes." (Jan. 1996), Thesis, University of Southern California, pp. 100–130.*

Szyf, M., Pharmacol. Ther. vol. 70, No. 1, 1996, "The DNA Methylation Machinery as a Target for Anticancer Therapy", pp. 1–37.
Szyf, M. et al., The Journal of Biological Chemistry, vol. 267, No. 15, 1992, "Induction of Myogenic Differentiation by an Expression Vector Encoding the DNA Methyltransferase cDNA sequence in the Antisense Orientation", pp. 12831–12836.
MacLeod, A. R. et al., The Journal of Biological Chemistry, vol. 270, No. 14, 1995, "Expression of Antisense to DNA Methyltransferase mRNA Induces DNA Demethylation and Inhibits Tumorigenesis", pp. 8037–8043.
Wu, J.C. et al., The Journal of Biological Chemistry, vol. 262, No. 10, 1987, "Kinetic and Catalytic Mechanism of Hhal Methyltransferase", pp. 4778–4786.
Bestor, T. et al., J. Mol. Biol., vol. 203, 1988, "Cloning and Sequencing of a cDNA Encoding DNA Methyltransferase of Mouse Cells: The Carboxyl–terminal Domain of the Mammalian Enzymes is Related to Bacterial Restriction Methyltransferases", pp. 971–983.
Yen, R.W.C. et al., Nucleic Acide Research, vol. 20, No. 9, 1992, "Isolation and characterization of the cDNA encoding human DNA methyltransferase", pp. 2287–2291.
Yoder, J.A. et al., The Journal of Biological Chemistry, vol. 271, No. 49, 1996, "New 5' Regions of the Murine and Human Genes for DNA (Cytosine–5)–methyltransferase", pp. 31092–31097.
Ju et al., "Increased Drug Sensitivity of Tumor Cells by Manipulation of Cell Cycle Control Genes", Thesis University of Southern California, Jan. 1, 1996, pp. 100–130.
PCT International Search Report, International Application No. PCT/US99/24278: Date of Completion: Mar. 22, 2000, Date of Mailing: Mar. 29, 2000. Authorized Officer: Leherte, C. (5 pages).
Ju et al., "Increased Drug Sensitivity of Tumor Cells by manipulation of Cell Cycle Control Genes", Thesis Univ. So. California, pp. 100–130, 1996.
Amer. Assoc. for Cancer Res.: Proceedings of the 89th Annual Meeting of the Am. Assoc. for Cancer Res., New Orleans, 39:416 XP002094749, 1998.

* cited by examiner

Primary Examiner—Karen A. Lacourciere
Assistant Examiner—Jane Zara
(74) Attorney, Agent, or Firm—Keown & Associates

(57) ABSTRACT

The invention relates to the modulation of gene expression. In particular, the invention relates to compositions comprising antisense oligonucleotides which inhibit expression of a gene in operable association with protein effectors of a product of that gene, and methods of using the same.

In addition, the invention relates to the modulation of mammalian gene expression regulated by methylation.

4 Claims, 31 Drawing Sheets

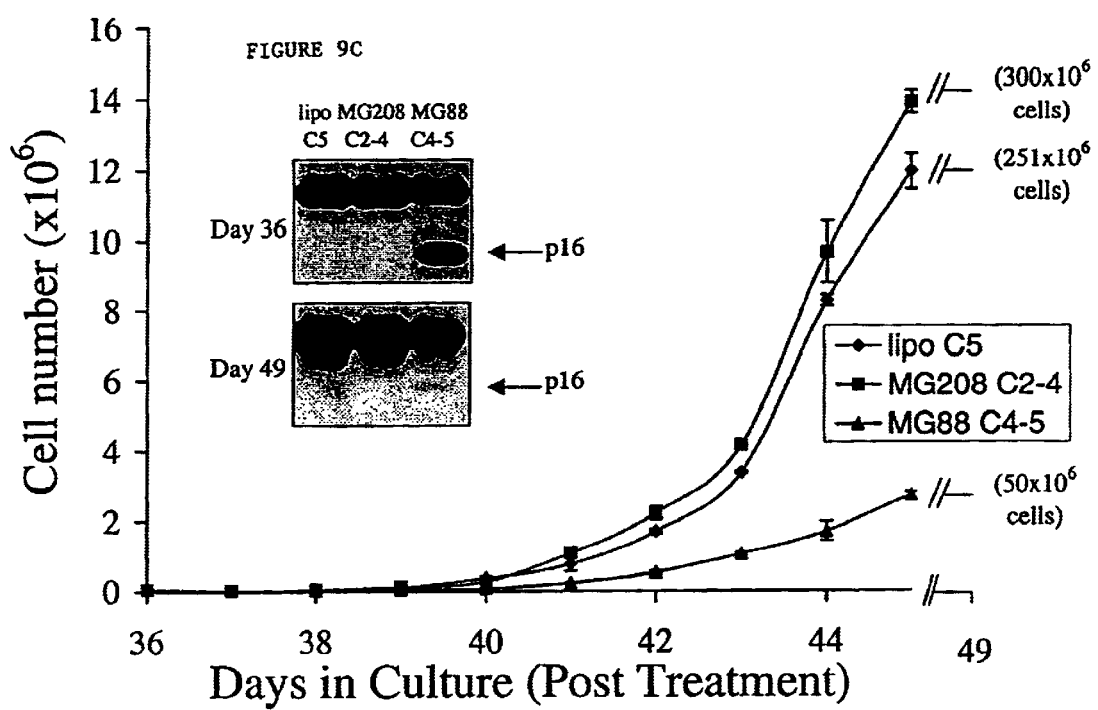

p16 reactivation in T24 cells by 5-aza-deoxycytidine treatment

T24 cells were plated and treated for three days with varying concentrations of 5aza-dC. The p16 protein was immunoprecipitated from cell lysates and a Western analysis was performed.

Synergistic reactivation of p16 in T24 cells by treatment with antisense to DNA methyltransferase (MG88) and 5-aza-deoxycytidine.

T24 cells were plated and transfected with either MG88 or MG208 and treated with varying concentrations of 5-aza-dC every day for three days. The p16 protein was immunoprecipitated from cell lysates and a Western analysis was performed.

Synergistic reactivation of p16 in T24 cells by treatment with antisense to DNA methyltransferase (MG98) and 5-aza-deoxycytidine.

T24 cells were plated and transfected with either MG98 or MG207 and treated with varying concentrations of 5-aza-dC every day for three days. The p16 protein was immunoprecipitated from cell lysates and a Western analysis was performed.

Synergistic reactivation of p16 in T24 cells by treatment with low dose antisense to DNA methyltransferase (MG88) and 5-aza-deoxycytidine.

T24 cells were plated and transfected with either MG88 or MG 208 and treated with varying concentrations of 5-aza-dC every day for three days. The p16 protein was immunoprecipitated from cell lysates and a Western analysis was performed.

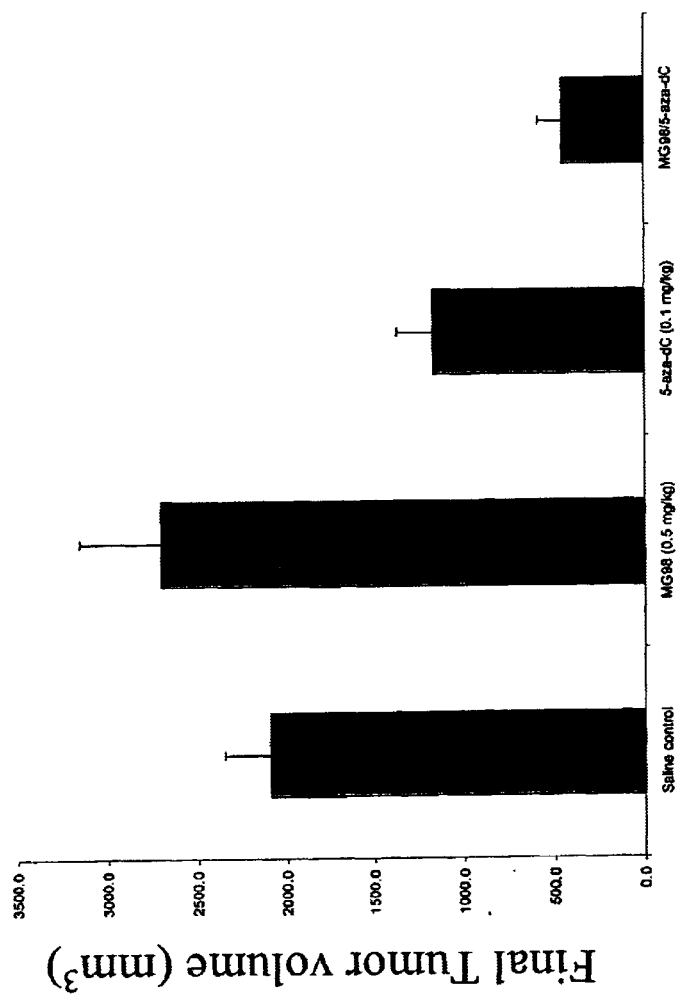

Fig. 7. Antitumor activity of combination of MG98 and 5-aza-2-deoxycytidine. Groups are: Saline control, MG98 (0.5 mg/kg/day), 5-aza-2-deoxycytidine (0.1 mg/kg/day), MG98 (0.5 mg/kg/day) and 5-aza-2-deoxycytidine (0.1 mg/kg/day). Groups consisted of six animals each. Error bars represent SEM. Group MG98/5-aza-dC was statistically different ($p<0.05$) from both saline treated group and from 5-aza-dC treated group. Group MG98 was not significantly different than saline control group.

FIGURE 20B

Schedule Independent Inhibition of Cell Cycle Progression by Combination of DNA MeTase Antisense inhibitor (MG88) and DNA MeTase Small Molecule Inhibitor (5-aza-dC).

Schedule A: DNA MeTase Antisense Inhibitor (MG88) followed by Small Molecule Inhibitor (5-aza-dC)

Schedule B: Small Molecule Inhibitor (5-aza-dC) followed by DNA MeTase Antisense Inhibitor (MG88)

Lipofetcin

Mismatch Control

TS Antisense (25nM)

5-FU (500nM)

5-FU (500nM) + Mismatch (25nM)

5-FU (500nM) + TS Antisense (25nM)

MODULATION OF GENE EXPRESSION BY COMBINATION THERAPY

This application claims benefit of the provisional application 60/104,804, filed Oct. 19, 1998.

BACKGROUND OF THE INVENTION

1. Field of the Invention

This invention relates to the modulation of gene expression, and to the modulation of mammalian gene expression regulated by methylation.

2. Summary of the Related Art

The modulation of expression of genes has long been pursued by researchers. For example, many mammalian diseases are associated with the over- or under-expression of certain genes. By modulating the expression of the gene whose aberrant expression is associated with a disease (or a predisposition to develop such a disease), the disease symptoms may be alleviated.

For example, it would be desirable to modulate the enzyme, DNA Methyltransferase (DNA MeTase), which mediates the methylation of mammalian DNA.

Methylation of mammalian DNA is enzymatically mediated by the covalent modification of the fifth carbon position of the pyrimidine ring of cytosine in CpG dinucleotides. Changes in the pattern of DNA methylation have been correlated with a number of processes in eukaryotes. Holliday (1990) Philos. Trans. R. Soc. Lond. B. Biol. Sci. 326: 329–338 discusses the role of methylation in parental imprinting. Antequera et al. (1989) Cell 58: 509–517 discusses the significance of methylation in developmental regulation. Fedoroff et al. (1989) Cell 56: 181–191 discloses that methylation is involved in transposition. Hare and Taylor (1985) Proc. Natl. Acad. Sci. USA 82: 7350–7354 discloses that methylation is also implicated in DNA repair. In addition, Gartler and Riggs (1983) Ann. Rev. Genet. 17. 155–190 correlates methylation with X chromosome inactivation, while Bird et al. (1986) Nature 321: 209–213 discloses that methylation also plays a pivotal role in chromatin organization.

While several observations have suggested a role for DNA methylation in cancer pathogenesis, there has been a great deal of disagreement as to the mechanisms involved. Szyf et al. (1996) Pharmacol. Ther. 70 (1): 1–37 discloses that methylation and demethylation activities are critical components of some tumorigenic growth forms. MacLeod and Szyf (1995) J. Biol. Chem. 270: 8037–8043 discloses that the level of DNA methyltransferase activity may be a nodal control point over oncogenic growth. On the other hand, others have dismissed the theory that DNA Methyltransferase plays a causal role in oncogenesis.

A significant obstacle to the investigation of the role of methylation lies in the deficiencies of available methods to modulate methylation itself. To date, most studies have relied on 5-aza-C and/or 5aza-dC to inhibit DNA methylation by forming a stable adduct with DNA methyltransferase, thus mimicking the transient covalent intermediate complex believed to be formed during methylation (see, e.g., Wu and Santi (1987) J. Biol. Chem. 262: 4778–4786). This approach, albeit effective in reducing DNA methyltransferase activity and correlating with tumorigenesis inhibition, is therapeutically deficient. Unfortunately, threshold concentrations of 5-azaC or 5-aza-dC empirically necessary to inhibit DNA methyltransferase activity have been found to be toxic to mammals (juttermann et al. (1994) Proc. Natl. Acad. Sci. USA 91: 11797–11801; Laird (1997) Mol. Med. Today 3: 223–229).

More recently, Szyf et al. (1995) J. Biol. Chem. 267: 12831–12836, has disclosed a more promising approach to the modulation of DNA methylation using expression of antisense RNA complementary to the DNA methyltransferase mRNA to study the effect of methylation on cancer cells. U.S. Pat. No. 5,578,716, discloses the use of antisense oligonucleotides complementary to the DNA methyltransferase gene to inhibit gene expression. These developments have provided powerful new tools for probing the role of methylation in numerous cellular processes. In addition, they have provided promising new approaches for developing therapeutic compounds that can modulate methylation levels.

The effect of antisense inhibition is not immediate, due to the half-life of the DNA methyltransferase enzyme. Thus, although the expression of DNA methyltransferase is modulated, residual enzyme can continue to methylate DNA until such enzyme is degraded. Furthermore, polysome-associated DNA methyltransferase mRNA may also persist for some time, allowing additional translation to produce additional enzyme. In addition, the pharmacodynamic properties of oligonucleotides suggest that lower doses than are currently used could be beneficial (Agrawal et al. (1995) Clinical Pharmacokinetics 28: 7–16; Zhang et al. (1995) Clinical Pharmacology and Therapeutics 58: 44–53).

Therefore, there remains a need to develop more effective methods for the modulation of the expression of genes, such as DNA methyltransferase, that would reduce the required dosage of antisense oligonucleotides, specific inhibitors of gene products, or other agents currently used while at the same time effectively accomplish the inhibition of gene expression.

SUMMARY OF THE INVENTION

The present inventors have devised a combination approach by which a gene, such as mammalian DNA methyltransferase (DNA MeTase), is inhibited at the genetic level as well as at the protein level. Surprisingly, this combination approach has been found to reduce the required dosage for efficacy of both antisense oligonucleotides against the gene as well as small molecule inhibitors of the gene product.

The invention also provides improved methods and compositions for the modulation of mammalian DNA MeTase at the genetic level as well as at the protein level and the modulation of mammalian gene expression regulated by methylation. The methods and compositions according to the invention are useful as analytical tools for transgenic studies and as therapeutic tools.

In a first aspect the invention provides a method for inhibiting the expression of a gene in a cell comprising contacting the cell with an effective synergistic amount of an antisense oligonucleotide which inhibits expression of the gene, and an effective synergistic amount of a protein effector of a product of the gene.

In embodiments of the first aspect of the invention, the cell is contacted with an effective synergistic amount of at least one antisense oligonucleotide for an effective period of time. In certain embodiments, the cell is contacted with an effective synergistic amount of at least one protein effector for an effective period of time. In certain embodiments, each of the antisense oligonucleotide and the protein effector is admixed with a pharmaceutically acceptable carrier medium prior to contacting the cell. In certain embodiments, the antisense oligonucleotide and the protein effector are mixed prior to contacting the cell.

In certain preferred embodiments of the first aspect of the invention, the cell is contacted separately with each of the antisense oligonucleotide and the protein effector. In certain embodiments, the cell is contacted with the antisense oligonucleotide prior to being contacted with the protein effector. In certain embodiments, the gene encodes a DNA methyltransferase and the cell contacted with the antisense oligonucleotide prior to being contacted with the protein effector is induced to undergo apoptosis or is arrested in the S phase of the cell cycle. In certain embodiments, the cell is contacted with the protein effector prior to being contacted with the antisense oligonucleotide. In certain embodiments, the gene encodes a DNA methyltransferase and the cell contacted with the protein effector prior to being contacted with the antisense oligonucleotide is arrested in the $G_1$ phase of the cell cycle.

In certain preferred embodiments of the first aspect of the invention, the gene encodes a DNA methyltransferase and the cell comprises a gene whose expression has been inactivated by methylation. In certain embodiments, expression of the gene whose expression has been inactivated by methylation is reactivated in the contacted cell. In preferred embodiments, the gene whose expression has been inactivated by methylation is the $p16^{ink4}$ tumor suppressor gene.

In a second aspect, the invention provides a method for treating a disease responsive to inhibition of a gene. The method according to this aspect of the invention includes administering to a mammal, including a human, which has at least one cell affected by the disease, a therapeutically effective synergistic amount of an antisense oligonucleotide which inhibits expression of the gene, and a therapeutically effective synergistic amount of a protein effector of a product of the gene.

In embodiments of the second aspect of the invention, the mammal is administered a therapeutically effective synergistic amount of at least one antisense oligonucleotide for a therapeutically effective period of time. In certain embodiments, the mammal is administered a therapeutically effective synergistic amount of at least one protein effector for a therapeutically effective period of time. In certain embodiments, each of the antisense oligonucleotide and the protein effector is admixed with a pharmaceutically acceptable carrier medium prior to administration to the mammal. In certain embodiments, the antisense oligonucleotide and the protein effector are mixed prior to administration to the mammal.

In certain preferred embodiments of the second aspect of the invention, the the antisense oligonucleotide and the protein effector are separately administered to the mammal. In certain embodiments, the antisense oligonucleotide is administered to the mammal prior to the administration of the protein effector. In certain embodiments, the gene encodes a DNA methyltransferase and the cell affected by the disease in the mammal to which the the antisense oligonucleotide is administered prior to the administration of the protein effector is induced to undergo apoptosis or is arrested in the S phase of the cell cycle. In certain embodiments, the protein effector is administered to the mammal prior to the administration of the antisense oligonucleotide. In certain embodiments, the gene encodes a DNA methyltransferase and the cell affected by the disease in the mammal to which the protein effector is administered prior to the administration of the antisense oligonucleotide is arrested in the $G_1$ phase of the cell cycle.

In certain preferred embodiments of the second aspect of the invention, the gene encodes a DNA methyltransferase and the cell affected by the disease comprises a gene whose expression has been inactivated by methylation. In certain embodiments, expression of the gene whose expression has been inactivated by methylation is reactivated in the cell in the mammal to which has been administered a therapeutically effective synergistic amount of an antisense oligonucleotide and a therapeutically effective synergistic amount of a protein effector. In preferred embodiments, the gene whose expression has been inactivated by methylation is the $p16^{ink4}$ tumor suppressor gene.

In a third aspect, the invention provides a method for inhibiting tumor growth in a mammal. The method according to this aspect of the invention includes administering to a mammal, including a human, which has at least one neoplastic cell present in its body a therapeutically effective synergistic amount of an antisense oligonucleotide which inhibits expression of a gene involved in tumorigenesis, and a therapeutically effective synergistic amount of a protein effector of a product of the gene.

In embodiments of the third aspect of the invention, the mammal is administered a therapeutically effective synergistic amount of more than one antisense oligonucleotide for a therapeutically effective period of time. In certain embodiments, the mammal is administered a therapeutically effective synergistic amount of at least one protein effector for a therapeutically effective period of time. In certain embodiments, each of the antisense oligonucleotide and the protein effector is admixed with a pharmaceutically acceptable carrier medium prior to administration to the mammal. In certain embodiments, the antisense oligonucleotide and the protein effector are mixed prior to administration to the mammal.

In certain preferred embodiments of the third aspect of the invention, the the antisense oligonucleotide and the protein effector are separately administered to the mammal. In certain embodiments, the antisense oligonucleotide is administered to the mammal prior to the administration of the protein effector. In certain embodiments, the gene encodes a DNA methyltransferase and the neoplastic cell in the mammal to which the the antisense oligonucleotide is administered prior to the administration of the protein effector is induced to undergo apoptosis or is arrested in the S phase of the cell cycle. In certain embodiments, the protein effector is administered to the mammal prior to the administration of the antisense oligonucleotide. In certain embodiments, the gene encodes a DNA methyltransferase and the neoplastic cell in the mammal to which the protein effector is administered prior to the administration of the antisense oligonucleotide is arrested in the $G_1$ phase of the cell cycle.

In certain preferred embodiments of the third aspect of the invention, the gene encodes a DNA methyltransferase and the neoplastic cell comprises a gene whose expression has been inactivated by methylation. In certain embodiments, expression of the gene whose expression has been inactivated by methylation is reactivated in the neoplastic cell in the mammal to which has been administered a therapeutically effective synergistic amount of an antisense oligonucleotide and a therapeutically effective synergistic amount of a protein effector. In preferred embodiments, the gene whose expression has been inactivated by methylation is the $p16^{ink4}$ tumor suppressor gene.

In certain embodiments of the first three aspects of the invention, the gene encodes a DNA methyltransferase. In certain embodiments, the protein effector is selected from the group consisting of 5-aza-cytidine, 5-aza-2'- deoxycytidine, 5-fluoro-2'-deoxycytidine and 5,6-dihydro-5-azacytidine. In certain embodiments of the first, second, and third aspects, the gene encodes a histone deacetylase. In certain embodiments, the protein effector is selected form the group consisting of trichostatin A, depudecin, trapoxin, suberoylanilide hydroxamic acid, FR901228, MS-27-275, CI-994, and sodium butyrate. In certain embodiments of the first three aspects, the gene encodes a thymidylate synthase. In certain embodiments, the protein effector is selected form the group consisting of 5-fluorouracil, Tomudex, Raltitrexed, Zeneca ZD1694, Zeneca ZD9331, Thymitaq, AG331, Ly231514, and BW1843U89.

In various embodiments of the first three aspects of the invention, the antisense oligonucleotide is in operable association with a protein effector. In certain embodiments, the antisense oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain embodiments, the antisense oligonucleotide is a chimeric oligonucleotide comprising a phosphorothioate, phosphodiester or phosphorodithioate region and an alkylphosphonate or alkylphosphonothioate region. In certain embodiments, the antisense oligonucleotide comprises a ribonucleotide or 2'-O-substituted ribonucleotide region and a deoxyribonucleotide region.

In a fourth aspect, the invention provides an inhibitor of a gene comprising an antisense oligonucleotide which inhibits expression of the gene in operable association with a protein effector of a product of the gene. In certain embodiments of this aspect of the invention, the antisense oligonucleotide is in operable association with two or more protein effectors.

In certain embodiments of the fourth aspect of the invention, the gene encodes a DNA methyltransferase. In certain embodiments, the protein effector is selected from the group consisting of 5-aza-cytidine, 5-aza-2'-deoxycytidine, 5-fluoro-2'-deoxycytidine and 5,6-dihydro-5-azacytidine. In certain embodiments, the gene encodes a histone deacetylase. In certain embodiments, the protein effector is selected form the group consisting of trichostatin A, depudecin, trapoxin, suberoylanilide hydroxamic acid, FR901228, MS-27-275, CI-994, and sodium butyrate. In certain embodiments, the gene encodes a thymidylate synthase. In certain embodiments, the protein effector is selected form the group consisting of 5-fluorouracil, Tomudex, Raltitrexed, Zeneca ZD1694, Zeneca ZD9331, Thymitaq, AG331, Ly231514, and BW1843U89.

In certain embodiments of the fourth aspect of the invention, the antisense oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain embodiments, the antisense oligonucleotide is a chimeric oligonucleotide comprising a phosphorothioate, phosphodiester or phosphorodithioate region and an alkylphosphonate or alkylphosphonothioate region. In certain embodiments, the antisense oligonucleotide comprises a ribonucleotide or 2'-O-substituted ribonucleotide region and a deoxyribonucleotide region.

In a fifth aspect, the invention provides a pharmaceutical composition comprising an inhibitor of a gene comprising an antisense oligonucleotide which inhibits expression the gene in operable association with a protein effector of a product of the gene. In certain embodiments, the composition further comprises a pharmaceutically acceptable carrier.

In a sixth aspect, the invention provides a method for investigating the role of a gene and/or a product of the gene in cellular growth, including the growth of tumor cells. In the method according to this aspect of the invention, the cell type of interest is contacted with a synergistic amount of an antisense oligonucleotide which inhibits expression the gene and a synergistic amount of a protein effector of a product of the gene, as described for the first aspect according to the invention, resulting in inhibition of expression of the gene in the cell. In certain embodiments, the gene encodes the product selected from the group consisting of a DNA methyltransferase, a histone deacetylase, and a thymidylate synthase. The combinations described herein may be administered at different points in the cell cycle, or in conjunction with promoters or inhibitors of cell growth to determine the role of the gene and/or the product of the gene in the growth of the cell type of interest.

The methods, inhibitors, and compositions of the invention that inhibit expression and/or activity of a gene and/or gene product may be used to treat patients having, or predisposed to developing, a disease responsive to inhibition of the gene. For example, an inhibitor or composition of the invention may administered with a pharmaceutically-acceptable carrier (e.g., physiological sterile saline solution) via any route of administration to patient suffering from a disease responsive to inhibition of a gene in an attempt to alleviate any resulting disease symptoms. For example, an inhibitor or composition of the invention may be used to relieve symptoms of cancer in a patient suffering from cancer, one exemplary, non-limiting disease responsive to inhibition of DNA methyltransferase. Pharmaceutically-acceptable carriers and their formulations are well-known and generally described in, for example, *Remington's Pharmaceutical Sciences* (18th Edition, ed. A. Gennaro, Mack Publishing Co., Easton, Pa., 1990).

BRIEF DESCRIPTION OF THE DRAWINGS

FIG. 9C is a graphic representation showing a growth curve during post-treatment of T24 cell clones following a five day treatment with MG88 (SEQ ID NO:1) (clone4–5, triangles), MG208 (SEQ ID No:4) (clone 2–4, squares), or lipofectin only (done 5, diamonds). The inserted representation of two autoradiographs show the $p16^{ink4}$ protein level in each of the clones of days 36 and 49 post-treatment.

FIG. 20B is a graphic representation showing the inhibition of Colo 205 human colon cancer cell growth (expressed as final tumor volume) by a representative, nonlimiting, synthetic oligonucleotide (MG98) (SEQ ID No:2) and by a representative, nonlimiting DNA MeTase protein effector (5-aza-dC) according to the invention, in a synergistic fashion, resulting in an statistically increased inhibitory effect ($p<0.05$) as compared to that observed using either only oligonucleotide, protein effector, or saline.

DETAILED DESCRIPTION OF THE PREFERRED EMBODIMENTS

Figure 1:
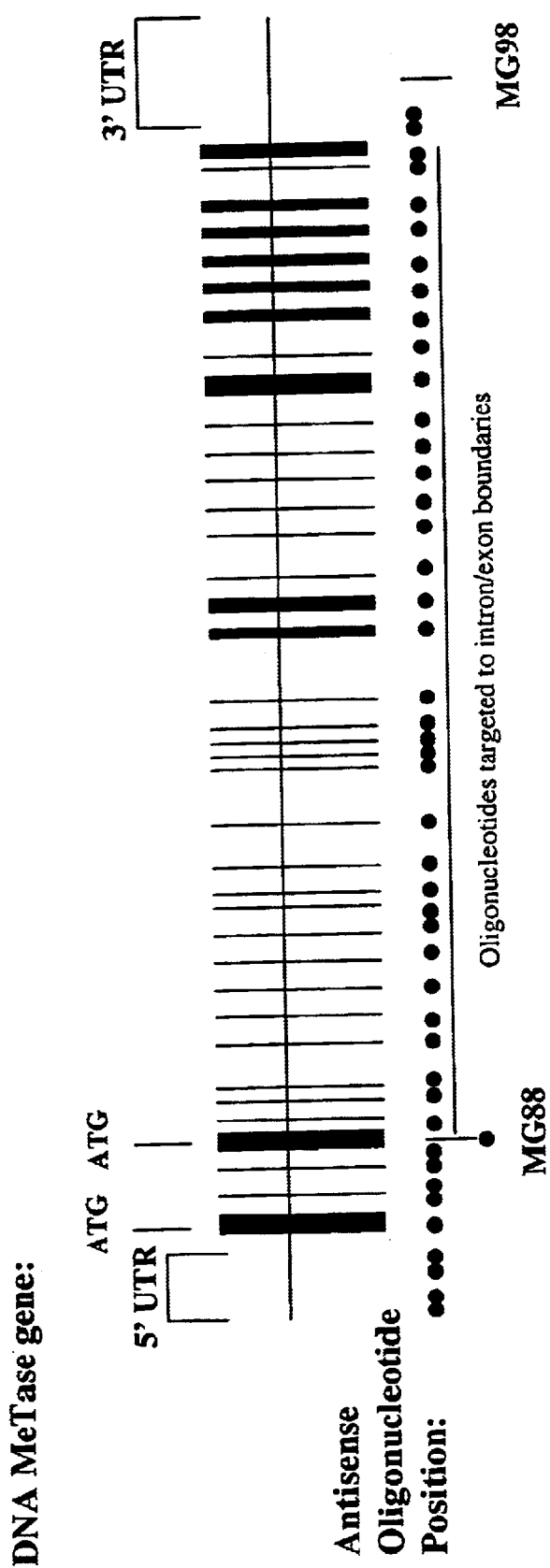
FIG. 1 is a diagrammatic representation of the DNA methyltransferase gene (above) and the positions of the various 20-mer phosphorothioate antisense oligonucleotides (shown as filled circles) on t gene with the positions of two non-limiting synthetic oligonucleotides, MG88 (SEQ ID No:1) and MG98, SEQ ID No:2 highlighted.

The present inventors have devised a combination approach by which expression of a gene is inhibited at the genetic level as well as at the protein level. Surprisingly, this combination approach has been found to reduce the required dosage for efficacy of both antisense oligonucleotides against the gene itself as well as of protein effectors against the product of the gene.

The invention provides improved methods, compounds (e.g., inhibitors such as antisense oligonucleotides and protein effectors) and compositions for the modulation of gene expression at the genetic level as well as at the protein level. In addition, where the gene is DNA methyltransferase (DNA MeTase), the invention provides methods, compounds, and compositions for the modulation of mammalian gene expression regulated by methylation. The methods and compositions according to the invention are useful as analytical tools for transgenic studies and as therapeutic tools, including as gene therapy tools. The invention also provides methods and compositions which may be manipulated and fine tuned to fit the condition(s) to be treated while producing fewer side effects. Standard reference works setting forth the general principles of recombinant DNA technology include Ausubel et al., *Current Protocols in Molecular Biology*, John Wiley & Sons, New York (1994); Sambrook et al., *Molecular Cloning: A Laboratory Manual*, 2d Ed., Cold Spring Harbor Laboratory Press, Plainview, N.Y. (1989); Kaufman et al., Eds., *Handbook of Molecular and Cellular Methods in Biology and Medicine*, CRC Press, Boca Raton (1995); McPherson, Ed., *Directed Mutagenesis: A Practical Approach*, IRL Press, Oxford.(1991). The patents and scientific literature, including accession numbers to GenBank database sequences, referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the later. Likewise, any conflict between an art-understood definition of a word or phrase and a definition of the word or phrase as specifically taught in this specification shall be resolved in favor of the latter.

In a first aspect the invention provides a method for inhibiting the expression of a gene in a cell comprising contacting the cell with an effective synergistic amount of an antisense oligonucleotide which inhibits expression of the gene, and an effective synergistic amount of a protein effector of a product of the gene. In certain embodiments of the first aspect of the invention, the cell is contacted with an effective synergistic amount of at least one antisense oligonucleotide and/or at least one protein effector for an effective period of time.

As used herein for all aspects of the invention, the term "protein effector" denotes an active moiety capable of inhibiting the indicated protein or product of a gene at the protein level. For example, a "DNA MeTase protein effector" or a "protein effector of the product of a DNA MeTase gene" inhibits DNA MeTase at the protein level. By "product of a gene" is meant a protein or polypeptide, regardless of secondary modifications (e.g., glycosylation, lipidation, or phosphorylation), encoded by the gene. The term protein effector therefore includes, without limitation, specific enzyme inhibitors which are capable of inhibiting activity of the indicated protein or product of a gene. A protein effector is a molecule that inhibits the activity of the indicated protein to a greater extent than it inhibits the activity of any unrelated protein. Preferably, a protein effector inhibits the indicated protein at least 5-fold, more preferably at least 10-fold, even more preferably at least 50-fold, and most preferably at least 100-fold more than it inhibits any unrelated protein.

The terms "effective synergistic amount" and "effective period of time" are used to denote known concentrations of the antisense oligonucleotide and of the protein effector and for periods of time effective to achieve the result sought. The effective synergistic amount of the antisense oligonucleotide and/or the effective synergistic amount of the protein effector is/are less than the amount(s) empirically found necessary to inhibit the gene when either the antisense oligonucleotide or the protein effector are used individually. In preferred embodiments, the combined inhibitory effect of the antisense oligonucleotide and the protein effector according to the invention are more than additive, i.e., the combined inhibitory effect is greater than the expected total inhibitory effect calculated on the basis of the sum of the individual inhibitory effects.

The antisense oligonucleotides according to all aspects of the invention are complementary to a region of double-stranded DNA or of RNA (or a region at the intron/exon boundary of DNA or RNA) that encodes the product of the gene. For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/ or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active by quantitating the mRNA encoding a product of the gene, or in a Western blotting analysis assay for the product of the gene, or in an activity assay for an enzymatically active gene product, or in a soft agar growth assay, or in a reporter gene construct assay, or an in vivo tumor growth assay, all of which are described in detail in this specification or in Ramchandani et al. (1997) Proc. Natl. Acad. Sci. USA 24: 684–689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465–496).

In certain embodiments of all aspects of the invention, any of the antisense oligonucleotides may be operably associated with one or more protein effectors. A preferred operable linkage is a hydrolyzable association. Preferably, the hydrolyzable association is a covalent linkage between the antisense oligonucleotide and the protein effector(s). Preferably, such covalent bonding is hydrolyzable by esterases and/or amidases. Examples of such hydrolyzable bonding are shown in PCT publication WO96/07392, which is hereby incorporated by reference. Phosphate esters are particularly preferred.

In certain preferred embodiments, the covalent linkage may be directly between the antisense oligonucleotide and the protein effector so as to integrate the protein effector into the backbone. Alternatively, the covalent linkage may be through an extended structure. Linkages of this type may be formed by covalently linking the antisense oligonucleotide to the protein effector through coupling of both the antisense oligonucleotide and the protein effector to a carrier molecule such as a carbohydrate, a peptide or a lipid or a glycolipid. Other preferred operable linkages include lipophilic association, such as formation of a liposome containing oligonucleotide and the protein effector covalently linked to a lipophilic molecule and thus associated with the liposome. Such lipophilic molecules include without limitation phosphotidylcholine, cholesterol and phosphatidylethanolamine, and synthetic neoglycolipids, such as syalyllacNAc-HDPE. In certain preferred embodiments, the operable association may not be a physical association, but simply a simultaneous existence in the body, for example, when the antisense oligonucleotide is associated with one liposome and the protein effector is associated with another liposome.

The method and compositions according to the invention are useful for a variety of purposes. For example, they can be used as "probes" of the physiological function of a gene product by being used to inhibit the activity and/or expression of the gene product in an experimental cell culture or animal system and to evaluate the effect of inhibiting such activity and/or expression. This is accomplished by administering to a cell or an animal an antisense oligonucleotide which inhibits expression of a gene and a protein effector of a product of the gene according to the invention and observing any phenotypic effects. This method according to the invention is preferable to traditional "gene knockout" approaches because it is easier to use, and can be used to inhibit the gene and/or a product of the gene at selected stages of development or differentiation. For example, where the gene encodes DNA MeTase, the method according to the invention can serve as a probe to test the role of DNA methylation in various stages of development.

Finally, the methods and compositions according to the invention are useful in therapeutic approaches to human diseases including benign and malignant tumors involving the modulation and/or the suppression of gene expression. The anti-tumor utility of antisense oligonucleotides according to the invention is described in detail elsewhere in this specification.

All of the aspects of the invention disclosed herein are applicable to the synergistic inhibition of any target gene and is not limited to any particular gene or gene product. More specifically, the invention relates to the inhibition of any target gene by the concurrent or sequential inhibition of the same target gene at both the genetic level (i.e., at either the DNA or the mRNA level) and at the protein level. As exemplified herein for DNA MeTase, histone deacetylase, and thymidylate synthase, such methods and compositions are useful for a variety of purposes. The invention results in an improved inhibitory effect, thereby reducing the effective concentrations of either or both the gene level and the protein levels inhibitors required to obtain a given inhibitory effect as compared to those necessary when either inhibitor is used individually.

Thus, the methods and compositions according to all aspects of the invention are useful in therapeutic approaches to human diseases involving the modulation and/or suppression of gene expression of a particular target gene. Particularly preferred disease targets include, without limitation, various cancers. The methods and compositions according to the invention may also be used to activate silenced genes to provide missing gene functions and thus improve a given condition. For example, the methods and compositions of the invention are useful to downregulate and/or suppress abnormal oncogene expression and activity thereby inhibiting tumorigenesis.

In certain embodiments, each of the antisense oligonucleotide and the protein effector is admixed with a pharmaceutically acceptable carrier prior to contact with the cell. In certain embodiments, the antisense oligonucleotide and the protein effector are mixed together prior to contact with the cell.

In certain preferred embodiments of the first aspect of the invention, the cell is contacted separately with each of the antisense oligonucleotide and the protein effector. For example, the cell may be contacted with the antisense oligonucleotide prior to being contacted with the protein effector. The cell may be contacted with an effective synergistic amount of one or more antisense oligonucleotides of the invention, followed by contact with an effective synergistic amount of one or more protein effectors of the invention. This is particularly useful where the gene encodes a DNA MeTase and where the contacted cell is desired to undergo apoptosis or be arrested in the S phase of the cell cycle.

In another example, the cell may be contacted with the protein effector prior to being contacted with the antisense oligonucleotide. This is particularly useful where the gene encodes a DNA MeTase where the contacted cell is desired to be arrested in the $G_1$ phase of the cell cycle.

Furthermore, where the gene encodes, for example, DNA MeTase, the methods and compositions according to the invention may also be used to activate silenced genes to provide a missing gene function and thus ameliorate disease symptoms. For example, the diseases beta thalassemia and sickle cell anemia are caused by aberrant expression of the adult beta globin gene or of a mutated gene. Most individuals suffering from these diseases have normal copies of the fetal gene for beta globin. However, the fetal gene is hypermethylated and is silent. Activation of the fetal globin gene could provide the needed globin function, thus ameliorating the disease symptoms. In addition, the methods and compositions according to the invention may be used as gene therapy tools to maintain, activate, and/or modulate the expression of exogenous sequences otherwise liable to inhibition by methylation.

Accordingly, in a certain embodiment of the first aspect of the invention, the gene encodes DNA MeTase. Particularly preferred non-limiting examples of antisense oligonucleotides complementary to regions of RNA or double-stranded DNA encoding DNA MeTase utilized in the method according to the invention are shown in Table 1. DNA MeTase RNA (see e.g., Yen et al. (1992) Nucl. Acids Res. 9: 2287–2291; Yoder et al. (1996) J. Biol. Chem. 271:

31092–31097; Bester et al. (1988) J. Mol. Bio. 203(4): 971–983) or double stranded DNA regions include, without limitation, intronic sequences, untranslated 5' and 3' regions, intron-exon boundaries as well as coding sequences from the DNA MeTase gene (see Ramchandani et al. (1998) Biol. Chem. 379(4–5): 535–540).

Particularly preferred oligonucleotides have nucleotide sequences of from about 13 to about 35 nucleotides which include the nucleotide sequences shown in Table 1. Yet additional particularly preferred oligonucleotides have nucleotide sequences of from about 13 to about 19 nucleotides of the nucleotide sequences shown in Table 1.

TABLE 1

| SEQ ID NO. | SEQUENCE | TARGET (*) |
|---|---|---|
| 1 | 5'-AAG CAT GAG CAC CGT TCT CC-3' | 513–532 |
| 2 | 5'-TTC ATG TCA GCC AAG GCC AC-3' | 5218–5199 |
| 5 | 5'-GCT GTC TCT TTC CAA ATC TT-3' | 323–342 |
| 6 | 5'-TTT CTG TTA AGC TGT CTC TT-3' | 333–352 |
| 7 | 5'-TTC TCC TTC ACA CAT TCC TT-3' | 352–371 |
| 8 | 5'-CGT GCA AGA GAT TCA ATT TC-3' | 369–388 |
| 9 | 5'-AAG TCA CAT AAC TGA TTC TT-3' | 409–428 |
| 10 | 5'-CTC GGA TAA TTC TTC TTT AC-3' | 643–662 |
| 11 | 5'-CCA GGT AGC CCT CCT CGG AT-3' | 456–475 |
| 12 | 5'-AGG GAT TTG ACT TTA GCC AG-3' | 232–251 |
| 13 | 5'-TCC AAG GAC AAA TCT TTA TT-3' | 496–515 |
| 14 | 5'-CAT GAG CAC CGT TCT CCA AG-3' | 510–529 |
| 15 | 5'-ACG TCC ATT CAC TTC CCG GT-3' | 536–555 |
| 16 | 5'-TCA CTT CTT GCT TGC TTC CC-3' | 565–584 |
| 17 | 5'-GCT TGG TTC CCG TTT TCT AC-3' | 556–575 |
| 18 | 5'-CTA GAC GTC CAT TCA CTT CC-3' | 540–559 |
| 19 | 5'-ACT CTA CGG GCT TCA CTT CT-3' | 577–576 |
| 20 | 5'-TCT GCC ATT CCC ACT CTA CG-3' | 589–608 |
| 21 | 5'-CAT CTG CCA TTC CCA CTC TA-3' | 591–610 |
| 22 | 5'-GGC ATC TGC CAT TCC CAC TC-3' | 593–612 |
| 23 | 5'-ATC GGA CTT GCT CCT CCT GG-3' | 650–669 |
| 24 | 5'-GGT GAC GGG AGG GCA GAA CT-3' | 5087–5106 |
| 25 | 5'-TGC CAG AAA CAG GGG TGA CG-3' | 5100–5119 |
| 26 | 5'-GTG CAT GTT GGG GAT TCC TG-3' | 5121–5140 |
| 27 | 5'-GTG AAC GGA CAG ATT GAC AT-3' | 5159–5178 |
| 28 | 5'-AGG CCA CAA ACA CCA TGT AC-3' | 5186–5205 |
| 29 | 5'-CGA ACC TCA CAC AAC AGC TT-3' | 5217–5236 |
| 30 | 5'-GAT AAG CGA ACC TCA CAC AA-3' | 5223–5242 |
| 31 | 5'-CTG CAC AAT TTG ATC ACT AA-3' | 5253–5272 |
| 32 | 5'-CAG AAA CAG GGG TGA CGG GA-3' | 5097–5116 |
| 33 | 5'-GCA CAA AGT ACT GCA CAA TT-3' | 5263–5282 |
| 34 | 5'-TCC AGA ATG CAC AAA GTA CT-3' | 5271–5290 |

(*) target reference numbering is in accordance with GenBank Accession No. X63692.

As used herein, a DNA MeTase protein effector preferably inhibits DNA MeTase. at least 5-fold, more preferably at least 10-fold, even more preferably at least 50-fold, and most preferably at least 100-fold more than it inhibits any unrelated protein.

In preferred embodiments, the DNA MeTase protein effector is a moiety capable of forming a stable adduct with DNA methyltransferase, thus mimicking the transient covalent intermediate complex believed to be formed during methylation (see, e.g., Wu and Santi (1987) J. Biol. Chem. 262: 4778–4786). Preferable examples of DNA MeTase protein effectors include without limitation nucleoside analogs such as 5-aza-2'-deoxycytidine (5-aza-dC), 5fluoro-2'-deoxycytidine, 5-aza-cytidine (5-aza-C), or 5,6dihydro-5-azacytidine or a pharmaceutically acceptable salt thereof. A method of synthesizing 5,6-dihydro-5-azacytidine from 5'-aza-cytidine is described in U.S. Pat. No. 4,058,602 which is hereby incorporated by reference in its entirety. Additional DNA MeTase protein effectors include the inhibitors of DNA methyltransferase enzyme, including hairpin oligonucleotides, described in PCT publication no. WO 97/44346 (PCT application no. PCT/IB97/00879).

In particularly preferred embodiments of all aspects of the invention, the antisense oligonucleotide is in operable association with a protein effector. The term "operable association" includes any association between the antisense oligonucleotide and the protein effector which allows an antisense oligonucleotide to inhibit DNA MeTase gene expression and allows protein effector(s) to inhibit DNA MeTase enzyme activity.

In preferred embodiments of the first aspect of the invention, the invention provides a method for inhibiting DNA MeTase in a cell comprising contacting the cell with an effective synergistic amount of an oligonucleotide which inhibits DNA MeTase expression and with an effective synergistic amount of a DNA MeTase protein effector.

In certain preferred embodiments of the first aspect of the invention, the gene encodes a DNA MeTase and the cell comprises a gene whose expression has been inactivated by methylation. Thus, expression of the gene is promoted and/reactivated in the contacted cell. Preferably, the invention provides compositions and methods for the reactivation of a tumor suppressor gene which has been inactivated by methylation in a cell, such as a neoplastic cell or a cell predisposed to become a neoplastic. By "neoplastic cell," as used herein for all aspects of the invention, is meant a cell that shows aberrant cell growth, such as increased cell growth. A neoplastic cell may be a hyperplastic cell, a cell that shows a lack of contact inhibition of growth in vitro, a tumor cell that is incapable of metastasis in vivo, or a cancer cell that is capable of metastasis in vivo. Any growth of neoplastic cells, whether metastatic or benign, is referred to herein as a tumor or a tumor growth.

In certain preferred embodiments, where the gene encodes DNA MeTase, the invention provides compositions and methods for the reactivation of a tumor suppressor gene which has been inactivated by methylation. In particularly preferred embodiments, the invention provides a method for the reactivation of a p16 tumor suppressor gene which had been inhibited by methylation.

In certain preferred embodiments of this aspect of the invention, where the gene encodes a product not limited to DNA MeTase, methods and compositions are provided for the modulation of target oncogenes such as, for example, the mutant forms of the RAS oncogene family which have been implicated in as many as 75% of human pancreatic cancers (see, e.g., Rodenhuis et al. (1992) Semin. Cancer Biol. 3(4): 241–247; Brentnall et al. (1995) Cancer Res. 55(19): 4264–4267).

In addition, the methods and compositions according to the invention may also be used to inhibit any number of target genes and/or products of these genes. Consequently, the methods and compositions of the invention are useful in therapeutic approaches to various human conditions such as inflammation or asthma as discussed herein.

Accordingly, in a certain embodiment of the first aspect of the invention, the gene encodes a histone deacetylase (HDAC). There are several related forms of histone deacetylases in the histone deacetylase family. The family includes HDAC-1, HDAC-2, HDAC-3, HDAC4, HDAC-5, and HDAC-6. Histone deacetylase activity is thought to modulate the accessibility of transcription factors to enhancer and promoter elements, and functional histone deacetylases have been implicated as a requirement in cell cycle progression in both normal and neoplastic cells. Thus, in certain embodiments of this aspect of the invention, the invention provides an inhibitor of a histone deacetylase (e.g., HDAC-1, HDAC-2, HDAC-3, HDAC-4, HDAC-5, and HDAC-6) using an oligonucleotide which inhibits a gene encoding at least one HDAC, and a HDAC protein effector capable of inhibiting a the activity and/or expression of at least one HDAC such as, for example, trichostatin A (TSA), depudecin, trapoxin, suberoylanilide hydroxamic acid (SAHA), FR901228 (Fujisawa Pharmaceuticals), MS-27-275 (Mitsui Pharmaceuticals), CI-994 (Parke Davis), oxamflatin (Shionogi and Co.), and sodium butyrate. An HDAC protein effector preferably inhibits HDAC-1, HDAC-2, HDAC-3, HDAC4, HDAC-5, and/or HDAC-6 at least 5-fold, more preferably at least 10-fold, most preferably at least 50-fold, and most preferably at least 100-fold more than it inhibits any unrelated protein. The antisense olignouncleotides according to this aspect of the invention are complementary to regions of RNA or double-stranded DNA that encode HDAC-1, HDAC-2, HDAC-3, HDAC4, HDAC-5, and/or HDAC-6 (see e.g., GenBank Accession Number U50079 for HDAC-1, GenBank Accession Number U31814 for HDAC-2, and GenBank Accession Number U75697 for HDAC-3). Particularly, preferred oligonucleotides have nucleotide sequences of from about 13 to about 35 nucleotides which include the nucleotide sequences shown in Tables 2 and 3. Yet additional particularly preferred oligonucleotides have nucleotide sequences of from about 15 to about 26 nucleotides of the nucleotide sequences shown in Tables 2 and 3.

TABLE 2

| SEQ ID NO. | SEQUENCE | TARGET (**) |
|---|---|---|
| 35 | 5'-GAG ACA GCA GCA CCA GCG GG-3' | 17–36 |
| 36 | 5'-ATG ACC GAG TGG GAG ACA GC-3' | 21–49 |
| 37 | 5'-GGA TGA CCG AGT GGG AGA CA-3' | 31–50 |
| 38 | 5'-CAG GAT GAC CGA GTG GGA GA-3' | 33–52 |
| 39 | 5'-TGT GTT CTC AGG ATG ACC GA-3' | 41–60 |
| 40 | 5'-GAG TGA CAG AGA CGC TCA GG-3' | 62–81 |
| 41 | 5'-TTC TGG CTT CTC CTC CTT GG-3' | 1504–1523 |
| 42 | 5'-CTT GAC CTC CTC CTT GAC CC-3' | 1531–1550 |
| 43 | 5'-GGA AGC CAG AGC TGG AGA GG-3' | 1565–1584 |
| 44 | 5'-GAA ACG TGA GGG ACT CAG CA-3' | 1585–1604 |
| 45 | 5'-CCG TCG TAG TAG TAA CAG ACT TT-3' | 138–160 |
| 46 | 5'-TGT CCA TAA TAG TAA TTT CCA A-3' | 166–187 |
| 47 | 5'-CAG CAA ATT ATG AGT CAT GCG GAT TC-3' | 211–236 |

(**) target reference numbering is in accordance with HDAC-1, GenBank Accession Number U50079.

TABLE 3

| SEQ ID NO. | SEQUENCE | TARGET (***) |
|---|---|---|
| 50 | 5'-CTC CTT GAC TGT ACG CCA TG-3' | 1–20 |
| 51 | 5'-TGC TGC TGC TGC TGC TGC CG-3' | 121–141 |
| 52 | 5'-CCT CCT GCT GCT GCT GCT GC-3' | 132–152 |
| 53 | 5'-CCG TCG TAG TAG TAG CAG ACT TT-3' | 138–160 |
| 54 | 5'-TGT CCA TAA TAA TAA TTT CCA A-3' | 166–187 |
| 55 | 5'-CAG CAA GTT ATG GGT CAT GCG GAT TC-3' | 211–236 |
| 56 | 5'-GGT TCC TTT GGT ATC TGT TT-3' | 1605–1625 |

(***) target reference numbering is in accordance with HDAC-2, GenBank Accession Number U31814.

In another embodiment, the targeted gene of the invention encodes a thymidylate synthase. The thymidylate synthase-encoding gene can be targeted using an oligonucleotide which inhibits thymidylate synthase and a thymidylate synthase protein effector capable of inhibiting thymidylate synthase activity such as, for example, the nucleoside analog 5-fluorouracil (5-FU), Tomudex™ (Raltitrexed or Zeneca ZD1694), Zeneca ZD9331, Thymitaq™ (AG337, Agouron), AG331 (Agouron), Ly231514 (Lilly), and BW1843U89. A thymidylate synthase protein effector preferably inhibits thymidylate synthase at least 5-fold, more preferably at least 10-fold, most preferably at least 50-fold, and most preferably at least 100-fold more than it inhibits any unrelated protein. The antisense olignouncleotides according to this aspect of the invention are complementary to regions of RNA or double-stranded DNA that encode thymidylate synthase (see e.g., GenBank Accession Number X02308). Particularly, preferred oligonucleotides have nucleotide sequences of from about 15 to about 35 nucleotides which include the nucleotide sequences shown in Table 4. Yet additional particularly preferred oligonucleotides have nucleotide sequences of from about 13 to about 20 nucleotides of the nucleotide sequences shown in Table 4.

TABLE 4

| SEQ ID NO. | SEQUENCE | TARGET (****) |
|---|---|---|
| 57 | 5'-GGA GGC AGG CCA AGT GGT CC-3' | 11–30 |
| 58 | 5'-CGG AGG CAG GCC AAG TGG TC-3' | 12–31 |
| 59 | 5'-GAC GGA GGC AGG CCA AGT GG-3' | 42–61 |
| 60 | 5'-ACG GAG GCA GGC GAA GTG GC-3' | 69–88 |
| 61 | 5'-GGA CGG AGG CAG GCG AAG TG-3' | 71–90 |
| 62 | 5'-AAG CAC CCT AAA CAG CCA TT-3' | 1035–1054 |
| 63 | 5'-TTG AAA GCA CCC TAA ACA GC-3' | 1039–1058 |
| 64 | 5'-ACA ATA TCC TTC AAG CTC CT-3' | 1059–1078 |
| 65 | 5'-CCT AAA GAC TGA CAA TAT CC-3' | 1070–1089 |
| 66 | 5'-AAT TAA TAA CTG ATA GGT CA-3' | 1163–1182 |
| 67 | 5'-CCA GTG GCA ACA TCC TTA AA-3' | 1183–1202 |
| 68 | 5'-CAC AGT TAC ATT TGC CAG TG-3' | 1197–1216 |
| 69 | 5'-TTA TGG AAA GAA CTG GCA CA-3' | 1213–1232 |
| 70 | 5'-CCT CAG CAT TGT CAG ATA CC-3' | 1260–1279 |
| 71 | 5'-TTC ATA ACC TCA GCA TTG TC-3' | 1267–1286 |
| 72 | 5'-ACA TTT CAT TCT CCT CAC TT-3' | 1289–1308 |
| 73 | 5'-CAT ACA TTT CAT TCT CCT CA-3' | 1292–1311 |
| 74 | 5'-CCA ACC TTC TTT ATA AGT AC-3' | 1351–1370 |
| 75 | 5'-AAT TCA CCA ACC TTC TTT AT-3' | 1357–1376 |
| 76 | 5'-TTG AGG GAA TAG CTT GTG AA-3' | 1419–1438 |
| 77 | 5'-TTA CTC AGC TCC CTC AGA TT-3' | 1438–1457 |
| 78 | 5'-AAC ACT TCT TTA TTA TAG CA-3' | 1513–1532 |

(****) target reference numbering is in accordance with GenBank Accession Number X02308

Yet another target is dihydrofolate reductase (DHFR) using an oligonucleotide which inhibits DHFR expression and a DHFR protein effector capable of inhibiting DHFR activity such as, for example, methotrexate (MTX) (e.g., for the treatment of tumors and/or autoimmune inflammatory disorders). A DHFR protein effector preferably inhibits DHFR at least 5-fold, more preferably at least 10-fold, most preferably at least 50-fold, and most preferably at least 100-fold more than it inhibits any unrelated protein.

Additional preferred targets (e.g., for the treatment of inflammation) according to this aspect of the invention include: cycloxygenase-2 (COX-2) using an oligonucleotide which inhibits (COX-2) expression and a COX-2 protein effector which inhibits (COX-2) activity such as, for example, Celecoxib (SC58635); telomerase using an oligonucleotide which inhibits telomerase expression and a protein effector which inhibits telomerase activity such as, for example, 3azido-3-deoxythymidine; Topoisomerase I using an oligonucleotide which inhibits Topoisomerase I expression and a Topoisomerase I protein effector which inhibits Topoisomerase I activity such as, for example, Topotecan (Smithline) or Camptothecin; Topoisomerase II using an oligonucleotide which inhibits Topoisomerase II expression and a Topoisomerase II protein effector which inhibits Topoisomerase II activity such as, for example, Etoposide (Bristol Myers Squibb); DNA Polymerase α using an oligonucleotide which inhibits DNA Polymerase α expression and a DNA Polymerase α protein effector which inhibits DNA Polymerase α activity such as, for example, Ara-C; aromatase using an oligonucleotide which inhibits aromatase expression and a protein effector which inhibits aromatase activity such as, for example, Letrozole (Femara, Novartis) anastrozole (Arimidex, Zeneca) vorozole (Rizivor); 5-α-reductase using an oligonucleotide which inhibits 5-α-reductase expression and a 5-α-reductase protein effector which inhibits 5-α-reductase activity such as, for example, FK143 (Fujissawa), Ly300502 (Eli Lilly and Co.); Neutrophil elastase (e.g., for the treatment of inflammation) using an oligonucleotide which inhibits Neutrophil elastase expression and a Neutrophil elastase protein effector which inhibits Neutrophil elastase activity such as, for example, ONO-5046.Na; farnesyltransferase using an oligonucleotide which inhibits farnesyltransferase expression and a farnesyltransferase protein effector which inhibits farnesyltransferase activity such as, for example, L744832 (Merck), or BMS186511 (Bristol Myers Squibb); Cyclin kinases (CDKs) using an oligonucleotide which inhibits CDKs expression and a CDKs protein effector which inhibits CDKs activity such as for example Flavopiridol; the epidermal growth factor receptor (EGFR) using an oligonucleotide which inhibits EGFR expression and a EGFR protein effector which inhibits EGFR activity such as, for example, PD153035 (Parke-Davis); Her-2/Neu using an oligonucleotide which inhibits Her-2/Neu expression and a Her-2/Neu protein effector which inhibits Her-2/Neu activity such as, for example, Tyrphostin, or AG825 (Agouron); Leukotriene receptor LTD4 (e.g., for the treatment of asthma) using an oligonucleotide which inhibits Leukotriene receptor LTD4 expression and a Leukotriene receptor LTD4 protein effector which inhibits Leukotriene receptor LTD4 activity such as, for example, MK571 (Merck); P-glycoprotein using an oligonucleotide which inhibits P-glycoprotein expression and a P-glycoprotein protein effector which inhibits P-glycoprotein activity such as, for example, PSC 833, a cyclosporin A analog.

In a second aspect, the invention provides a method for treating a disease responsive to inhibition of a gene. The method according to this aspect of the invention includes administering to a mammal, including a human, which has at least one cell affected by the disease, of an antisense oligonucleotide which inhibits expression of the gene, and a therapeutically effective synergistic amount of a protein effector of a product of the gene. The antisense oligonucleotide and the protein effectors are as described for the first aspect according to the invention. "A disease responsive to inhibition of a gene" is one which is associated with altered activity, levels, or functions of the gene and/or a product of the gene. The symptoms of such a disease are alleviated and/or eliminated by the modulation of the activity of the gene or of a product of the gene. "A cell affected by the disease" is a cell which has altered activity, levels, or functions of the gene and/or a product of the gene.

For example, "a disease responsive to DNA MeTase inhibition" is one which is associated with altered methylation pattern(s) or altered DNA MeTase activity, levels, or functions. The symptoms of such a disease are alleviated and/or eliminated by the modulation of DNA MeTase activity. "A cell affected by a disease responsive to DNA MeTase inhibition" is a cell which has altered methylation pattern(s) or altered DNA MeTase activity, levels, or functions.

In certain embodiments of the second aspect of the invention, the mammal is administered a therapeutically effective synergistic amount of at least one antisense oligonucleotide and/or at least one protein effector for a therapeutically effective period of time.

The terms "therapeutically effective synergistic amount" and "therapeutically effective period of time" are used to denote treatments at dosages and for periods of time effective to achieve the therapeutic result sought. The therapeutically effective synergistic amount of the antisense oligonucleotide and/or the therapeutically effective synergistic amount of the protein effector is/are less than the amount(s) empirically found necessary to inhibit the gene when either the antisense oligonucleotide or the protein effector are used individually. In preferred embodiments, the combined inhibitory effect of the antisense oligonucleotide and the protein effector according to the invention are more than additive, i.e., the combined inhibitory effect is greater than the expected total effect calculated on the basis of the sum of the individual effects. One of skill in the art will appreciate that such synergistic effect resulting in a lower effective concentration of either the antisense oligonucleotide, the protein effector or both may vary considerably depending on the tissue, organ, or the particular mammal or patient to be treated according to the invention. Furthermore, one of skill will appreciate that the therapeutically effective synergistic amount of either the antisense oligonucleotide or the protein inhibitor may be lowered or increased by fine tuning and altering the amount of the other component. The invention therefore provides a method to tailor the administration/treatment to the particular exigencies specific to a given mammal or patient. As illustrated in the following examples, therapeutically effective synergistic ranges may be easily determined, for example, empirically by starting at relatively low amounts and by step-wise increments with concurrent evaluation of inhibition. In particularly preferred embodiments, the therapeutic composition of the invention is administered systemically at a sufficient dosage to attain a blood level of antisense oligonucleotide from about 0.01 $\mu$M to about 20 $\mu$M and of protein effector from about 0.01 $\mu$M to about 10 $\mu$M. In particularly preferred embodiments, the therapeutic composition is administered at a sufficient dosage to attain a blood level of antisense oligonucleotide from about 0.05 $\mu$M to about 15 $\mu$M and of protein effector from about 0.05 $\mu$M to about 10 $\mu$M. In even more preferred embodiments, the blood level of antisense oligonucleotide is from about 0.1 $\mu$M to about 10 $\mu$M and the blood level of protein effector is from about 0.1 $\mu$M to about 7 $\mu$M. For localized administration, much lower concentrations than this may be effective. Preferably, a total dosage of antisense oligonucleotide will range from about 0.1 mg to about 30 mg oligonucleotide per kg body weight per day, while, a total dosage of protein effector will range from about 0.01 mg to about 5 mg protein effector per kg body weight per day. In more preferred embodiments, a total dosage of antisense oligonucleotide will range from about 1 mg to about 20 mg oligonucleotide per kg body weight per day, while, a total dosage of protein effector will range from about 0.1 mg to about 4 mg protein effector per kg body weight per day. In most preferred embodiments, a total dosage of antisense oligonucleotide will range from about 2 mg to about 10 mg oligonucleotide per kg body weight per day, while, a total dosage of protein effector will range from about 0.1 mg to about 1 mg protein effector per kg body weight per day. In particularly preferred embodiments, the therapeutically effective synergistic amount of antisense oligonucleotide is 0.5 mg oligonucleotide per kg body weight per day, and the effective synergistic amount of protein effector is 0.1 mg per kg body weight per day.

In certain embodiments, each of the antisense oligonucleotide and the protein effector is admixed with a pharmaceutically acceptable carrier prior to administration to the mammal. In certain embodiments, the antisense oligonucleotide and the protein effector are mixed together prior to administration to the mammal.

Each of the antisense oligonucleotides and the protein effectors according to all aspects of the invention may optionally be formulated with any of the well known pharmaceutically acceptable carriers or diluents. Pharmaceutically acceptable carriers and their formulations are well-known and generally described in, for example, *Remington's Pharmaceutical Sciences* (18th Edition, ed. A. Gennaro, Mack Publishing Co., Easton, Pa., 1990). Formulations of the invention may further contain one or more DNA MeTase inhibitors and/or one or more additional DNA MeTase antisense oligonucleotide(s), and/or one or more protein effector(s), or it may contain any other pharmacologically active agent. If an antisense oligonucleotide is administered with a protein effector, both may be admixed together with a pharmaceutically acceptable carrier. Where the antisense oligonucleotide is administered separately from the protein effector, each may be mixed with a pharmaceutically acceptable carrier. It will understood that where the antisense oligonucleotide and the protein effector are administered separately, the same pharmaceutically acceptable carrier need not be the same for both. Rather, the pharmaceutically acceptable carrier is dependent on the route of administration of the antisense oligonucleotide and of the protein effector.

The compositions of the invention may be administered by any appropriate means. For example, the compositions of the invention may be administered to an mammal within a pharmaceutically-acceptable diluent, carrier, or excipient, in unit dosage form according to conventional pharmaceutical practice. Administration may begin before the mammal is symptomatic for a disease responsive to inhibition of a gene. For example, where the disease is responsive to DNA MeTase inhibition, such as cancer, administration may begin before the animal is symptomatic.

Any appropriate route of administration may be employed, including, without limitation, parenteral intravenous, intra-arterial, subcutaneous, sublingual, transdermal, topical, intrapulmonary, intramuscular, intraperitoneal, by inhalation, intranasal, aerosol, intrarectal, intravaginal, or by oral administration. Therapeutics may be in the form of liquid solutions or suspensions; for oral administration, formulations may be in the form of tablets or capsules; and for intranasal formulations, in the form of powders, nasal drops, or aerosols. The compositions may be administered locally to the area affected by a disease responsive to inhibition of a gene. For example, where the disease is responsive to DNA MeTase inhibition and is a cancer, the composition may be administered directly into the tumor mass). The compositions of the invention may be administered systemically.

In certain preferred embodiments of the second aspect of the invention, the antisense oligonucleotide and the protein effector are administered separately to the mammal. For example, the antisense oligonucleotide may be administered to the mammal prior to administration to the mammal of the protein effector. The mammal may receive one or more dosages of antisense oligonucleotide prior to receiving one ore more dosages of protein effector. Where the gene encodes a DNA MeTase, this administration schedule is particularly useful where the cell affected by the disease is desired to undergo apoptosis or be arrested in the S phase of the cell cycle. Such an administration schedule may be useful, for example, where the gene encodes DNA MeTase and where the disease is an aggressive cell proliferative disease such as metastatic cancer.

In another example, the protein effector may be administered to the mammal prior to administration of the antisense oligonucleotide. The mammal may receive one or more dosages of protein effector prior to receiving one or more dosages of antisense oligonucleotide. Where the gene encodes a DNA MeTase, this administration schedule is particularly useful where the cell affected by the disease is desired to be arrested in the $G_1$ phase of the cell cycle. Such an administration schedule may be useful, for example, where the gene encodes DNA MeTase and where the disease is associated with cells whose growth arrest, rather than death, is desired. One non-limiting example of such a disease is transplantation graft rejection, where the host's immune cells (e.g., lymphocytes and leukocytes) proliferate in response to the foreign cells in the transplanted graft. Arrest of growth of the host's immune cells, rather than the death of these cells by apoptosis, is desirable.

In certain preferred embodiments of the second aspect of the invention, the gene encodes a DNA MeTase and the cell affected by the disease comprises a gene whose expression has been inactivated by methylation. In certain embodiments, expression of the gene is promoted, restored, and/or reactivated in the cell in the mammal to which has been administered a therapeutically effective synergistic amount of an antisense oligonucleotide and a therapeutically effective synergistic amount of a protein effector. In preferred embodiments, the gene is the $p16^{ink4}$ tumor suppressor gene.

In certain embodiments of this aspect of the invention, the gene encodes a DNA methyltransferase. In certain embodiments, the protein effector is selected from the group consisting of 5-aza-cytidine, 5-aza-2'-deoxycytidine, 5-fluoro-2'-deoxycytidine and 5,6-dihydro-5-azacytidine.

In certain embodiments of this aspect, the gene encodes a histone deacetylase. In certain embodiments, the protein effector is selected form the group consisting of trichostatin A, depudecin, trapoxin, suberoylanilide hydroxamic acid, FR901228, MS-27-275, CI-994, and sodium butyrate.

In certain embodiments of this aspect, the gene encodes a thymidylate synthase. In certain embodiments, the protein effector is selected form the group consisting of 5-fluorouracil (5-FU), Tomudex, Raltitrexed, Zeneca ZD1694, Zeneca ZD9331, Thymitaq, AG331, Ly231514, and BW1843U89.

In a third aspect, the invention provides a method for inhibiting tumor growth in a mammal. The method according to this aspect of the invention includes administering to a mammal, including a human, which has at least one neoplastic cell present in its body a therapeutically effective synergistic amount of an antisense oligonucleotide which inhibits expression of a gene involved in tumorigenesis, and a therapeutically effective synergistic amount of a protein effector of a product of the gene. As used herein, "a gene involved in tumorigenesis," is a gene whose aberrant expression is associated with tumorigenesis. Exemplary genes involved in tumorigenesis include the genes encoding DNA methyltransferases, histone deaceylases (all forms), and thymidylate synthase. By "tumorigenesis" is meant the genetic and phenotypic events involved in the progression of a normal cell to become a neoplastic cell. The antisense oligonucleotide and the protein effectors are as described for the first aspect according to the invention. Administration and dosages are as described for the second aspect according to the invention.

In certain embodiments of this aspect of the invention, the gene encodes a DNA methyltransferase. In certain embodiments, the protein effector is selected from the group consisting of 5-aza-cytidine, 5-aza-2'-deoxycytidine, 5-fluoro-2'- deoxycytidine and 5,6-dihydro-5-azacytidine.

In certain embodiments of this aspect, the gene encodes a histone deacetylase. In certain embodiments, the protein effector is selected form the group consisting of trichostatin A, depudecin, trapoxin, suberoylanilide hydroxamic acid, FR901228, MS-27-275, CI-994, and sodium butyrate.

In certain embodiments of this aspect, the gene encodes a thymidylate synthase. In certain embodiments, the protein effector is selected form the group consisting of 5-fluorouracil, Tomudex, Raltitrexed, Zeneca ZD1694, Zeneca ZD9331, Thymitaq, AG331, Ly231514, and BW1843U89.

In embodiments of the third aspect of the invention, the mammal is administered a therapeutically effective synergistic amount of at least one antisense oligonucleotide and/or at least one protein effector for a therapeutically effective period of time. The terms, "therapeutically effective synergistic amount" and "therapeutically effective period of time," are as described in the second aspect of the invention. In certain embodiments of the third aspect, each of the antisense oligonucleotide and the protein effector is admixed with a pharmaceutically acceptable carrier prior to administration to the mammal. In certain embodiments, the antisense oligonucleotide and the protein effector are mixed prior to administration to the mammal.

In certain preferred embodiments of the third aspect of the invention, the the antisense oligonucleotide and the protein effector are separately administered to the mammal. For example, the antisense oligonucleotide may be administered to the mammal prior to the administration of the protein effector. This is desirable where the gene encodes a DNA MeTase and where the neoplastic cell in the mammal is desired to undergo apoptosis or be arrested in the S phase of the cell cycle. This administration schedule is particularly useful, for example, in the treatment of an aggressive, metastatic tumor such as melanoma.

Alternatively, the protein effector may be administered to the mammal prior to the administration of the antisense oligonucleotide. This schedule is desirable where the gene encodes a DNA MeTase and where the neoplastic cells in the mammal is desired to be growth arrested in the G, phase of the cell cycle. This administration schedule is particularly useful, for example, in the treatment of slower growing tumors (e.g., prostate cancer) or in the treatment of infirmed patients where the presence of apoptotic cells is not desirable.

In certain preferred embodiments of the third aspect of the invention, where the gene encodes a DNA MeTase, the neoplastic cell further comprises a gene whose expression has been inactivated by methylation. In certain embodiments, expression of the gene is promoted, restored, and/or reactivated in the neoplastic cell in the mammal to which has been administered a therapeutically effective synergistic amount of an antisense oligonucleotide and a therapeutically effective synergistic amount of a protein effector. In preferred embodiments, the gene is the p16$^{ink4}$ tumor suppressor gene.

In a fourth aspect, the invention provides an inhibitor of a gene comprising an antisense oligonucleotide which inhibits expression the gene in operable association with a protein effector of a product of the gene. In certain embodiments of this aspect of the invention, the antisense oligonucleotide is in operable association with two or more protein effectors.

The antisense oligonucleotide and protein effector of this aspect of the invention as as described for the first aspect according to the invention.

In certain embodiments of the fourth aspect of the invention, the gene encodes a DNA methyltransferase. In certain embodiments, the protein effector is selected from the group consisting of 5-aza-cytidine, 5-aza-2'-deoxycytidine, 5-fluoro-2'-deoxycytidine and 5,6-dihydro-5-azacytidine. In certain embodiments, the gene encodes a histone deacetylase. In certain embodiments, the protein effector is selected form the group consisting of trichostatin A, depudecin, trapoxin, suberoylanilide hydroxamic acid, FR901228, MS-27-275, CI-994, and sodium butyrate. In certain embodiments, the gene encodes a thymidylate synthase. In certain embodiments, the protein effector is selected form the group consisting of 5-fluorouracil, Tomudex, Raltitrexed, Zeneca ZD1694, Zeneca ZD9331, Thymitaq, AG331, Ly231514, and BW1843U89.

In a fifth aspect, the invention provides a pharmaceutical composition comprising an inhibitor of a gene comprising an antisense oligonucleotide in operable association with a protein effector. In certain embodiments, the composition further comprises a pharmaceutically acceptable carrier.

In a sixth aspect, the invention provides a method for investigating the role of a gene and/or a product of that gene in cellular growth, including the growth of tumor cells. In the method according to this aspect, the cell type of interest (e.g., a neoplastic cell) is contacted with a synergistic amount of an antisense oligonucleotide which inhibits expression of the gene and a synergistic amount of a protein effector of a product of the gene, as described for the first aspect according to the invention, resulting in inhibition of expression of the gene in the cell. The combinations described herein may be administered at different points in the cell cycle (e.g., at the $G_1$ phase, S phase, or $G_2$/M phase), or in conjunction with promoters or inhibitors of cell growth to determine the role of the gene (e.g., the gene encoding DNA MeTase) in the growth of the cell type of interest. In certain embodiments, the cell is a neoplastic cell.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

Example 1

Selection of Antisense Oligonucleotides Capable of Inhibiting MeTase Expression in Neoplastic cells To identify antisense oligodeoxynucleotides capable of inhibiting DNA MeTase gene expression in human neoplastic cells, 85 phosphorothioate oligodeoxynucleotides (each 20 base pairs in length) bearing sequences complimentary to the 5' and 3' regions of human DNA MeTase mRNA and sequences complimentary to intron-exon boundaries were synthesized and screened for antisense activity. As shown in FIG. 1 the two DNA MeTase mRNA regions were identified to be highly sensitive to antisense inhibition were targeted by MG88 having the sequence 5'-AAG CAT GAG CAC CGT TCU CC-3' (SEQ ID NO:1) (this oligonucleotide is targeted to the DNA MeTase mRNA 5'UTR at nucleotides 532 to 513) and MG98 having the sequence 5'-UUC ATG TCA GCC AAG GCC AC-3' (SEQ ID NO:2) (this oligonucleotide is targeted to the DNA MeTase mRNA 3'UTR at nucleotides 5218 to 5199). These oligonucleotides were chemically modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of each oligonucleotide consisted of a phosphorothioate linkage between adjoining nucleotides. MG88 and MG98 have $IC_{50}$ values of 40 nM and 45 nM for inhibition of DNA MeTase mRNA, respectively.

MG88 was next tested for an ability to inhibit DNA MeTase mRNA in two human neoplastic cells, A549 (human non-small cell lung carcinoma cells) and T24 (human bladder cancer cells). Cells were transfected with lipofectin only (6.25 μg/ml), or lipofectin plus 20, 40, or 80 nM of MG88 or control oligonucleotide MG208 having the sequence 5'-AAC GAT CAG GAC CCT TGU CC-3'(SEQ ID NO:4). MG208 was modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of MG208 consisted of a phosphorothioate linkage between adjoining nucleotides.

Figure 2:
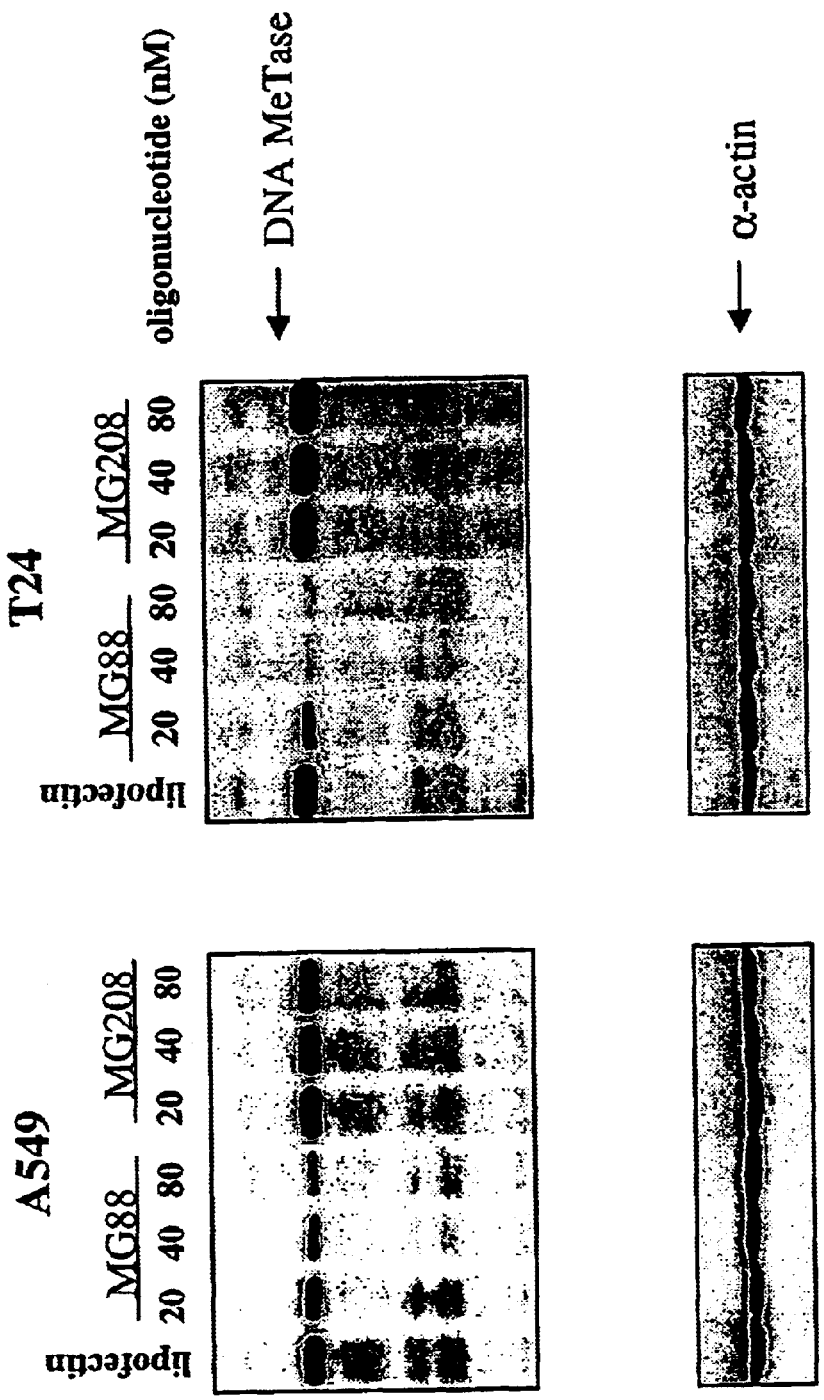
FIG. 2 is a representation of autoradiographs of Western blotting analyses showing that treatment with 40 nM or 80 nM of a representative, non-limiting antisense oligonucleotide, MG88 (SEQ ID No:1), results in an inhibition of MeTase protein expression in both A549 and T24 cells.

The MG88 and MG208 oligonucleotides were diluted to the desired concentration from a 0.1 mM stock solution in the transfection media. Cells were exposed to oligonucleotide plus lipofectin (or lipofectin only) for four hours on day 0 and four hours on day 1 (after each four hour treatment, cells were returned to complete media). On day 2 (i.e., 48 hours after the first treatment on day 0), cells were harvested, whole cell lysates were prepared, and DNA MeTase protein levels were analyzed by Western blotting analysis with a DNA MeTase-specific rabbit polyclonal antibody (generated according to standard techniques of a glutathione S -transferase fusion protein containing the first 10 kDa amino terminus from DNA methyltransferase protein). As shown in FIG. 2, treatment with MG88, but not control MG208, produced dose-dependent reduction in DNA MeTase protein levels. Equal loading of all lanes was confirmed by blotting for α-actin protein levels with an actin-specific rabbit polyclonal antibody (commercially available from Santa Cruz Biotech., Santa Cruz, Calif.).

Example 2

Inhibition of the p16 Tumor Suppressor by targeting DNA MeTase

The cyclin-dependent kinase inhibitor (CDKI) $p16^{ink4A}$ regulates the transition from $G_1$ to S-phases of the cell cycle (Serrano et al. (1993) Nature 366: 704–707). Inactivation of $p16^{ink4A}$ is one of the most frequently observed abnormalities in human cancer (Serrano et al., supra). Transcriptional inactivation and associated hypermethylation of the $p16^{ink4A}$ promote region have also been observed in virtually all types of cancer (Gonzales-Zulueta et al. (1995) Cancer Res. 55: 4531–4535; Merlo et al. (1995) Nat. Med. 7: 686–692; Costello et al. (1996) Cancer Res. 56: 2405–2410; Lo et al., Cancer Res. 56: 2721–2725). To investigate the effect of specifically reducing cellular DNA MeTase levels on the expression and methylation status of a silenced $p16^{ink4A}$ gene, T24 human bladder cancer cells that contain a hypermethylated and silenced $p16^{ink4A}$ gene were transfected with 40 nM or 75 nM MG88 or control oligonucleotide MG208 with 6.25 μg/ml lipofectin for four hours each day for up to 10 consecutive days. On days 3, 5, 8, and 10, $p16^{ink4A}$ protein levels were then analyzed by immunoprecipitation followed by Western blotting analysis with a $p16^{ink4A}$ protein-specific antibody (PharMingen). HeLa cells were used as a positive (+) control for $p16^{ink4A}$ protein expression.

Figure 3A:
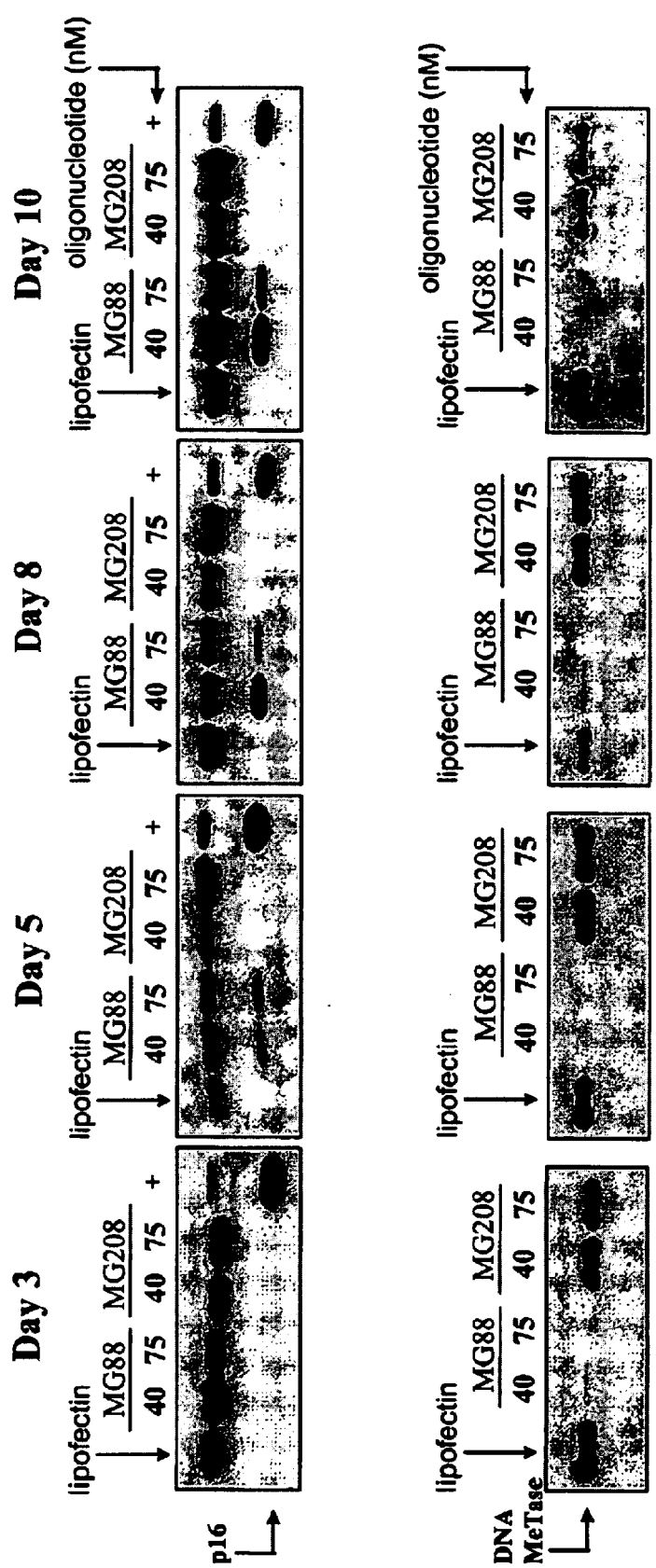
FIG. 3A is a representation of autoradiographs of a series of immunoprecipitations followed by Western blotting analyses of T24 cell lysates showing that $p16^{ink4}$ protein levels (upper panel) increase as DNA MeTase protein levels (lower panel) decrease following treatment of the cells for 3, 5, 8, or 10 days with 40 or 75 nM of a representative, non-limiting antisense oligonucleotide of the invention, MG88 (SEQ ID No:1), where HeLa cells served as a positive control for $p16^{ink4}$ protein expression.
Figure 3B:
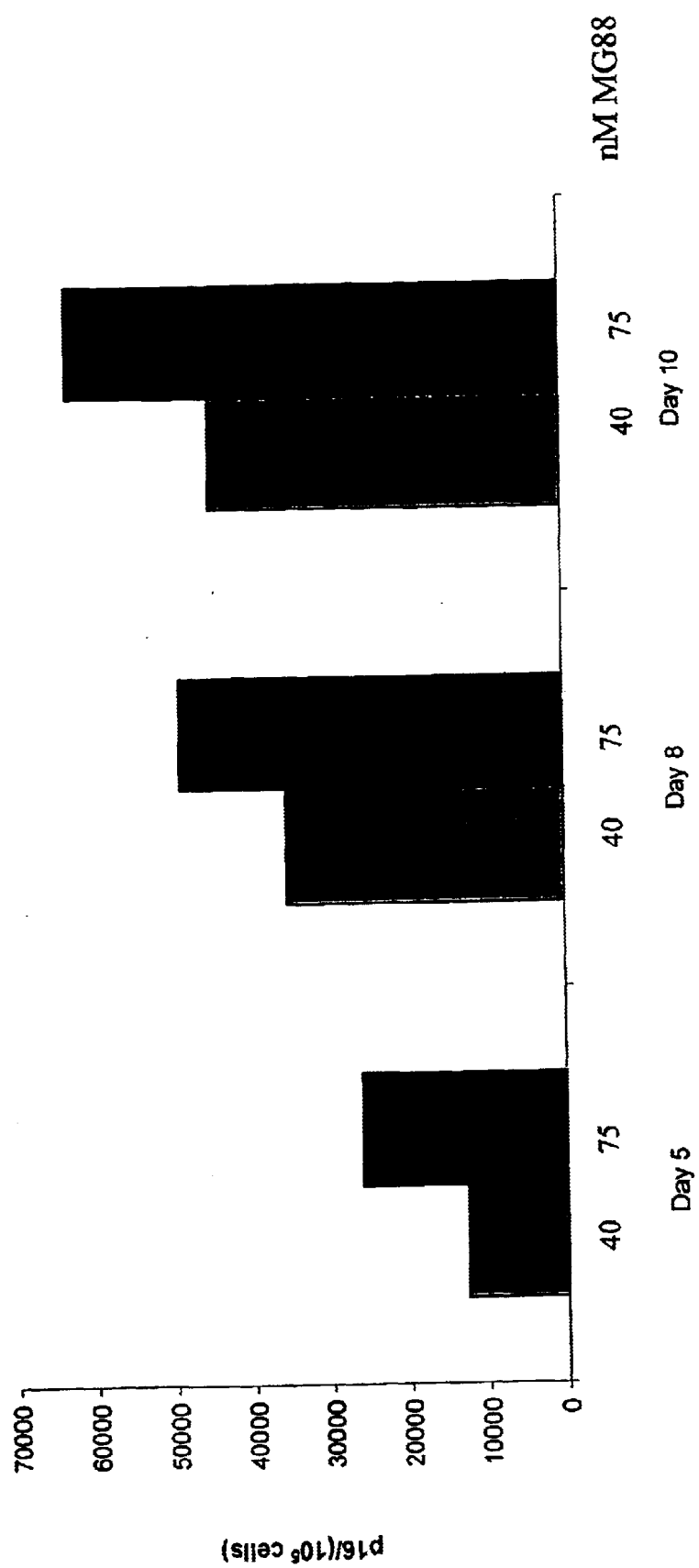
FIG. 3B is a graphic representation of $p16^{ink4}$ protein to levels normalized to cell number of T24 cells treated with 40 nM or 75 nM MG88 (SEQ ID No:1) for 3, 5, 8, and 10 days.

As shown in FIG. 3A, induction of expression of $p16^{ink4A}$ protein was detected after 5 days of treatment with either 40 nM or 75 nM of MG88, but not after treatment with MG208. Because MG88 has an antiproliferative effect, $p16^{ink4A}$ levels were normalized to cell number (FIG. 3B), Thus, induction of $p16^{ink4A}$ protein by MG88 was both dose-dependent and time dependent. $p16^{ink4A}$ was not detected in cells treated with either 40 nM or 75 nM of the mismatch control MG208 or lipofectin alone (FIG. 3A).

Figure 4:
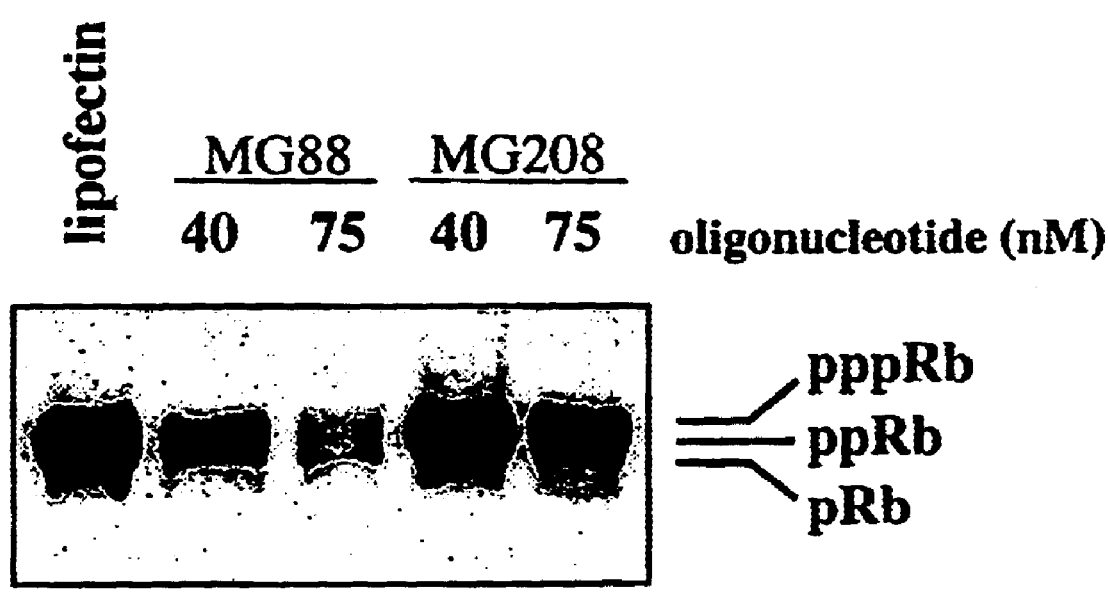
FIG. 4 is a representation of an autoradiograph of a Western blotting analysis of T24 cells treated with 40 nM or 75 nM of a representative non-limiting antisense oligonucleotide of the invention, MG88 (SEQ ID No:1), using an antibody recognizing all phosphorylated forms of Rb.

Moreover, reactivation of $p16^{ink4A}$ protein expression by MG88 also caused accumulation of hypophosphorylated pRb and inhibition of cell proliferation. $p16^{ink4A}$ regulation progression through the $G_1$ phase of the cell cycle by inhibiting cyclin-dependent kinase CDK4-mediated phosphorylation of pRB such that the hypophosphrylated form of Rb is associated with $G_1/G_0$ growth arrest (Serrano et al., supra). Cell lysates of T24 cells which were reactivated to express $p16^{ink4A}$ protein following transfection with MG88 were analyzed by Western blotting analysis for phosphorylated pRb showed a decrease in the amount of phosphorylated forms of pRb, thus increasing the relative abundance of the hypophosphorylated form of pRb (FIG. 4). These results demonstrate that high levels of DNA MeTase in T24 cells actively suppress $p16^{ink4A}$ gene expression and that restoration of $p16^{ink4A}$ expression functionality regulations downstream molecular targets, such as pRb.

Figure 5:
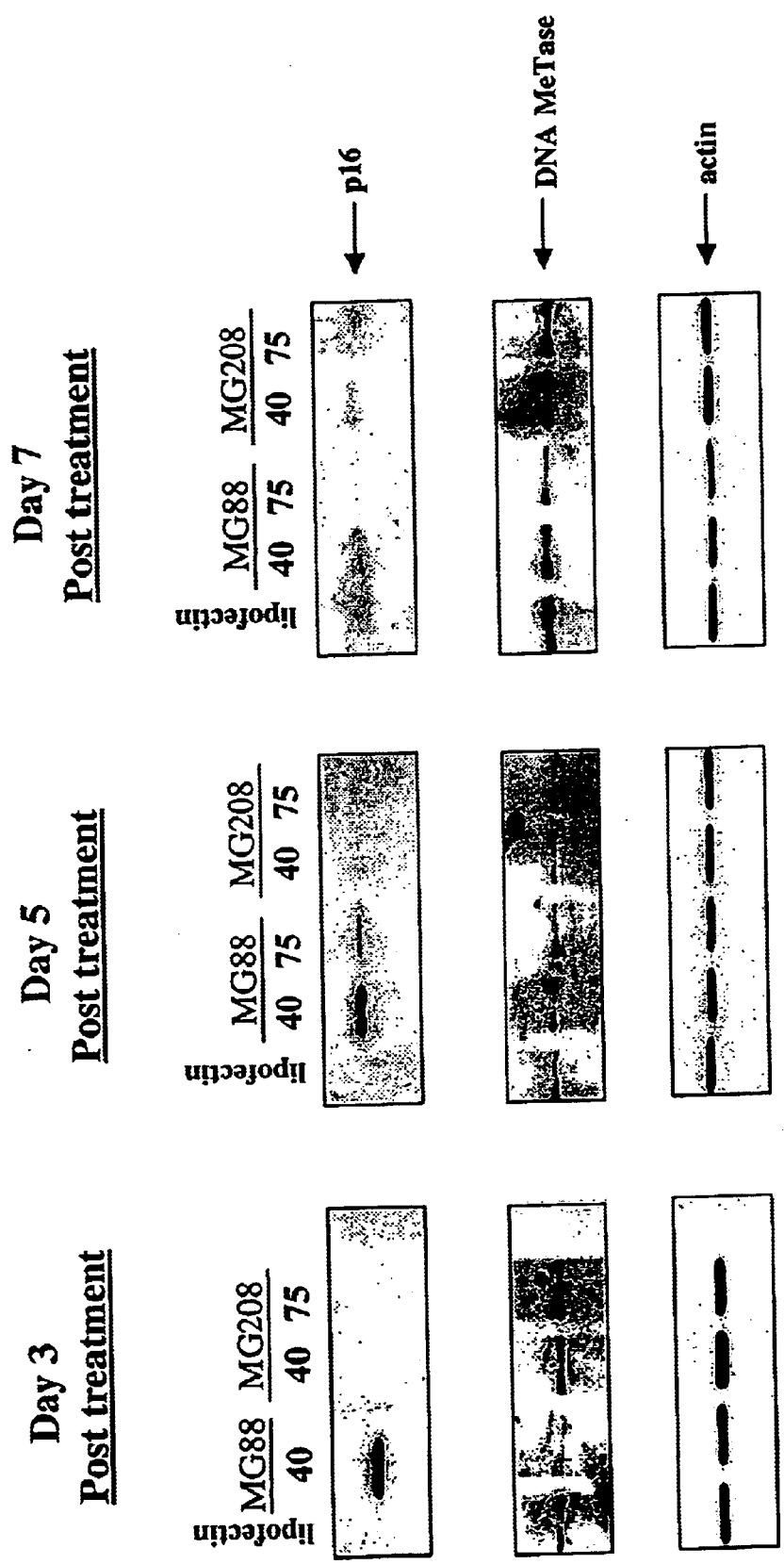
FIG. 5 is a representation of autoradiographs of a series of Western blotting analyses of T24 cell lysates prepared 3, 5, or 7 days after cessation of a 10 day treatment of the cells with lipofectin only 40 nM of MG88 (SEQ ID No:1), or 40 nM or 75 nM of control oligonucleotide MG208 (SEQ ID No:4), demonstrating that between 5–7 days post-treatment, DNA MeTase protein expression is restored and $p16^{ink4}$ protein expression is diminished.
Figure 6:
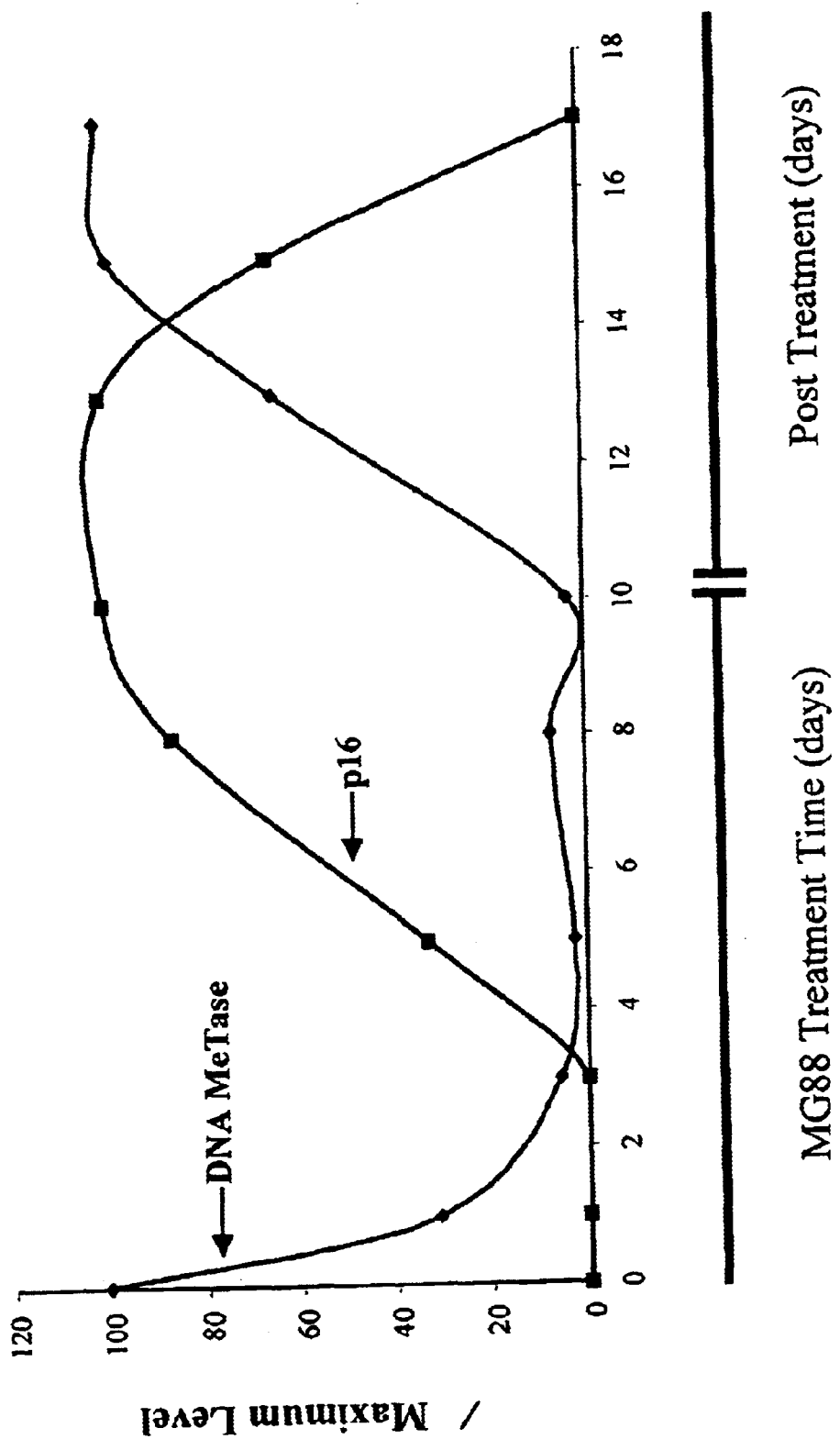
FIG. 6 is a graphic representation of the quantitation of DNA MeTase and $p16^{ink4}$ protein levels in T24 cells during ten days of treatment with MG88 (SEQ ID No:1) and 7 days (i.e., days 11–17) post-treatment periods, demonstrating the inverse relationship between p16 protein levels and DNA MeTase protein levels in these cells.

Next, to determine whether de novo methylation and silencing of the re-expressed $p16^{ink4A}$ gene occurred when DNA MeTase returned to normal levels, T24 cells were transfected for 10 consecutive days with either 40 or 75 nM or MG88 or MG208. Because transfection of the cells with 75 nM MG88 had a significant antiproliferative and cell death inducing effect, only cells treated with the lower dose (40 nM) of MG88 were used for the remainder of the experiment. Cell lysates of the T24 cells transfected for ten days were analyzed by Western blotting analysis for expression of DNA MeTase protein,$p16^{ink4A}$ protein, and actin protein (as a control for equal loading) 3, 5, and 7 days after MG88 transfection. As shown in FIG. 5, DNA MeTase protein levels increased in the absence of MG88 treatment and returned to control levels between days 5–7 post-treatment (middle panel). The level of $p16^{ink4A}$ protein decreased steadily over the post-treatment period until it was barely detectable at day 7 post-treatment (FIG. 5, upper panel). FIG. 6 shows the inverse relationship between DNA MeTase levels and $p16^{ink4A}$ protein levels during and after treatment with MG88. Interestingly, the loss of $p16^{ink4A}$ protein expression began at day 14 after DNA MeTase levels returned to near control levels. This lag suggests that elevated levels of DNA MeTase over several rounds of replication are required to methylate and inactivate $p16^{ink4A}$ gene expression. That the inactivation and de novo methylation of p16$^{ink4A}$ are coincident with elevated levels of the DNA MeTase (Dnmt1) suggests that it may contribute to de novo methylation activity itself.

To identify changes in the methylation status of the p16$^{ink4A}$ promoter induced by MG88 treatment, methylation specific PCR (MSP) and bisulfite genomic sequencing was performed as previously described (Caldas et al. (1994) Nat. Gen. 8: 27–32; Frommer et al. (1991) Proc. Nat. Acad. Sci. USA 89: 1827–2831). MSP of the p16$^{ink4A}$ promoter was performed on T24 cells treated with 40 µM or 75 µM of MG88 or MG208 for 3, 5, 9, or 10 days. Briefly, the Oncor p16 detection system was used (commercially available from Oncor, Gaithersburg, Md.). PCR was performed in a total volume of 25 µl under the following conditions: 100 ng bisulfate-treated DNA (Oncor),10 mM Tris-HCl, pH 8.3, 50 nM KCl, 1.5 mM MgCl$_2$, 250 µM dNTPs, 80 ng of each of the following primers (5'-GTAGGTGGGGAGGAGTTTAGTTT-3' sense (SEQ ID NO: 79) and 5'-TCTAATAACCAACCAACCCCTAA-3' antisense (SEQ ID NO: 80)) and 1 unit of AmpliTaq Gold (Perkin-Elmer). The denaturation cycle was 95° C. for 12 min followed by 35 cycles at 95° C. for 45 seconds, 60° C. for 45 seconds, and 72° C. for 60 seconds, and an elongation cycle of 72° C. for 10 minutes. the PCR product (5 µl) was analyzed on a 2% agarose gel. The unmethylated (U) and demethylated (D) primers (commercially available from Oncor) were used at the same conditions as the specific primers. PCR products were subcloned into PCR2.1 (commercially available form Invitrogen, Carlsbad, Calif.), and sequenced to determine demethylation of CpG sites in the p16 proximal promoter.

Figure 7:
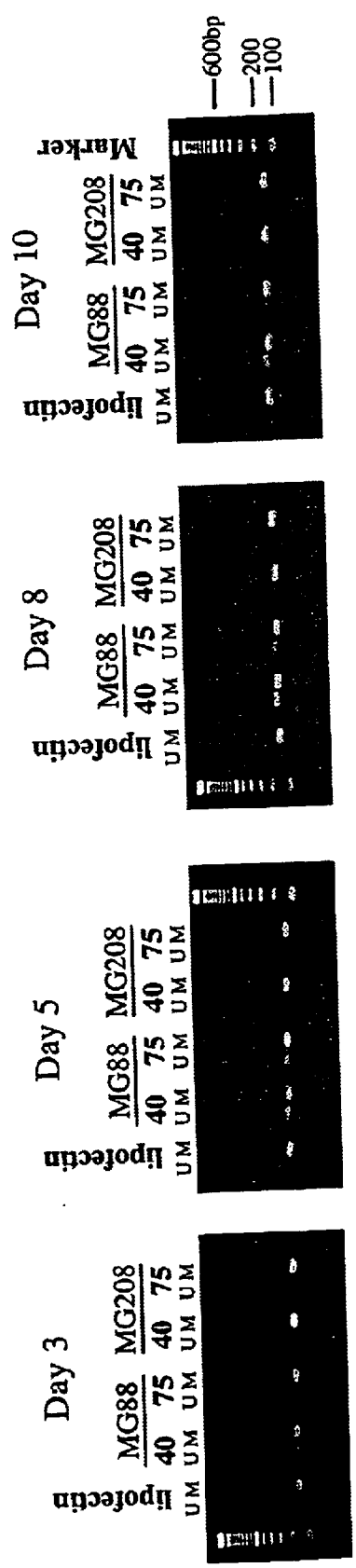
FIG. 7 is a representation of a series photographs of showing the methylation-specific PCR (MSP) products resolved on 2% agarose gels of the $p16^{ink4}$ gene promoter from T24 cells treated with 40 or 75 nM of MG88 (SEQ ID No:1) or MG208 (SEQ ID No:4) of 3, 5, 8, or 10 days using PCR primers specific for methylated $p16^{ink4}$ (M lanes) or unmethylated $p16^{ink4}$ (U lanes), demonstrating that demethylation of $p16^{ink4}$ occurred only in MG88 treated cells after at least 3 days of treatment
Figure 8:
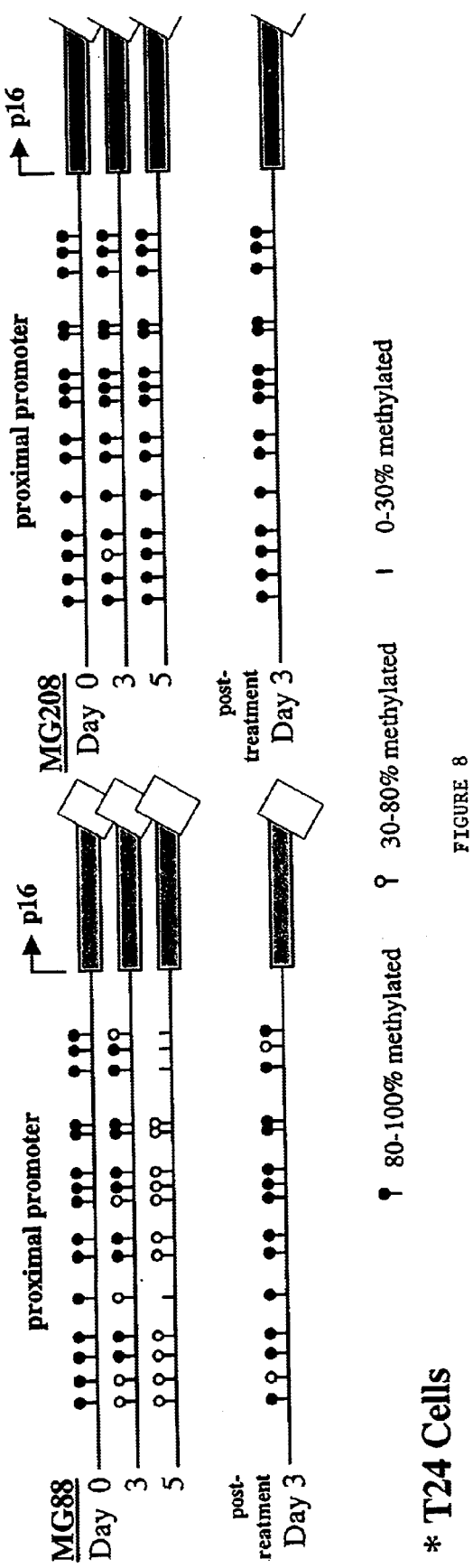
FIG. 8 is a diagrammatic representation of the $p16^{ink4}$ proximal promoter from T24 cells showing the methylation patterns after 0, 3, or 5 days of treatment of the cells with MG88 (SEQ ID No:1) (left) or control oligonucleotide MG208 (SEQ ID No:4) (right), demonstrating that reduced methylation occurred only with MG88 treatment. Day 3 post-treatment methylation patterns are shown at the bottom of the figure.

As shown in FIG. 7, MSP analysis with PCR primers specific for methylated p16$^{ink4A}$ (M) or unmethylated p16$^{ink4A}$ (U) revealed that demethylation of the p16$^{ink4A}$ promoter region occurred as early as day 3 of MG88 treatment. Treatment with MG208 or lipofectin alone had no effect on methylation of the p16$^{ink4A}$ gene (FIG. 7). FIG. 8 shows that by employing bisulfite genomic sequencing on days 0, 3, and 5 of treatment with MG88 or MG208, fifteen CpG sites within the p16$^{ink4A}$ promote were found to be methylated in untreated T24 cells. Inhibition of the DNA MeTase by MG88 led to demethylation of 5 of fifteen CpG sites by day 3 and demethylation at all 15 CpG sites by day 5 of treatment, whereas treatment with the control MG208 had no effect on p16$^{ink4A}$ methylation status (FIG. 8). Three days after cessation of MG88 treatment the p16$^{ink4A}$ promoter shows significant re-methylation at 13 of 15 sites reflecting either de novo methylation of these sites or a rapid expansion of a less affected population (FIG. 8, bottom panel).

Figure 9A:
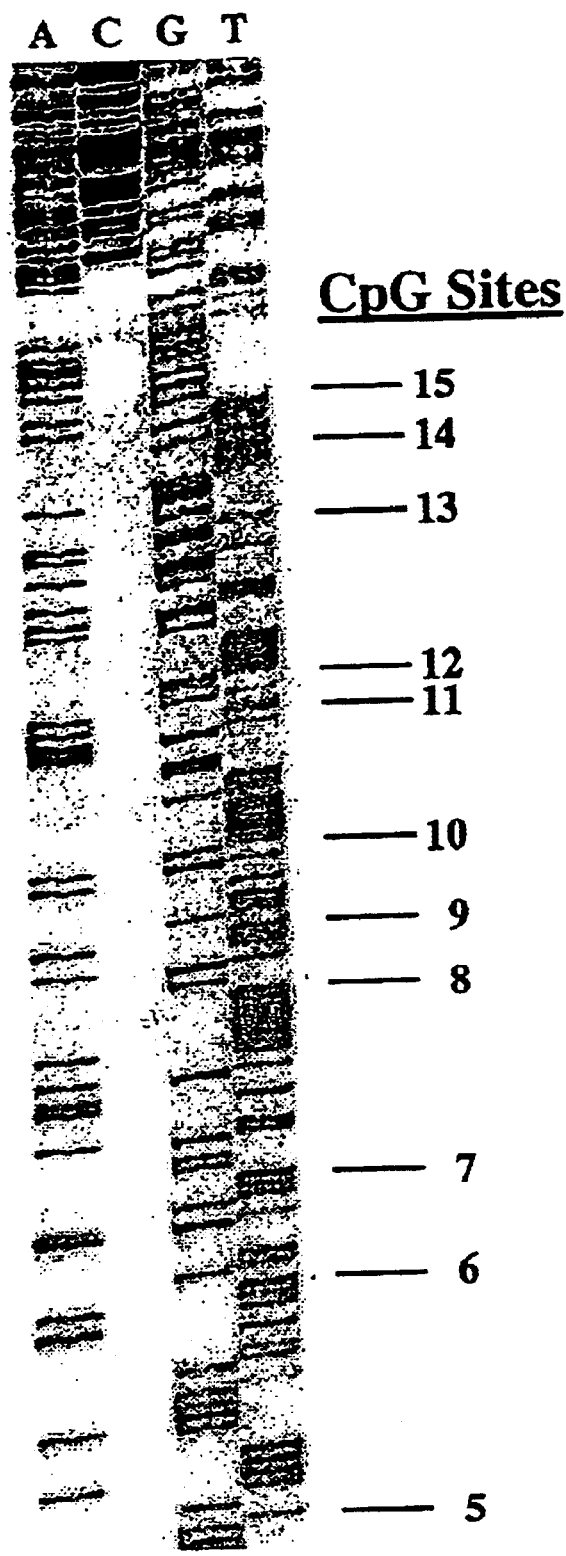
FIG. 9A is a representation of a photograph of the results of bisulfite sequencing of the $p16^{ink4}$ gene promoter in $p16^{ink4}$-expressing clone MG88(SEQ ID No:1) C4–5 30 days following cessation of a 5 day treatment with 75 nM MG88, demonstrating that all CpG sites evaluated were not methylated in this clone even after 30 days in culture post-MG88 treatment.
Figure 9B:
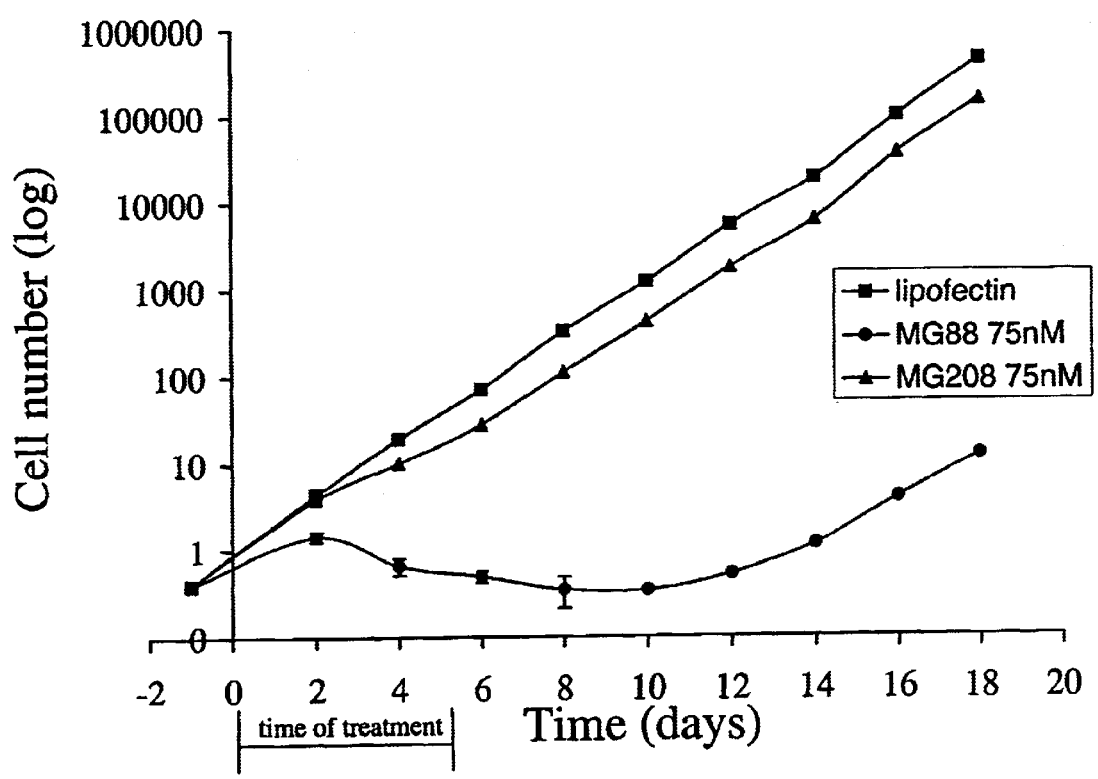
FIG. 9B is a graphic representation showing a growth curve of T24 cells during treatment (days 0–5) and post-treatment (days 6–18) with lipofectin only (squares), 75 nM MG88 (SEQ ID No:1), a non-limiting representative antisense oligonucleotide of the invention (circles), or 75 nM or control oligonucleotide, MG208 (SEQ ID No:4) triangles), demonstrating the anti-proliferative effect of MG88.

To study the effect of specific inhibition of DNA MeTase on cell growth, cellular proliferation rates were monitored both during the treatment and post treatment periods to determine the duration of the effect. T24 cells were treated for 0–5 days with lipofectin only, 75 nM MG88 or 75 nM MG208. During and following treatment, cells were counted. As can be seen in FIG. 9B, during the course of treatment, MG88 dramatically inhibited cell proliferation, whereas treatment of cells with the control MG208 caused only minimal growth inhibition relative to lipofectin treated cells. Inhibition of cell proliferation persisted for approximately one week post-treatment, consistent with the finding that p16$^{ink4A}$ expression was maintained until 7 days after the last dose of MG88 (see FIGS. 5 and 6). To determine whether the transient re-expression of p16$^{ink4A}$ and growth-inhibitory effects induced by short term treatment with MG88 were due to the expansion of a less affected (less demethylated) population of cells within the treated population, or to rapid inactivation of p16$^{ink4A}$ after MG88 withdrawal, single cell clones were isolated after treatment. Several MG88 clones were, in fact, p16$^{ink4A}$ negative, confirming that the MG88 treatment produced a mixed population of p16$^{ink4A}$ positive and negative cells. Methylation analysis by bisulfite sequencing of the p16$^{ink4A}$ promoter of one of the MG88 positive clones, done 4–5, thirty days following treatment with a five day treatment with MG88 revealed that the p16$^{ink4A}$ promoter region was completely non methylated at all CpG sites evaluated (FIG. 9A), demonstrating that even short term (5 day) inhibition of the DNA MeTase by MG88 could induce prolonged re-expression of a silenced tumor suppressor gene. As shown in FIGS. 9B and 9C, done MG88 C4–5 initially grew slowly following a five day treatment with MG88 as compared to lipofectin clone C-5 (treated for 5 days with lipofectin) and MG208 C2–4 (treated for 5 days with MG208); however between days 40 and 45 days post treatment, the growth rate of MG88 C4–5 cells increased dramatically (FIG. 9C). Determination of p16$^{ink4A}$ protein levels in MG88 C4–5 cells revealed a significant decrease at Day 49 (FIG. 9C, inserted Western blotting analysis). Loss of p16$^{ink4A}$ expression after prolonged culture in the absence of MG88 treatment suggests that the DNA MeTase targeted (thought to encode maintenance DNA MeTase activity) may have de novo methyltransferase activity and over time can methylate and inactivate previously unmethylated actively expressing genes.

Example 3

Inhibition of MeTase Rapidly Induces p21$^{WAF1}$

Figure 10A:
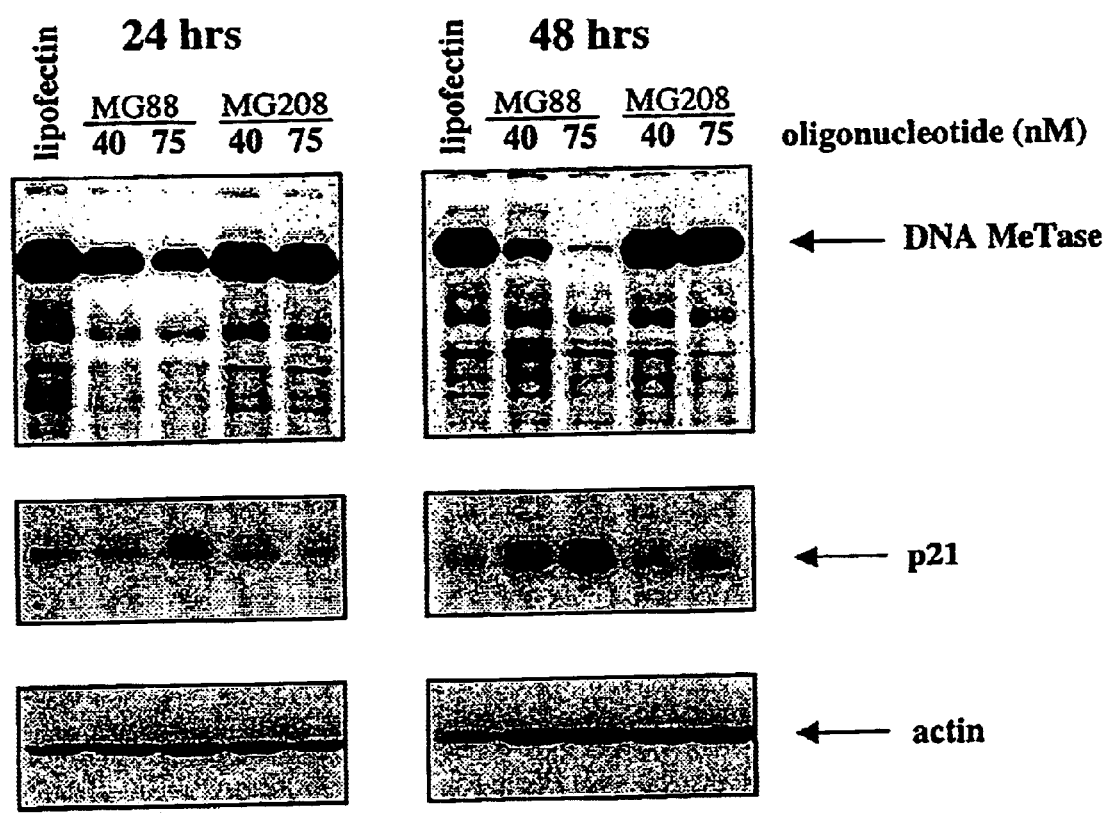
FIG. 10A is a representation of autoradiographs of Western blotting analyses of $p21^{WAF1}$, MeTase, and α-actin protein levels in T24 cells treated for 24 hours (left panels) or 48 hours (right panels) with lipofectin only, or 40 nM or 75 nM of MG88 or MG208, demonstrating that $p21^{WAF1}$ protein expression is induced by inhibition of MeTase expression.

Another member of the cyclin-dependent kinase inhibitor (CDKI) family, p21$^{WAF1}$, inhibits a wide range of cyclin/CDK complexes involved in G$_1$ and S phase progression (Tam et al. (1994) Cancer Res. 54: 5816–5820; Baghdassarian and French (1996) Hematol. Cell Ther. 88: 313–323; Gotz et al. (1996) Oncogene 13: 391–398). To investigate whether DNA MeTase and p21$^{WAF1}$ protein levels are linked by a regulatory pathway, p21$^{WAF1}$ protein levels were measured in T24 cells in which DNA MeTase levels had been incrementally reduced by MG88 treatment. To do this, DNA MeTase, p21$^{WAF1}$, and α-actin protein levels were measured by Western blotting analysis in T24 cells that had been treated for either 24 hours (i.e., one 4 hour transfection time) or 48 hours (i.e., two 5 hour transfections 24 hours apart) with either 40 nM or 75 nM of either MG88 or MG208. As shown in FIG. 10A, p21$^{WAF1}$ increased directly with the reduction in DNA MeTase, while neither lipofectin nor MG208 had an effect on either DNA MeTase or p21$^{WAF1}$ levels.

Figure 10B:
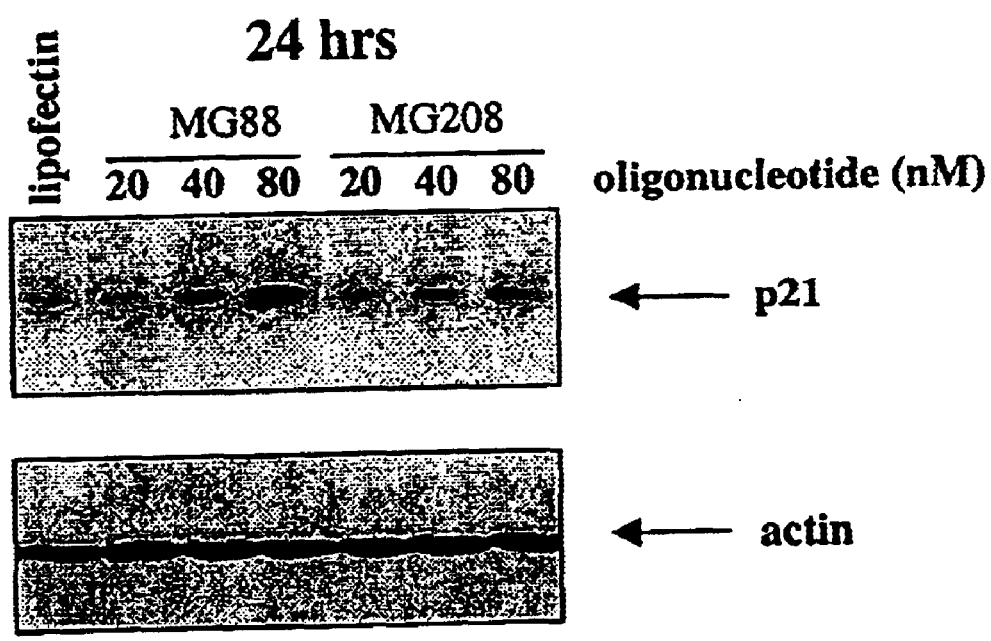
FIG. 10B is a representation of autoradiographs of Western blotting analyses showing the dose-response of $p21^{WAF1}$ protein levels in T24 cells treated for 24 hours with 20 nM, 40 nM, or 80 nM of MG88(SEQ ID No:1) MG208 ( SEQ ID No:4). Actin protein levels are shown as a control for protein loading.

T24 cells were also treated for 24 hours (i.e., four hour transfection) with lipofectin only, or lipofectin plus 20, 40, or 80 nM of MG88 or MG208. After treatment, cell lysates were prepared and analyzed by Western blotting analysis with α-actin-specific antibody or p21-specific antibody. As shown in FIG. 10B, DNA MeTase inhibition induced p21$^{WAF1}$ in a dose dependent fashion as early as 24 hours after MG88 treatment, consistent with a role for p21$^{WAF1}$ in the antiproliferation effect observed with MG88 treatment (see, e.g., FIGS. 3B and 9B).

Figure 11:
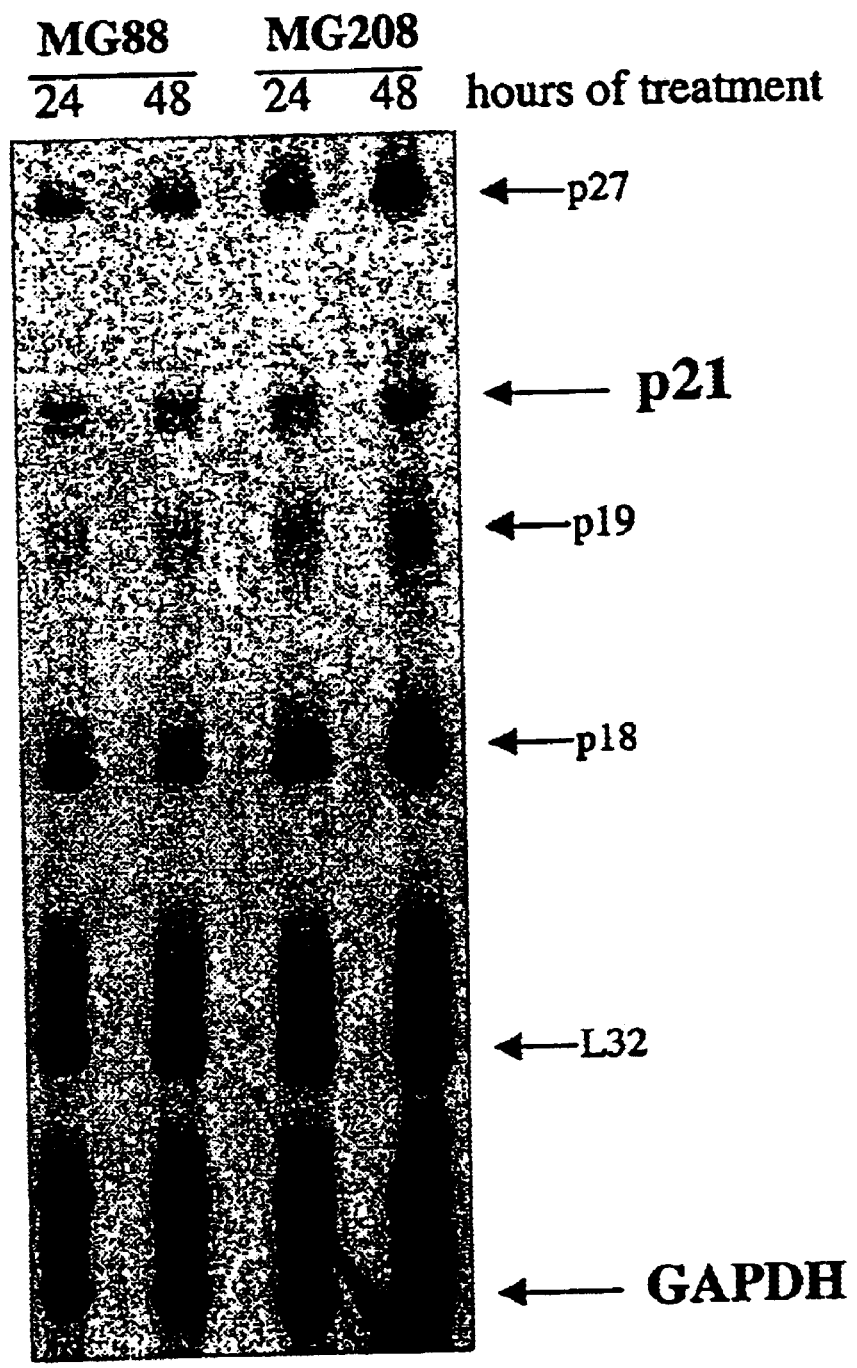
FIG. 11 is a representative of an autoradiograph showing a Northern blotting analysis of RNA from T24 cells treated for 24 or 48 hours with MG88 (SEQ ID No:1) or MG208 (SEQ ID No:4).

Next, to determine if p21$^{WAF1}$ was induced at the transcriptional level, RNase protection assay were performed on cells treated with 40 nM of either MG88 or MG208 for either 24 or 48 hours. Total cellular RNA was isolated from the cells and analysed for p21 mRNA, p27 mRNA, and p18 mRNA using the human cell cycle-2 (hcc-2) multiprobe RNase protection kit commercially available from PharMingen, San Diego, Calif.). RNA loading was determined to be equal using the signals from two housekeeping genes, L32 and GAPDH. As shown in FIG. 11, no increase in $p21^{WAF1}$ mRNA was observed in response to treatment with MG88, suggesting that post-translational regulation of $p21^{WAF1}$ protein is involved.

This example demonstrates that a functional antagonism between DNA MeTase and $p21^{WAF1}$ on cellular proliferation exists. Thus, high levels of DNA MeTase found in transformed cells may regulate proliferation by reducing cellular $p21^{WAF1}$ levels. High levels of DNA MeTase in transformed cell may also compete directly for the downstream target PCNA, since human DNA MeTase can compete with $p21^{WAF1}$ for PCNA binding (Chuang et al. (1997) Science 277: 1996–2000).

Example 4

Synergistic Reactivation of the p16 Tumor Suppressor

The purpose of this example is to illustrate the ability of the methods and compositions of the invention to restore the expression of genes which are inactivated by methylation such as, for example, the p16 tumor suppressor as illustrated herein. For this purpose, one day before transfection, T24 cells (ATCC No. HTB-4) were plated onto 10 cm plates at $4 \times 10^5$ cells/dish. At the time of transfection, cells were washed with phosphate buffered saline (PBS) and 5 ml of optimem media (Gibco-BRL) containing 6.25 µl/ml lipofectin transfection reagent (Gibco-BRL) was added. The oligonucleotides used were: MG88 having the sequence 5'-AAG CAT GAG CAC CGT TCUCC-3' (SEQ ID NO:1) (this oligonucleotide is targeted to the DNA MeTase mRNA 5'UTR at nucleotides 532 to 513) and MG98 having the sequence 5'-UUC ATG TCA GCC AAG GCC AC-3' (SEQ ID NO:2) (this oligonucleotide is targeted to the DNA MeTase mRNA 3'UTR at nucleotides 5218 to 5199). Negative controls used were: MG207 having the sequence 5'-UUA ATG TAA CCT AAG GUC AA-3' (SEQ ID NO:3) and MG208 having the sequence 5'-AAC GAT CAG GAC CCT TGU CC-3' (SEQ ID NO:4). These oligonucleotides were chemically modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of each oligonucleotide consisted of a phosphorothioate linkage between adjoining nucleotides. The oligonucleotides were diluted to the desired concentration from a 0.1 mM stock solution in the transfection media. After a four-hour incubation at 37° C. in a 5% $CO_2$ incubator, the plates were washed with PBS and 10 ml of fresh cell culture media was added. Following an additional two-hour incubation at 37° C., freshly prepared 5-aza-2'-deoxycytidine was added to the tissue culture medium. Cells were transfected for a total of three days and split every other day to ensure optimal transfection conditions. At the indicated time points, cells were harvested by trypsinization and pelleted by centrifugation at 1100 rpm and 4° C. for five minutes. The cell pellet was resuspended in PBS and counted on a Coulter Particle Counter to determine the total cell number. Following a second centrifugation, the PBS was aspirated from the cell pellet and the pellet was frozen at 70° C.

Figure 12:
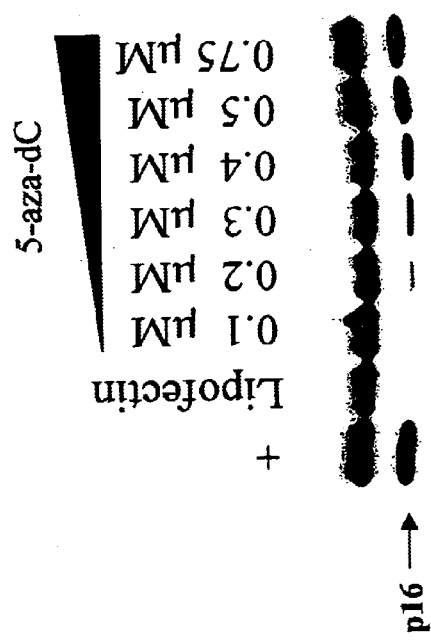
FIG. 12 is a representation of an autoradiograph of a Western blotting analysis showing the reactivation of p16 expression in T24 cells following treatment for three days with increasing concentrations of a representative, non-limiting DNA MeTase protein effector, 5-aza-dC.
Figure 13:
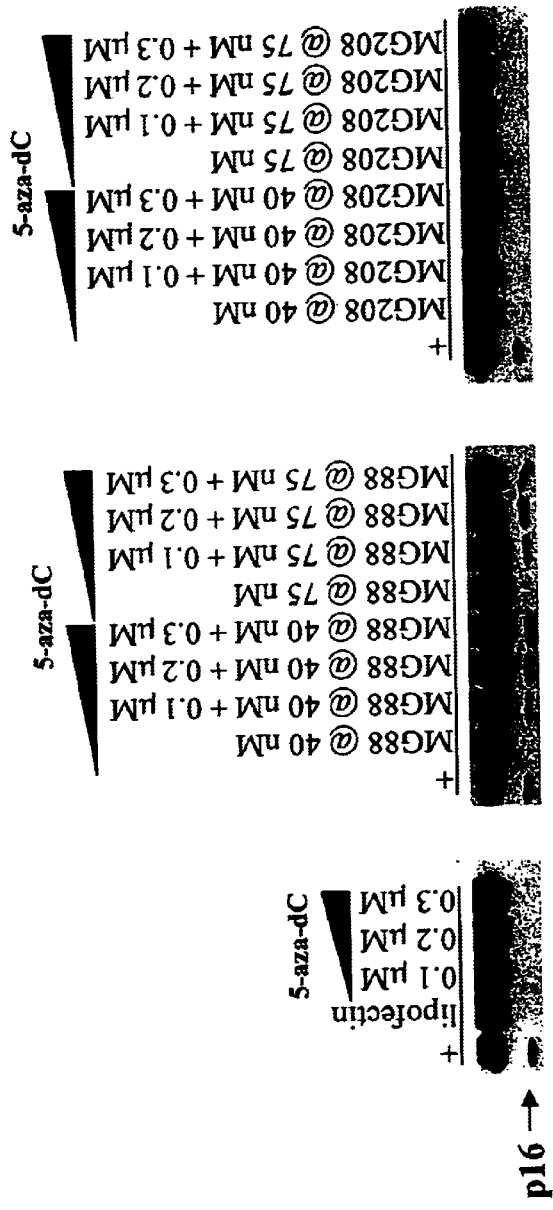
FIG. 13 is a representation of an autoradiograph of the Western blot analysis showing the synergistic reactivation of p16 expression in T24 cells following treatment for three days with a representative, nonlimiting, synthetic antisense oligonucleotide (MG88) (SEQ ID No:1) and/or a representative non-limiting DNA MeTase protein effector (5-aza-dC) according to the invention; the three panels show varying combinations and concentrations of representative antisense oligonucleotides and DNA MeTase protein effectors according to the invention.

Cell pellets were resuspended in 200 µl of cell lysis buffer (25 mM Tris pH 7.5, 5 mM EDTA, 0.5% sodium deoxycholate, and 1% tritonx100) supplemented with protease inhibitors: aprotinin, leupeptin, pepstatin, TLCK, and PMSF. The lysed cells were incubated on ice for 10 minutes and cell particulate matter was removed by centrifugation at 10,000 rpm for 10 minutes at 4° C. The protein concentration for each sample was determined using the Bio Rad Protein Assay and 600 µg of protein was used for each immunoprecipitation. Anti-p16 antibody (Santa Cruz) was added, 2.5 µg/ml, and each sample was incubated at 4° C. for one hour on a rotary shaker. Each sample was incubated for an additional 45 minutes at 4° C. after the addition of 20 µl of equilibrated Protein G and washed three times with lysis buffer containing no protease inhibitors. The Protein G pellet was resuspended in 15 µl of 2×gel loading buffer, containing β-mercaptoethanol and incubated at room temperature for 10 minutes. After boiling for five minutes, samples were separated by gel electrophoresis on a 4–20% polyacrylamide gradient gel and blotted onto PVDF membrane (Amersham Life Sciences, Cleveland, Ohio). Each membrane was incubated overnight 1×TBST wash buffer (10 mM Tris pH 8.0, 150 mM NaCl, 0.05% Tween 20) supplemented with 5% milk. The membranes were incubated with mouse anti-human p16 antibody (Pharmingen Mississauga, Ontario), 1 µg/ml, for sixty minutes at room temperature. Following three washes in 1×TBST, and a one-hour incubation with the secondary antibody, goat anti-mouse IgG, membranes were washed two times in 1×TBST and two times in 1×TBS, and chemiluminescence was performed. FIG. 12 shows the Western blot analysis of T24 cells treated with various concentrations of 5-aza-dC from 0.1 µM to 0.75 µM, showing reactivation of p16 in the range of 0.3 µM to 0.75 µM 5-aza-dC. FIG. 13 shows the Western blot analysis of T24 cells treated by the method of the invention using antisense oligonucleotide MG88 and 5-aza-dC. A comparison of the bands presence and intensity in FIG. 13 shows that reactivation of the p16 gene is successfully achieved using a combination of the oligonucleotide and the protein effector according to the invention at concentrations at which neither the oligonucleotide nor the protein effector used alone would be effective (e.g., at as low as 40 nM oligonucleotide MG88 and 0.1 µM 5-aza-dC).

Figure 14:
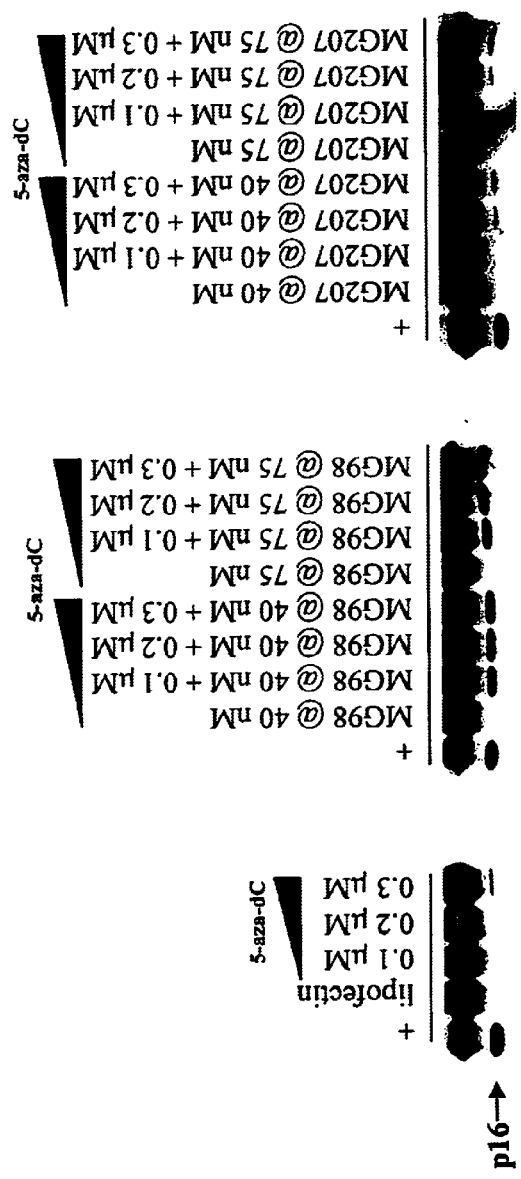
FIG. 14 is a representation of an autoradiograph of the Western blot analysis showing the synergistic reactivation of p16 expression in T24 cells following treatment for three days with a representative, nonlimiting, synthetic antisense oligonucleotide (MG98) (SEQ ID No:2) and/or representative non-limiting DNA MeTase protein effector (5-aza-dC) according to the invention; the three panels show varying combinations and concentrations of representative oligonucleotides and DNA MeTase protein effectors according to the invention.

FIG. 14 shows the Western blot analysis of T24 cells treated by the method of the invention using antisense oligonucleotide MG98 and 5-aza-dC. Once again, a comparison of the bands presence and intensity in FIG. 14 shows that reactivation of the p16 gene is successfully achieved using a combination of the oligonucleotide and the protein effector according to the invention at concentrations at which neither the oligonucleotide nor the protein effector used alone would be effective (e.g., at as low as 40 nM oligonucleotide MG98 and 0.1 µM 5-aza-dC).

The Western blotting analysis in FIG. 14 was subjected to densitometric analysis and normalized to the level of p16 expression in HeLa cells. The results of the densitometric analysis is shown in Table 5.

TABLE 5

| Treatment of T24 cells | Percentage of HeLa Cell Control |
| --- | --- |
| (HeLa cell control) | 100 |
| Lipofectin only | 6 |
| Lipofectin plus 0.1 µM 5-aza-dC | 11 |
| 40 nM MG207 | 1 |
| 40 nM MG207 plus 0.1 µM 5-aza-dC | 3 |

TABLE 5-continued

| Treatment of T24 cells | Percentage of HeLa Cell Control |
| --- | --- |
| 40 nM MG98 | 4 |
| 40 nM MG98 plus 0.1 µM 5-aza-dC | 79 |

As Table 5 shows, the combination of both MG98 plus 5-aza-dC has a much greater effect on p16 reactivation in T24 cells as compared to either MG98 or 5-aza-dC alone.

Figure 15:
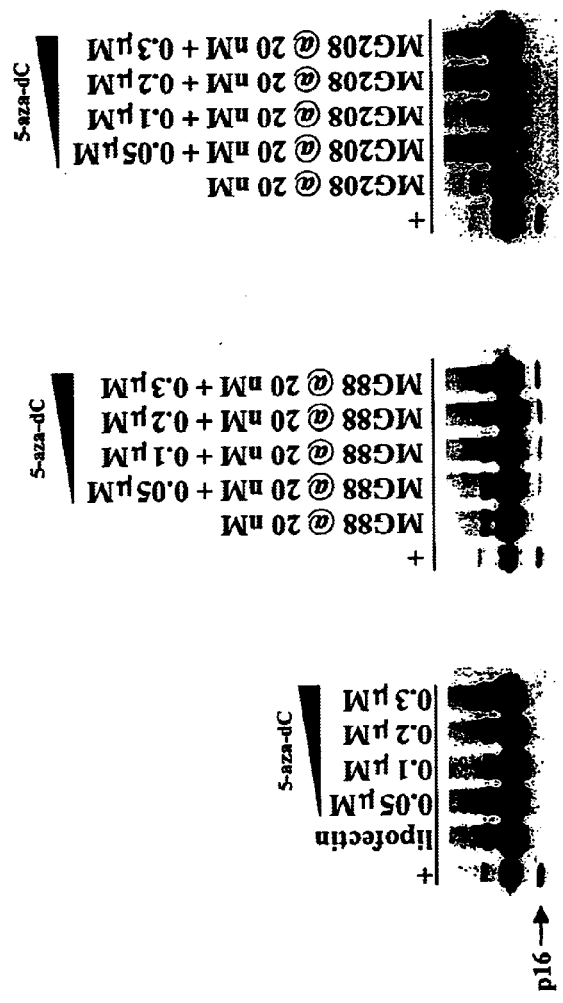
FIG. 15 is a representation of an autoradiograph of the Western blot analysis showing the synergistic reactivation of p16 expression in T24 cells following treatment for three days with a representative, nonlimiting, synthetic oligonucleotide (MG88) (SEQ ID No:1) and/or a representative non-limiting DNA MeTase protein effector (5-aza-dC) according to the invention at low concentrations; the three panels show varying combinations and concentrations of representative oligonucleotides and DNA MeTase protein effectors according to the invention.

FIG. 15 shows the Western blot analysis T24 cells treated by the method of the invention using antisense oligonucleotide MG88 and 5-aza-dC using even lower concentrations of oligonucleotide MG88. A comparison of the bands presence and intensity in FIG. 15 shows that reactivation of the p16 gene is successfully achieved using a combination of the oligonucleotide and the protein effector according to the invention at concentrations at which neither the oligonucleotide nor the protein effector used alone would be effective (e.g., at as low as 20 nM oligonucleotide MG88 and 0.2 µM 5-aza-dC).

Example 5

Synergistic Inhibition of Neoplastic cell Growth in Vitro

To illustrate the ability of the methods and composition of the invention to inhibit DNA MeTase and to inhibit neoplastic cell growth in a synergistic fashion, T24 bladder carcinoma cells (ATCC No. HTB-4; American Type Culture Collection, Manassas, Va.) or A549 human lung carcinoma cells (ATCC No. CCL-185) were treated according to the invention and their growth pattern observed and compared to that of untreated control cells. For this purpose, one day before transfection, cells were plated onto 10 cm plates at $4 \times 10^5$ cells/dish. At the time of transfection, cells were washed with phosphate buffered saline (PBS) and 5 ml of Opti-MEM media (Gibco-BRL, Mississauga, Ontario) containing 6.25 µl/ml lipofectin transfection reagent (Gibco-BRL Mississauga, Ontario) was added. The oligonucleotides used were: MG98 having the sequence 5'-UUC ATG TCA GCC AAG GCC AC-3' (SEQ ID NO:2) (this oligonucleotide is targeted to the DNA MeTase mRNA 3'UTR at nucleotides 5218 to 5199) and negative control MG207 having the sequence 5'-UUA ATG TAA CCT AAG GUC AA-3' (SEQ ID NO:3). These oligonucleotides were chemically modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of each oligonucleotide consisted of a phosphorothioate linkage between adjoining nucleotides.

Figure 16:
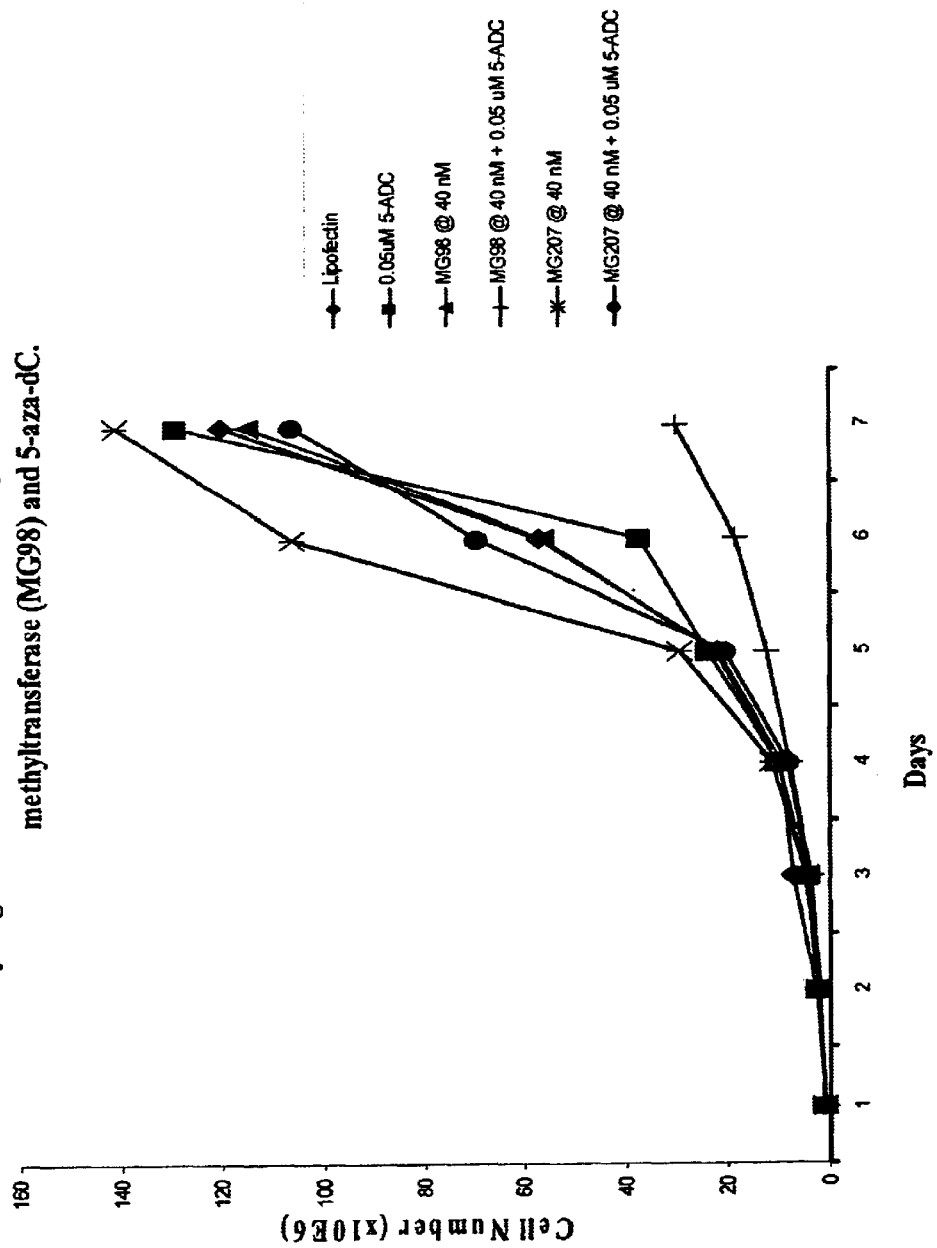
FIG. 16 is a graphic representation showing the ability of a representative, nonlimiting, synthetic antisense oligonucleotide (MG98) (SEQ ID No:2) and of a representative, nonlimiting, DNA MeTase protein effector (5-aza-dC) according to the invention to inhibit T24 human bladder cancer cell growth in a synergistic fashion resulting in an increased inhibitory effect as compared to that observed using either only the antisense oligonucleotides or only the DNA MeTase protein effectors.
Figure 17:
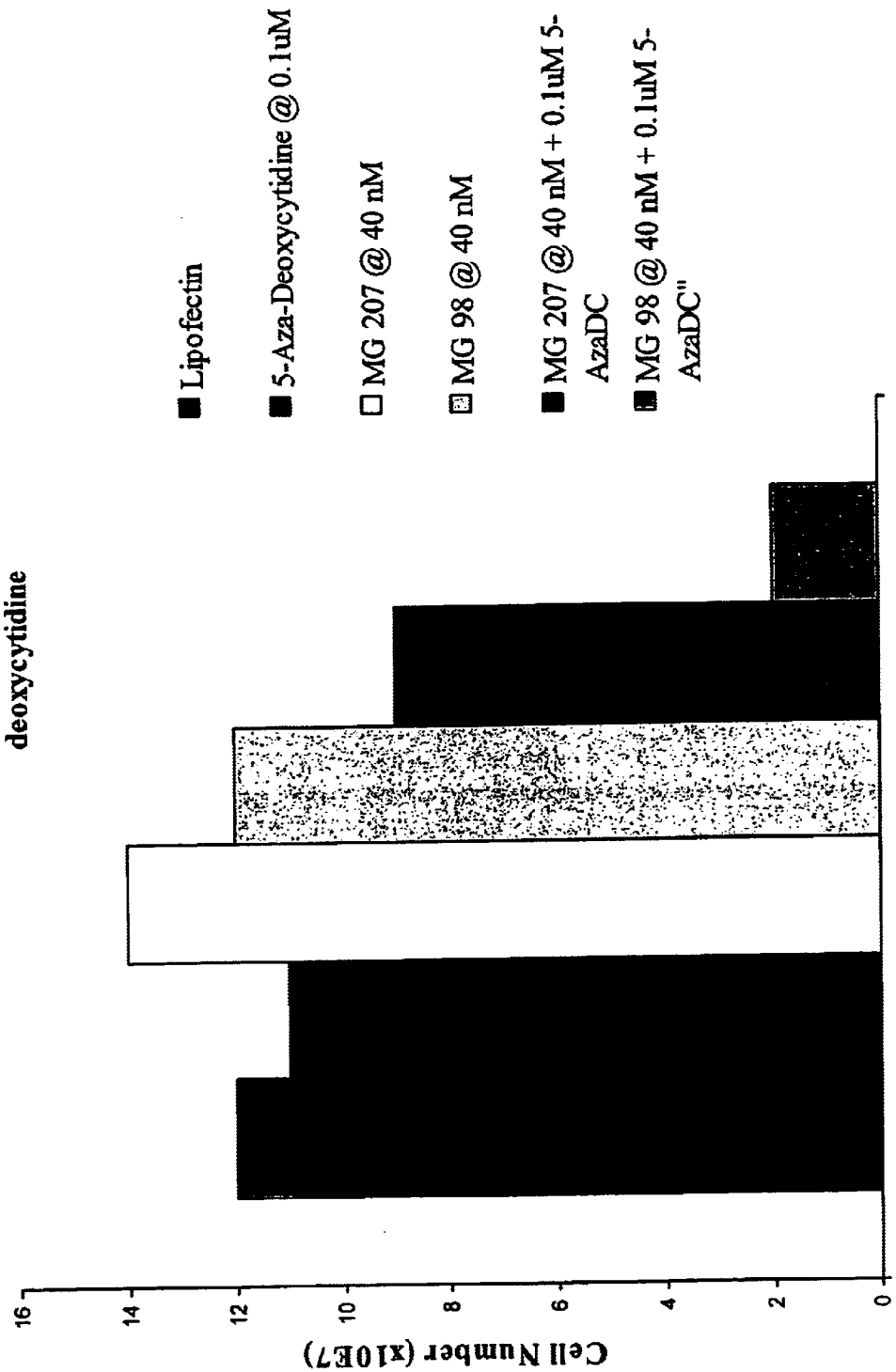
FIG. 17 is a graphic representation showing the synergistic inhibition of T24 human bladder cancer cell growth after treatment for seven days with lipofectin only (first bar from the left); 1 µM of a representative, nonlimiting, DNA MeTase protein effector, 5-aza-dC (second bar from the left); 40 nM of control synthetic oligonucleotide MG207 (SEQ ID No:3) (third from the left); 40 nM of a representative nonlimiting synthetic MeTase antisense oligonucleotide, MG98 (SEQ ID No:2) (fourth bar from the left); MG207 plus 5aza-dC (fifth bar from the left); or MG98 plus 5-aza-dC (sixth bar from the left).
Figure 18:
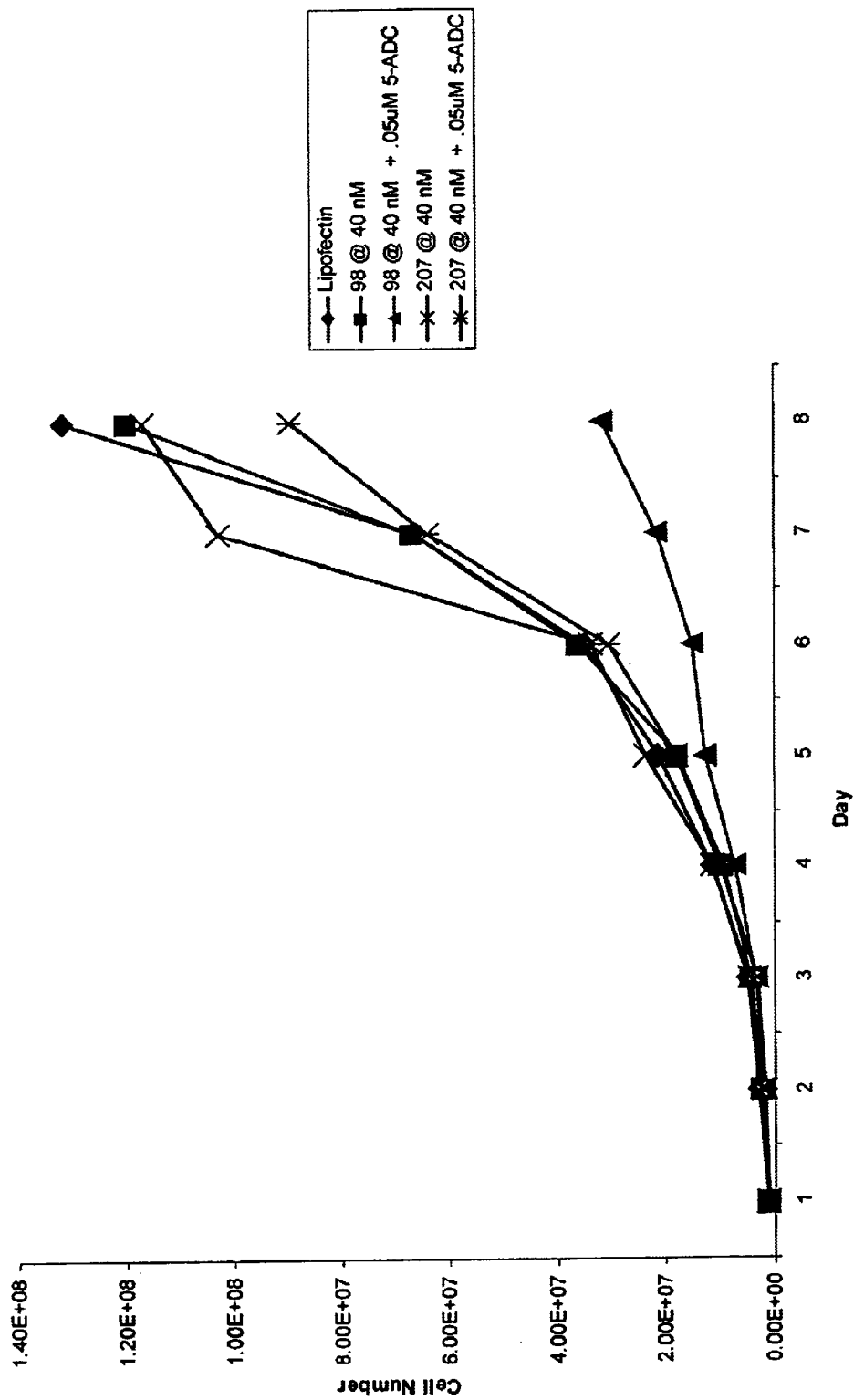
FIG. 18 is a graphic representation showing the ability of a representative, nonlimiting, synthetic oligonucleotide (MG98) (SEQ ID NO:2) and of a representative, nonlimiting, DNA MeTase protein effector (5-aza-dC) according to the invention to inhibit A549 human non-small cell lung cancer cell growth in a synergistic fashion resulting in an increased inhibitory effect as compared to that observed using either only the oligonucleotides or only the DNA MeTase protein effectors.

The oligonucleotides were diluted to the desired concentration from a 0.1 mM stock solution in the transfection media. After a four-hour incubation at 37° C. in a 5% CO$_2$ incubator, the plates were washed with PBS and 10 ml of fresh cell culture media was added. Following an additional two-hour incubation at 37° C., freshly prepared 5-aza-2'-deoxycytidine was added to the tissue culture medium. Cells were transfected for a total of three days and split every other day to ensure optimal transfection conditions. At the indicated time points, cells were harvested by trypsinization and pelleted by centrifugation at 1100 rpm and 4° C. for five minutes. The cell pellet was resuspended in PBS and counted on a Coulter Particle Counter to determine the total cell number. Following a second centrifugation, the PBS was aspirated from the cell pellet and the pellet was frozen at 70° C. Treated and untreated cells were analyzed by counting the cells according to standard methodologies. The results of representative experiments are shown in FIGS. 16, 17, and 18. FIG. 16 shows a growth curve of T24 cells that had been treated for 1–7 days with lipofectin only (diamond); 0.05 µM 5-aza-dC (square); 40 nM MG98 (triangle); 0.05 µM 5-aza-dC plus 40 nM MG98 (cross); 40 nM MG207 (star); or 0.05 µM 5-aza-dC plus 40 nM MG207 (circle). FIG. 17 shows the number of T24 cells remaining after the cells had been treated for seven days with lipofectin only, 0.1 µM 5-aza-dC, 40 nM MG207, 40 nM MG98, 0.1 µM 5aza-dC plus 40 nM MG207, or 0.1 µM 5-aza-dC plus 40 nM MG98. FIG. 18 shows a growth curve of A549 cells that had been treated for 1–7 days with lipofectin only (diamond); 40 nM MG98 (square); 0.05 µM 5-aza-dC plus 40 nM MG98 (triangle); 40 nM MG207 (X); or 0.05 µM 5-aza-dC plus 40 nM MG207 (star). These results show that the oligonucleotides and protein effectors according to the methods of the invention are capable of inhibiting MeTase enzymatic activity and neoplastic cell growth in a synergistic fashion resulting in an increased inhibitory effect as compared to that observed using either only the oligonucleotides or only the protein effectors. The results therefore attest to the ability of the invention to inhibit DNA MeTase using effective synergistic amounts of the antisense oligonucleotide and/or of the protein effector according to the invention.

Example 6

Synergistic Effect on Neoplastic Cells In Vivo

Figure 19:
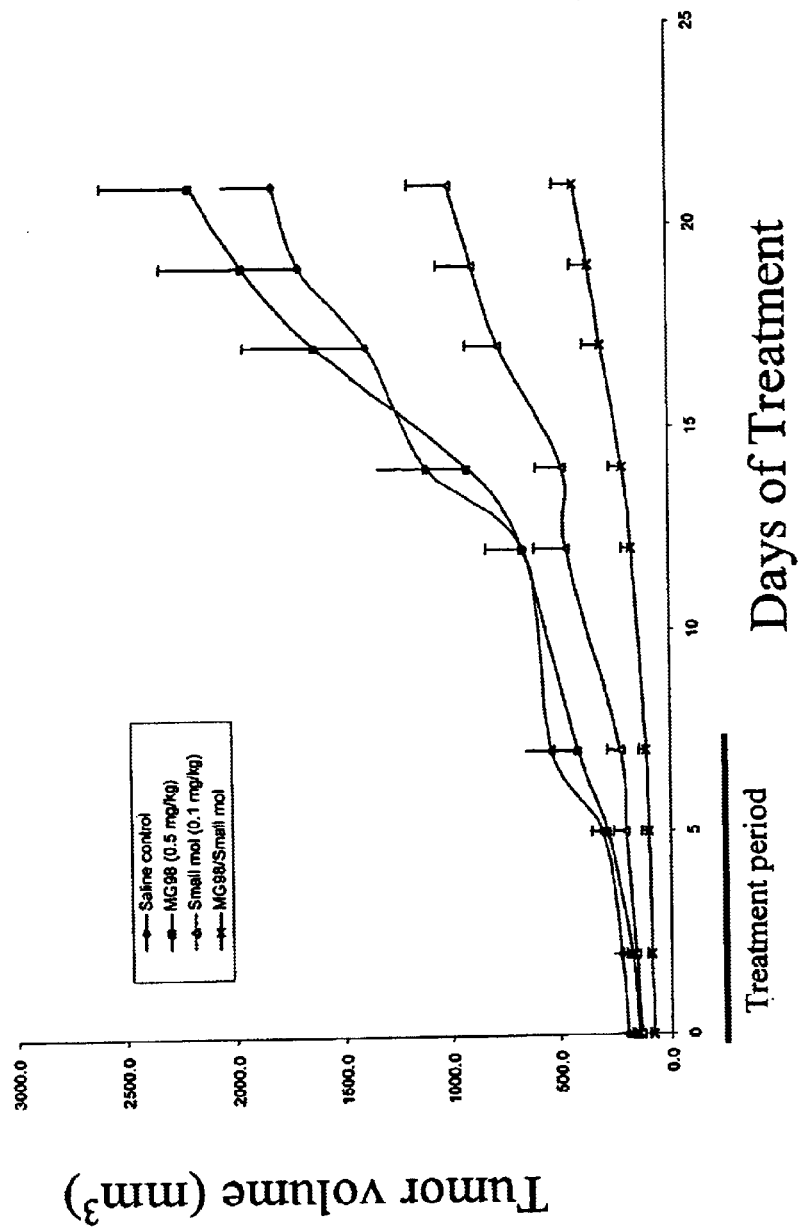
FIG. 19 is a graphic representation showing the ability of a representative, nonlimiting, synthetic oligonucleotide (MG98) (SEQ ID No:2) and of a representative, nonlimiting, DNA MeTase protein effector (5-aza-dC) according to the invention to inhibit Colo 205 human colon cancer cell growth (expressed as tumor volume over time) in a synergistic fashion resulting in an increased inhibitory effect as compared to that observed using either only the oligonucleotides or only the DNA MeTase protein effectors.
Figure 20A:
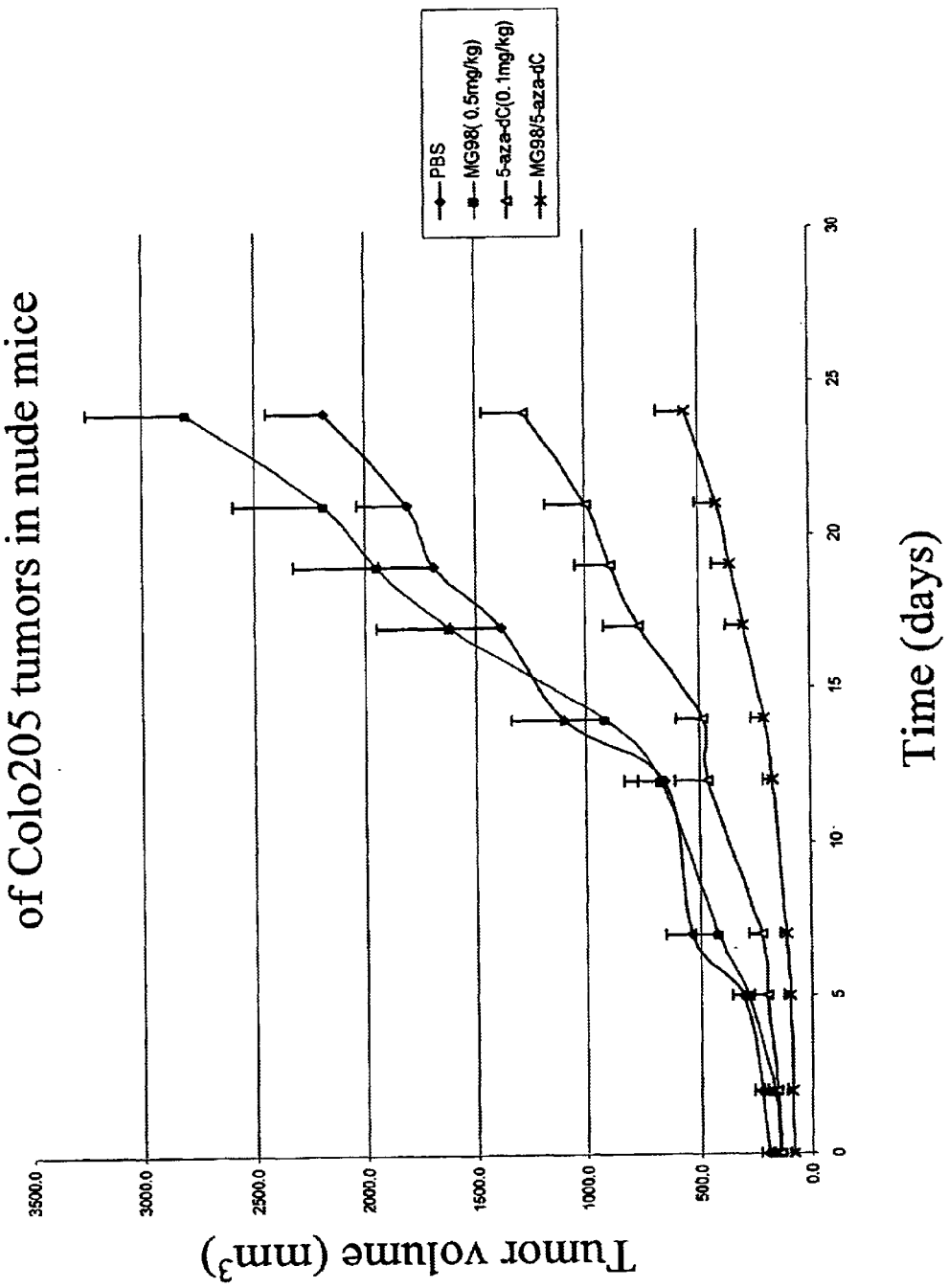
FIG. 20A is a graphic representation showing the inhibition of Colo 205 tumor cell growth in nude mice following treatment of the mice with saline (diamond); 0.5 mg/kg of a representative, nonlimiting MeTase synthetic oligonucleotide, MG98 (SEQ ID No:2) (square); 0.1 mg/kg of a representative, nonlimiting, DNA MeTase protein effector, 5-aza-dC (triangle); or a combination of both MG98 plus 5-aza-dC (X).

The purpose of this example is to illustrate the ability of the methods and compositions of the invention to treat diseases responsive to DNA MeTase inhibition in mammals. This example further provides evidence of the ability of the methods and compositions of the invention to inhibit tumor growth in a mammal. Eight to ten week old female BALB/c nude mice (Taconic Labs, Great Barrington, N.Y.) were injected subcutaneously in the flank area with $2 \times 10^6$ pre-conditioned Colo 205 human colon cancer cells (ATCC No. CCL-222). Preconditioning of these cells was done by a minimum of three consecutive tumor transplantations in the same strain of nude mice. Subsequently, tumor fragments of approximately 30 mgs were excised and implanted subcutaneously in mice, in the left flank area under Forene anesthesia (Abbott Labs., Geneva, Switzerland). When the tumors reached a mean volume of 100 mm$^3$, the mice were treated intravenously for 7 consecutive days by daily bolus infusion into the tail vein, with oligonucleotide saline preparations containing 0.1–6 mg/kg of antisense oligonucleotide and/or 5-aza-dC (Sigma, St. Louis, Mo.) also in saline preparations according to the present invention The optimal final concentration of the oligonucleotide is established by dose response experiments according to standard protocols. Tumor volume was calculated according to standard methods every second day post infusion (see methods, e.g., in Meyer et al. (1989) Int. J. Cancer 43: 851–856). Treatment with the oligonucleotides and protein effectors according to the methods of the invention caused a significant reduction in tumor weight and volume relative to controls treated with saline as shown in FIGS. 19, 20A, and 20B. FIG. 19 shows that animals receiving only saline (diamond) or 0.5 mg/kg MG98 (square) for seven days showed tumor volume increase while those animals receiving 0.1 mg/kg 5-aza-dC only (triangle) showed less tumor volume increase. The most dramatic reduction in tumor volume was seen in animals receiving both 0.5 mg/kg MG98 and 0.1 mg/kg 5-aza-dC (FIG. 19, X) for seven days.

FIGS. 20A and 20B show the results of a similar experiment, where tumor volume is recorded for 25 days (i.e., 19 additional days after final treatment. FIG. 1 20A shows a tumor volume growth curve versus time while FIG. 20B shows tumor volume in these mice on day 25. As shown in FIG. 20B, mice which had received both 0.5 mg/kg MG98 and 0.1 mg/kg 5-aza-dC had statistically smaller tumors (p<0.05) than mice treated with saline only or 5-aza-dC only. In addition, the activity of DNA MeTase enzyme when measured is expected to be significantly reduced relative to saline treated controls. These results show that the oligonucleotides and protein effectors according to the methods of the invention are capable of inhibiting tumor growth in a synergistic fashion.

Example 7

Different Synergistic Effects On Cell Cycle Progression Inhibition With Scheduling Differences The purpose of this example is to illustrate that the synergistic effect on inhibition of cell cycle progression by a antisense oligonucleotide of the invention combined with a protein effector of the invention can be accomplished by different scheduling routines. In this example, T24 cells were used.

In Schedule A, the cells were transfected for four hours on day 0 with 75 mM MG88. The next day, they were transfected again for four hours with 75 mM MG88. The following day, they were treated with 1 $\mu$M 5-aza-dC. After twenty-four hours, the media was replaced with fresh media containing 1 $\mu$M aza-dC. For controls, the cells received either no treatment, treatment with only aza-dC (where the cells were untouched for the first two days), or treatment with only MG88 (where the cells were untouched for the third and fourth days).

In schedule B, the cells were treated with 1 $\mu$M 5-aza-dC. After twenty-four hours, the media was replaced with fresh media containing 1 $\mu$M aza-dC. Twenty-four hours later, the cells were transfected for four hours with 75 mM MG88. The next day, they were transfected again for four hours with 75 mM MG88. For controls, the cells received either no treatment, treatment with only aza-dC (where the cells were untouched for the third and fourth days), or treatment with only MG88 (where the cells were untouched for the first and second days).

On the fifth day, the cells were harvested, and fixed and permeabilized in ice-cold 70% ethanol, and stained with propidium iodide according to standard techniques (see, e.g., Ausubel et al, supra; Sambrook et al., supra). The stained cells were next analyzed by fluorescence activated cell sorter analysis (FACS analysis). According to FACS analysis of cells stained with propidium iodide, cells can typically be divided into four groups depending on the amount of DNA they possess that is stained with the propidium iodide. Typically, 4N cells (i.e., $G_2$/M phase cells that are about to divide) are at the farthest right of a histogram. The next set of cells with the second to highest staining are cells in S phase. The third most bright set of cells is the 2N cells in the $G_1$ stage of cell cycle. Finally, the least bright cells (i.e., those cells at the far left of a FACS histogram), are those that are undergoing apoptotic cell death.

Figure 21:
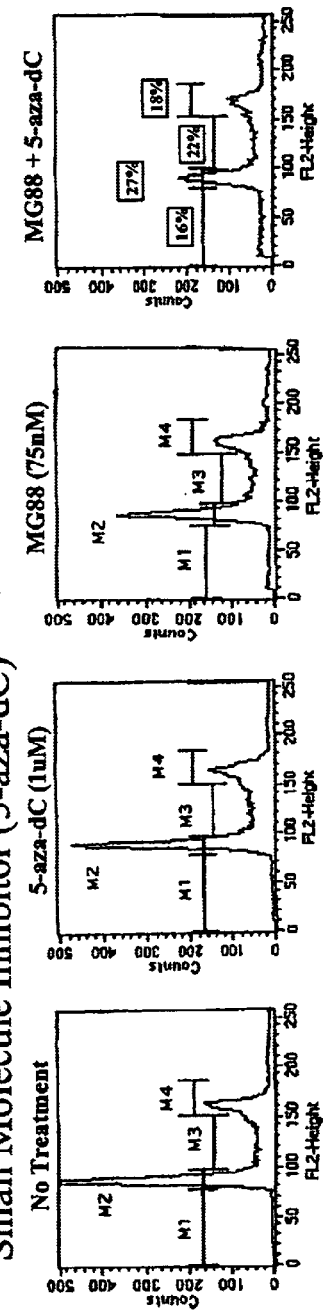
FIG. 21 is a schematic diagram showing a series of FACS histogram analyses of T24 cells treated with a representative, nonlimiting, synthetic oligonucleotide (MG88) (SEQ ID No:1) and/or representative non-limiting DNA MeTase protein effector (5aza-dC) according to the invention, at different schedules. The upper panel of histograms shows cells treated on schedule A, where MG88 is administered before 5-aza-dC. The lower panel of histograms shows cells treated on schedule B, where 5-aza-dC is administered before MG88.
Figure 21:
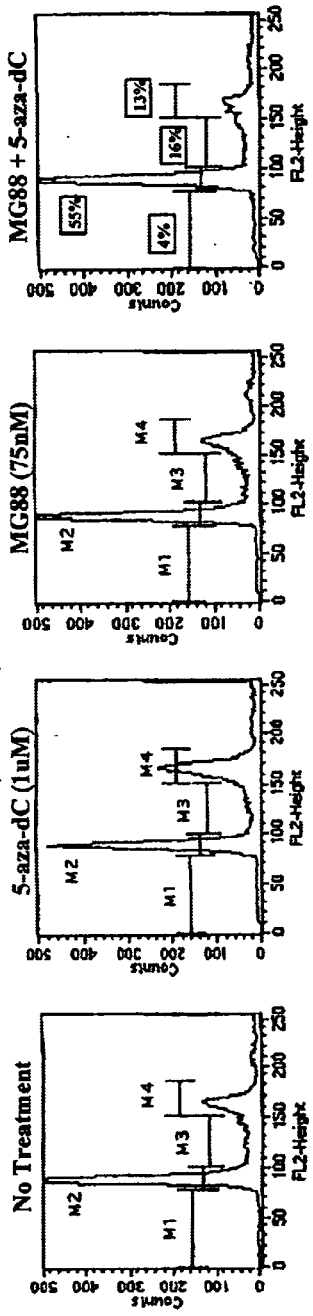

As shown on FIG. 21, cells receiving both MG88 and 5aza-dC in Schedule A (upper panel, far right) showed a decrease in the percentage of cells in the S phase of the cell cycle (27% in section M2) and increases in the percentage of apoptosing cells (16% in section M1) and cells in the S phase (22% in section M3). In contrast, cells receiving both MG88 and 5-aza-dC in Schedule B (FIG. 21, lower panel, far right) showed a more pronounced $G_1$ block (55% in section M2 in FIG. 21), and fewer 4N cells in the $G_2$/M population (13% in section M4). Notably, however, either Schedule A or Schedule B resulted in more inhibition of cell cycle progression when both MG88 and 5-aza-dC were received, as compared to cells receiving only MG88 or only 5-aza-dC (compare far right sections with middle sections in upper for Schedule A and lower panel for Schedule B).

Example 8

Synergistic Effect On Inhibition Of Thymidylate Synthase With a Combination of TS Antisense Oligonucleotide and TS Protein Effector The enzyme thymidylate synthase (TS) catalyzes a critical step in the synthesis of DNA and is especially crucial to neoplastic cells undergoing uncontrolled proliferation. The example illustrates the ability of a TS antisense oligonucleotide and a TS protein effector to act synergistically in cells to inhibit TS protein expression and inhibit the role of TS in cell cycle progression. The representative nonlimiting oligonucleotides of the invention used in this example were MG2605, which has the following sequence: 5' UUC ATA ACC TCA GCA TUG UC 3' (SEQ ID NO:71; this oligonucleotide is targeted to the thymidylate synthase mRNA sequence provided in GenBank Accession No. X02308 at nucleotides 1267–1286) and control oligonucleotide MG2606, which has the following sequence: 5' GUC UTA AGC TCA ACA TUC UA 3' (SEQ ID NO: 81). These oligonucleotides were chemically modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of each oligonucleotide consisted of a phosphorothioate linkage between adjoining nucleotides.

The representative nonlimiting TS protein effector used in this example is the nucleoside analog 5-fluorouracil (5-FU).

To look at the ability of MG2605 to inhibit TS protein expression, T24 cells growing in culture were treated with lipofectin only (6.25 $\mu$g/ml) or lipofectin plus 10 nM, 25 nM, or 50 nM of MG2605 or MG2606 for 72 hours (i.e., transfection for four hours per day for three consecutive days). After treatment, the cells were lysed and analyzed by Western blotting analysis for thymidylate synthase protein levels using a thymidylase synthase specific antibody (commercially available from Chemicon Int., Temecula, Calif.).

Figure 22:
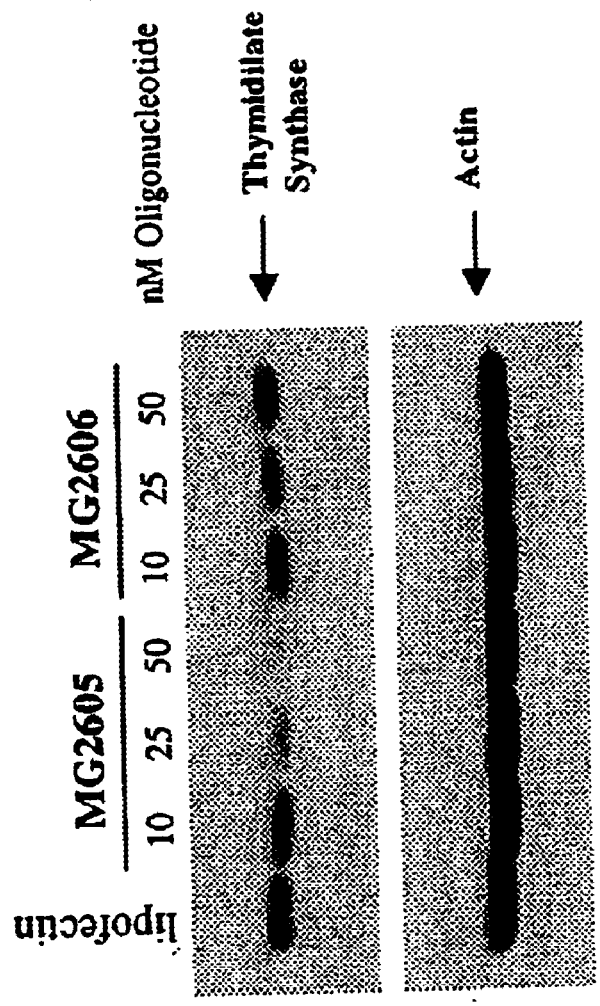
FIG. 22 is a representation of an autoradiograph of the Western blotting analysis showing the synergistic inhibition of thymidylate synthase protein expression in T24 cells using the combination of a representative, nonlimiting, synthetic antisense oligonucleotide (MG2605) (SEQ ID No:71) and a representative, nonlimiting TS protein effector (5-FU) according to the invention

As shown in FIG. 22, T24 cells transfected for 72 hours with 25 or 50 nM MG2605, but not control MG2606 showed diminished levels of thymidylate synthase protein as compared to cells treated with lipofectin only. Equal loading of all wells is demonstrated by equivalent amounts of actin (FIG. 22).

To look at the ability of MG2605 to inhibit the role of TS in cell cycle progression, T24 cells growing in culture were treated with lipofectin only (6.25 μg/ml) or lipofectin plus 25 nM of MG2605 or MG2606, or lipofectin plus 25 nM of MG2605 or MG2606 plus 500 nM 5-FU for 72 hours (i.e., transfection for four hours per day for three consecutive days, with each transfection followed by incubation with 500 nM of 5-FU). After treatment, the cells were processed for cell cycle analysis by FACS analysis as described in Example 7.

Figure 23:
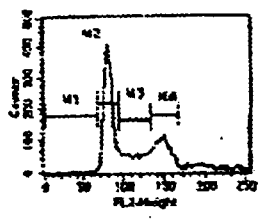
FIG. 23 is a schematic diagram showing a series of FACS histogram analyses of T24 cells treated with a representative, nonlimiting synthetic thymidylate synthase antisense oligonucleotide and/or a representative non-limiting TS protein effector (5-FU) according to the invention. The top histograms shows cells treated with lipofectin only; the second histogram shows cells treated with 25 nM mismatch control oligonucleotide; the third histogram from the top shows cells treated with 25 nM of the TS antisense oligonucleotide, MG2605 (SEQ ID No:71); the fourth histogram from the top shows cells treated with 500 nM of 5-FU; the fifth histogram from the top shows cells treated with 5-FU plus mismatch oligonucleotide; and the sixth histogram (i.e., the bottom histogram) shows cells treated with 5-FU plus the TS antisense oligonucleotide, MG2605.
Figure 23:
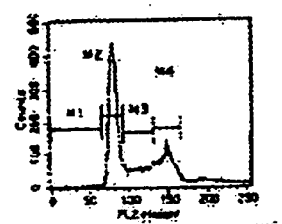
Figure 23:
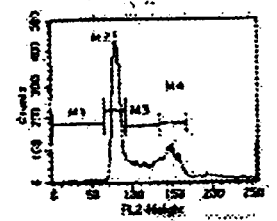
Figure 23:
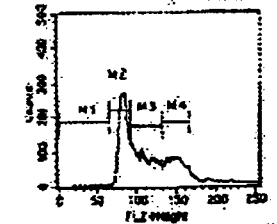
Figure 23:
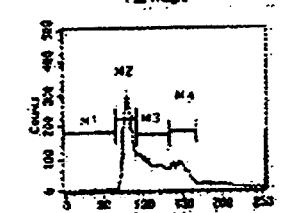
Figure 23:
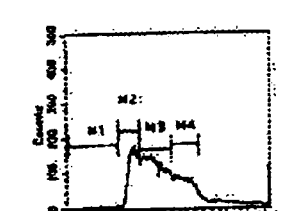

FIG. 23 shows that T24 cells treated with 500 nM 5-FU in combination with MG2605 showed a greater number of cells arrested in the S phase (section M3; bottom panel), as compared to cells treated with only MG2605 (3rd panel from top) or only 5-FU (4th panel from top).

In a similar experiment, T24 cells were transfected for four hours with 25 nM of TS antisense oligonucleotide MG2605 or control oligonucleotide MG2606 at 0 and 24 hours. After each four hour exposure to oligonucleotide, cells were returned to serum-containing media. Some of the cells were returned to serum-containing media to which was added 5 μM of 5-FU. At 72 hours, the cells were harvested, counted, and fixed and permeabilized in ice-cold 70% ethanol. The cells were then stained with propidium iodide and cell cycle analysis was performed by flow cytometry analysis as described in Example 7.

Figure 24A:
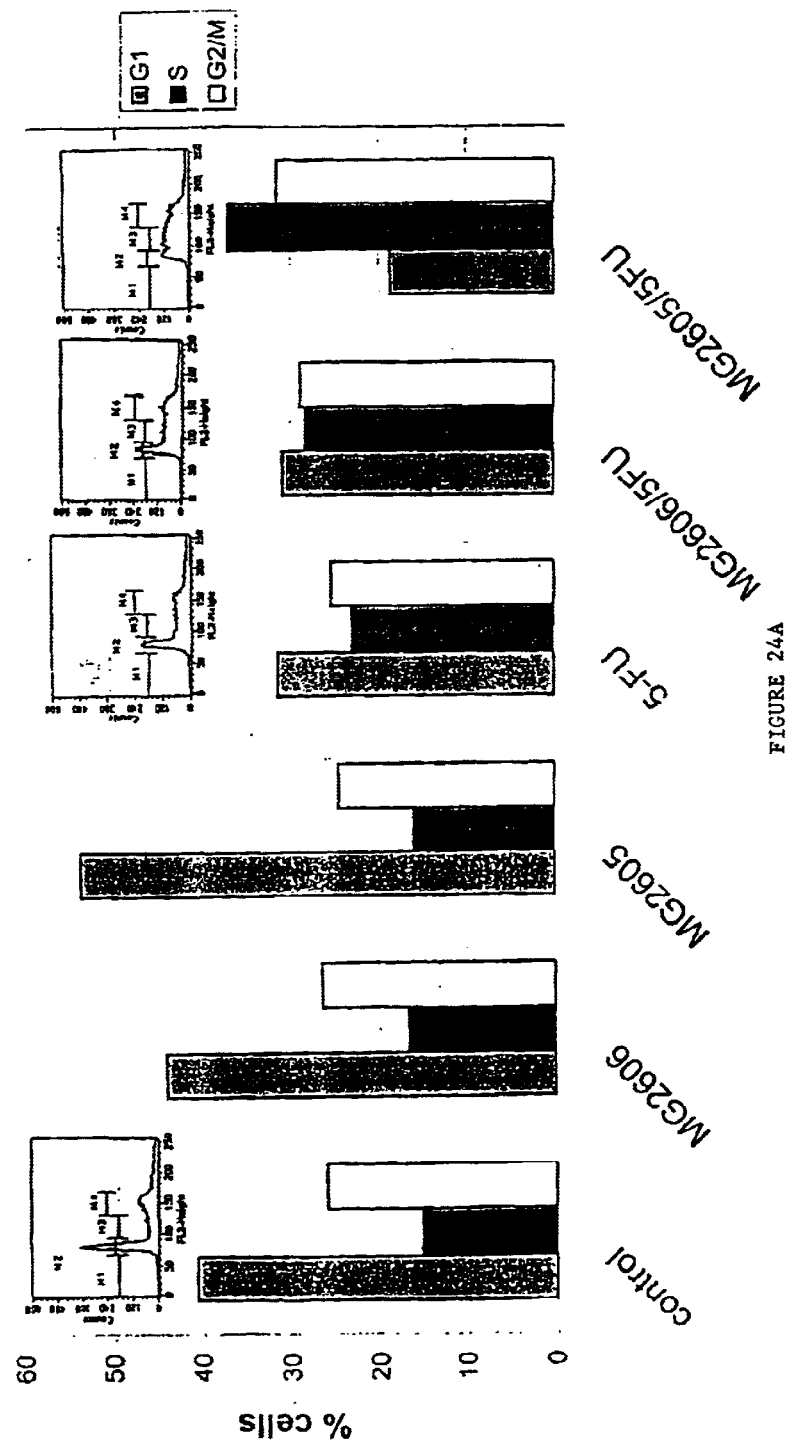
FIG. 24A is a graphic representation showing the percentages of T24 cells in the $G_1$ phase (gray bars; section M2 on inserted histograms) S phase (black bars; section M3 on inserted histograms), and $G_2/M$ phase (white bars; section M4 on inserted histogram) following treatment with 25 nM of a representative, nonlimiting TS antisense oligonucleotide MG2605 (SEQ ID No:71), 25 nM of control oligonucleotide MG2606 (SEQ ID No:81), 5 µM of a representative nonlimiting TS protein effector, 5-FU, or a combination of oligonucleotide plus 5-FU.
Figure 24B:
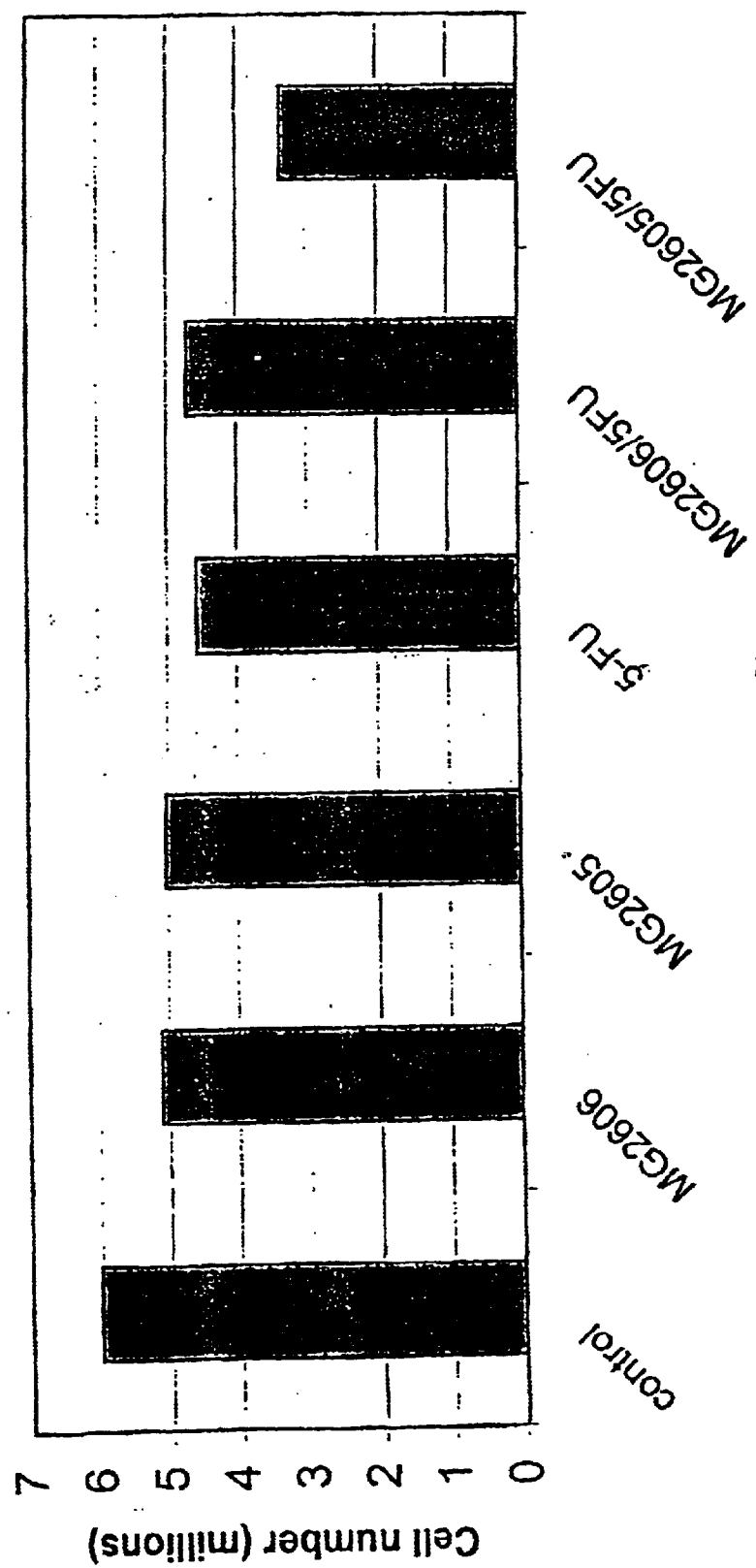
FIG. 24B is a graphic representation of the number of T24 cells remaining following treatment with following no treatment; or treatment with 25 nM of a representative, nonlimiting TS antisense oligonucleotide MG2605 (SEQ ID No:71); 25 nM of control oligonucleotide MG2606 (SEQ ID No:81); 5 µM of a representative nonlimiting TS protein effector, 5-FU; or a combination of MG2605 or MG2606 plus 5-FU.

FIG. 24A shows the percentage of cells in $G_1$ phase (section M1), S phase (section M2), and $G_2$/M phase (section M3) following treatment with nothing, MG2606 only, MG2605 only, 5-FU only, MG2606 plus 5-FU, or MG2605 plus 5-FU. Treatment with both MG2605 plus 5-FU resulted in a greater number of cells arrested in the S phase of the cell cycle and fewer cells in the $G_1$ phase of the cell cycle as compared to treatment with either MG2605 alone or 5-FU alone (FIG. 24A). Moreover, treatment with the combination of MG2605 plus 5-FU resulted in a lower number cells as compared to the number of cells present following treatment with 5-FU only or MG2605 only (FIG. 24B).

This example demonstrates that expression of thymidylate synthase, and its role in cell cycle progression, is inhibited in T24 cells by the combination of a TS antisense oligonucleotide plus a TS protein effector to a greater degree than that seen in T24 receiving either the TS antisense oligonucleotide or the TS protein effector alone.

Example 9

Synergistic Effect On Inhibition Of HDAC Activity With HDAC Antisense Oligonucleotide and HDAC Protein Effector Functional histone deacetylases (HDACs) have been implicated as a requirement in cell cycle progression in both normal and neoplastic cells. The example illustrates the ability of an HDAC antisense oligonucleotide and a HDAC protein effector to act synergistically in cells to inhibit HDAC protein expression and induce the cyclin-dependent kinase inhibitor (CDKI) family, p21$^{WAF1}$.

To do this, the following representative, nonlimiting antisense oligonucleotides targeting both HDAC-1 and HDAC-2 were used: 5'-CAG CAA ATT ATG GGT CAT GCG GAU UG-3' (SEQ ID NO: 82); 5'-CAG CAA GTT ATG GGT CAT GCG GAU UG-3' (SEQ ID NO: 55); 5'-CAG CAA ATT ATG AGT CAT GCG GAU UG-3' (SEQ ID NO: 47); and 5'-CAG CAA GTT ATG AGT CAT GCG G AU UG-3' (SEQ ID NO: 83). This HDAC-1,2 antisense oligonucleotide (MG2610) was really a 1:1:1:1 mixture of each oligonucleotide (i.e., 25% of each). The control oligonucleotide (MG2637) was likewise a 1:1:1:1 mixture of the following four different oligonucleotides: 5'-AAG GAA GTC ATG GAT GAT GCG CAU UG-3' (SEQ ID NO: 84) and 5'-AAG GAA ATC ATG AAT GAT GCG CAU UG-3' (SEQ ID NO: 85). 5'-AAG GAA GTC ATG AAT GAT GCG CAU UG-3' (SEQ ID NO: 86) and 5'-AAG GAA ATC ATG GAT GAT GCG CAU UG-3' (SEQ ID NO: 87). These oligonucleotides were chemically modified as follows: A equals 2'-deoxyriboadenosine; C equals 2'-deoxyribocytidine; G equals 2'-deoxyriboguanosine; T equals 2'-deoxyribothymidine; A equals riboadenosine; U equals uridine; C equals ribocytidine; and G equals riboguanosine. The underlined bases were 2'-methoxyribose substituted nucleotides. Non-underlined bases indicate deoxyribose nucleosides. The backbone of each oligonucleotide consisted of a phosphorothioate linkage between adjoining nucleotides.

Figure 25:
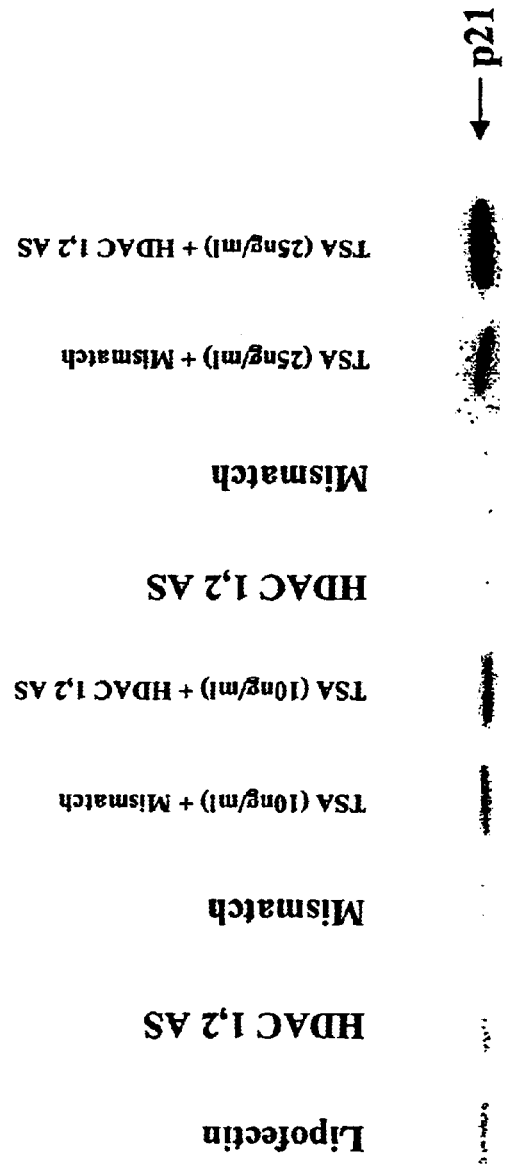
FIG. 25 is a representation of an autoradiograph of the Western blotting analysis showing the synergistic induction of $p21^{WAF1}$ by the combination of a representative, nonlimiting, synthetic HDAC antisense oligonucleotide and a representative, nonlimiting HDAC protein effector (TSA) according to the invention.

T24 cells were treated for 24 hours (i.e., 4 hours followed by incubation in fresh media for 20 hours) with lipofectin only, lipofectin plus 50 nM of MG2610 (i.e., HDAC-1,2 antisense oligonucleotide) or MG2637 control oligonucleotide, or lipofectin plus HDAC antisense oligonucleotide or control oligonucleotide plus 10 ng/ml or 25 ng/ml TSA. The treated cells were then lysed and cellular lysates analyzed by Western blotting analysis for p21$^{WAF1}$ protein level. As shown in FIG. 25, cells treated with the combination of HDAC-1,2 antisense oligonucleotide plus TSA showed a greater increase in p21$^{WAF1}$ protein level as compared to cells treated with either HDAC-1,2 antisense oligonucleotide or TSA alone.

This example demonstrates that treatment of cells with a combination of HDAC-1,2 antisense oligonucleotide plus an HDAC protein effector had a synergistic ability to enhance p21$^{WAF1}$ protein levels as compared to treatment of cells with either HDAC-1,2 antisense oligonucleotide alone or HDAC protein effector alone.

Example 10

Synergistic Anti-Neoplastic Effect of Histone Deacetylase Antisense Oligonucleotide and HDAC Protein Effector on Tumor Cells in Vivo The purpose of this example is to illustrate the ability of the histone deacetylase antisense oligonucleotide and the HDAC protein effector of the invention to inhibit tumor growth in a mammal. This example further provides evidence of the ability of the methods and compositions of the invention to inhibit tumor growth in domesticated mammal. Eight to ten week old female BALB/c nude mice (Taconic Labs, Great Barrington, N.Y.) are injected subcutaneously in the flank area with 2×10$^6$ preconditioned A549 human lung carcinoma cells. Preconditioning of these cells is done by a minimum of three consecutive tumor transplantations in the same strain of nude mice. Subsequently, tumor fragments of approximately 30 mgs are excised and implanted subcutaneously in mice, in the left flank area under Forene anesthesia (Abbott Labs., Geneva, Switzerland). When the tumors reaches a mean volume of 100 mm$^3$, one group of mice is treated daily with oligonucleotide saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC protein effector. Yet another group of mice receives both the antisense oligonucleotide and the HDAC protein effector.

Of this third group, group A receives the antisense oligonucleotide and the HDAC protein effector together simultaneously intravenously via the tail vein. Group B receives two infusions of the antisense oligonucleotide via the tail vein on Days 1 and 2, followed on Days 3 and 4 by two intravenous infusions of the HDAC protein effector. Group C receives two infusion of the HDAC protein effector followed by two infusions of the antisense oligonucleotide on Days 3 and 4.

Control groups of mice are similarly established which receive no treatment (e.g., saline only), a mismatch antisense oligonucleotide only, a control compound that does not inhibit histone deacetylase activity, and mismatch antisense oligonucleotide with control compound.

Tumor volume is measured with calipers. Treatment with the antisense oligonucleotide plus the HDAC protein effector according to the invention causes a significant reduction in tumor weight and volume relative to controls. Preferably, the antisense oligonucleotide and the HDAC protein effector inhibit the expression and activity of the same histone deacetylase.

What is claimed is:

1. A method for inhibiting the expression of human DNA methyltransferase-1 in a cell comprising contacting the cell with an effective synergistic amount of an antisense oligonucleotide and an effective synergistic amount of 5-aza-cytidine or 5-aza-2'-deoxycytidine, wherein the oligonucleotide is up to 35 nucleotides in length and comprises MG88.

2. A method for inhibiting the expression of human DNA methyltransferase-1 in a cell comprising contacting the cell with an effective synergistic amount of an antisense oligonucleotide and an effective synergistic amount of 5-aza-cytidine or 5-aza-2'-deoxycytidine, wherein the oligonucleotide is up to 35 nucleotides in length and comprises MG98.

3. A method for inhibiting tumor growth in a human comprising administering to a human, which has a tumor in its body, a therapeutically effective synergistic amount of an antisense oligonucleotide and a therapeutically effective synergistic amount of 5-aza-cytidine or 5-aza-2'-deoxycytidine, wherein the oligonucleotide is up to 35 nucleotides in length and comprises MG88.

4. A method for inhibiting tumor growth in a human comprising administering to a human, which has a tumor in its body, a therapeutically effective synergistic amount of an antisense oligonucleotide and a therapeutically effective synergistic amount of 5-aza-cytidine or 5-aza-2'-deoxycytidine, wherein the oligonucleotide is up to 35 nucleotides in length and comprises MG98.

* * * * *

SEQUENCE LISTING

```
<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
aagcatgagc accgttctcc                                              20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
ttcatgtcag ccaaggccac                                              20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
uuaatgtaac ctaaggucaa                                              20

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
aacgatcagg acccttgucc                                              20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gctgtctctt tccaaatctt                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
tttctgttaa gctgtctctt                                               20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
ttctccttca cacattcctt                                               20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cgtgcaagag attcaatttc                                               20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
aagtcacata actgattctt                                               20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
ctcggataat tcttctttac                                               20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
ccaggtagcc ctcctcggat                                               20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide
```

```
<400> SEQUENCE: 12
agggatttga ctttagccag                                                    20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
tccaaggaca aatctttatt                                                    20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
catgagcacc gttctccaag                                                    20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
acgtccattc acttcccggt                                                    20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
tcacttcttg cttgcttccc                                                    20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
gcttggttcc cgttttctag                                                    20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
ctagacgtcc attcacttcc                                                    20

<210> SEQ ID NO 19
```

```
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
actctacggg cttcacttct                                              20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
tctgccattc ccactctacg                                              20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
catctgccat tcccactcta                                              20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide

<400> SEQUENCE: 22
ggcatctgcc attcccactc                                              20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
atcggacttg ctcctcctgg                                              20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
ggtgacggga gggcagaact                                              20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
```
tgccagaaac agggtgacg    20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
gtgcatgttg gggattcctg    20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
gtgaacggac agattgacat    20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
aggccacaaa caccatgtac    20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
cgaacctcac acaacagctt    20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
gataagcgaa cctcacacaa    20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
ctgcacaatt tgatcactaa    20

<210> SEQ ID NO 32
<211> LENGTH: 20
<212> TYPE: DNA

```
<213> ORGANISM: Artificial Sequence
<220> FEATURE:
<223> OTHER INFORMATION: oligonucleotide

<400> SEQUENCE: 32
cagaaacagg ggtgacggga                                                    20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
gcacaaagta ctgcacaatt                                                    20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
tccagaatgc acaaagtact                                                    20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
gagacagcag caccagcggg                                                    20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
atgaccgagt gggagacagc                                                    20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide

<400> SEQUENCE: 37
ggatgaccga gtgggagaca                                                    20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide

<400> SEQUENCE: 38
caggatgacc gagtgggaga                                                    20
```

<210> SEQ ID NO 39
<211> LENGTH: 20
<212> TYPE: DNA
<213> ORGANISM: Artificial Sequence
<220> FEATURE:
<223> OTHER INFORMATION: oligonucleotide

<400> SEQUENCE: 39
tgtgttctca ggatgaccga                                          20

<210> SEQ ID NO 40
<211> LENGTH: 20
<212> TYPE: DNA
<213> ORGANISM: Artificial Sequence
<220> FEATURE:
<223> OTHER INFORMATION: oligonucleotide

<400> SEQUENCE: 40
gagtgacaga gacgctcagg                                          20

<210> SEQ ID NO 41
<211> LENGTH: 20
<212> TYPE: DNA
<213> ORGANISM: Artificial Sequence
<220> FEATURE:
<223> OTHER INFORMATION: oligonucleotide

<400> SEQUENCE: 41
ttctggcttc tcctccttgg                                          20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide

<400> SEQUENCE: 42
cttgacctcc tccttgaccc                                          20

<210> SEQ ID NO 43
<211> LENGTH: 20
<212> TYPE: DNA
<213> ORGANISM: Artificial Sequence
<220> FEATURE:
<223> OTHER INFORMATION: oligonucleotide

<400> SEQUENCE: 43
ggaagccaga gctggagagg                                          20

<210> SEQ ID NO 44
<211> LENGTH: 20
<212> TYPE: DNA
<213> ORGANISM: Artificial Sequence
<220> FEATURE:
<223> OTHER INFORMATION: oligonucleotide

<400> SEQUENCE: 44
gaaacgtgag ggactcagca                                          20

<210> SEQ ID NO 45
<211> LENGTH: 23
<212> TYPE: DNA
<213> ORGANISM: Artificial Sequence
<220> FEATURE:

```
<223> OTHER INFORMATION: oligonucleotide

<400> SEQUENCE: 45
ccgtcgtagt agtaacagac ttt                                              23

<210> SEQ ID NO 46
<211> LENGTH: 22
<212> TYPE: DNA
<213> ORGANISM: Artificial Sequence
<220> FEATURE:
<223> OTHER INFORMATION: oligonucleotide

<400> SEQUENCE: 46
tgtccataat agtaatttcc aa                                               22

<210> SEQ ID NO 47
<211> LENGTH: 26
<212> TYPE: DNA
<213> ORGANISM: Artificial Sequence
<220> FEATURE:
<223> OTHER INFORMATION: oligonucleotide

<400> SEQUENCE: 47
cagcaaatta tgagtcatgc ggattc                                           26

<210> SEQ ID NO 48
<211> LENGTH: 20
<212> TYPE: DNA
<213> ORGANISM: Artificial Sequence
<220> FEATURE:
<223> OTHER INFORMATION: oligonucleotide

<400> SEQUENCE: 48
aagcatgagc accgttcucc                                                  20

<210> SEQ ID NO 49
<211> LENGTH: 20
<212> TYPE: DNA
<213> ORGANISM: Artificial Sequence
<220> FEATURE:
<223> OTHER INFORMATION: oligonucleotide

<400> SEQUENCE: 49
uucatgtcag ccaaggccac                                                  20

<210> SEQ ID NO 50
<211> LENGTH: 20
<212> TYPE: DNA
<213> ORGANISM: Artificial Sequence
<220> FEATURE:
<223> OTHER INFORMATION: oligonucleotide

<400> SEQUENCE: 50
ctccttgact gtacgccatg                                                  20

<210> SEQ ID NO 51
<211> LENGTH: 20
<212> TYPE: DNA
<213> ORGANISM: Artificial Sequence
<220> FEATURE:
<223> OTHER INFORMATION: oligonucleotide

<400> SEQUENCE: 51
tgctgctgct gctgctgccg                                                  20
```

```
<210> SEQ ID NO 52
<211> LENGTH: 20
<212> TYPE: DNA
<213> ORGANISM: Artificial Sequence
<220> FEATURE:
<223> OTHER INFORMATION: oligonucleotide

<400> SEQUENCE: 52
cctcctgctg ctgctgctgc                                                 20

<210> SEQ ID NO 53
<211> LENGTH: 23
<212> TYPE: DNA
<213> ORGANISM: Artificial Sequence
<220> FEATURE:
<223> OTHER INFORMATION: oligonucleotide

<400> SEQUENCE: 53
ccgtcgtagt agtagcagac ttt                                             23

<210> SEQ ID NO 54
<211> LENGTH: 22
<212> TYPE: DNA
<213> ORGANISM: Artificial Sequence
<220> FEATURE:
<223> OTHER INFORMATION: oligonucleotide

<400> SEQUENCE: 54
tgtccataat aataatttcc aa                                              22

<210> SEQ ID NO 55
<211> LENGTH: 26
<212> TYPE: DNA
<213> ORGANISM: Artificial Sequence
<220> FEATURE:
<223> OTHER INFORMATION: oligonucleotide

<400> SEQUENCE: 55
cagcaagtta tgggtcatgc ggattc                                          26

<210> SEQ ID NO 56
<211> LENGTH: 20
<212> TYPE: DNA
<213> ORGANISM: Artificial Sequence
<220> FEATURE:
<223> OTHER INFORMATION: oligonucleotide

<400> SEQUENCE: 56
ggttcctttg gtatctgttt                                                 20

<210> SEQ ID NO 57
<211> LENGTH: 20
<212> TYPE: DNA
<213> ORGANISM: Artificial Sequence
<220> FEATURE:
<223> OTHER INFORMATION: oligonucleotide

<400> SEQUENCE: 57
ggaggcaggc caagtggtcc                                                 20

<210> SEQ ID NO 58
<211> LENGTH: 20
<212> TYPE: DNA
<213> ORGANISM: Artificial Sequence
<220> FEATURE:
<223> OTHER INFORMATION: oligonucleotide
```

```
<400> SEQUENCE: 58
cggaggcagg ccaagtggtc                                               20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide

<400> SEQUENCE: 59
gacggaggca ggccaagtgg                                               20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide

<400> SEQUENCE: 60
acggaggcag gcgaagtggc                                               20

<210> SEQ ID NO 61
<211> LENGTH: 20
<212> TYPE: DNA
<213> ORGANISM: Artificial Sequence
<220> FEATURE:
<223> OTHER INFORMATION: oligonucleotide

<400> SEQUENCE: 61
ggacggaggc aggcgaagtg                                               20

<210> SEQ ID NO 62
<211> LENGTH: 20
<212> TYPE: DNA
<213> ORGANISM: Artificial Sequence
<220> FEATURE:
<223> OTHER INFORMATION: oligonucleotide

<400> SEQUENCE: 62 aagcaccta aacagccatt                                                20

<210> SEQ ID NO 63
<211> LENGTH: 20
<212> TYPE: DNA
<213> ORGANISM: Artificial Sequence
<220> FEATURE:
<223> OTHER INFORMATION: oligonucleotide

<400> SEQUENCE: 63
ttgaaagcac cctaaacagc                                               20

<210> SEQ ID NO 64
<211> LENGTH: 20
<212> TYPE: DNA
<213> ORGANISM: Artificial Sequence
<220> FEATURE:
<223> OTHER INFORMATION: oligonucleotide

<400> SEQUENCE: 64
acaatatcct tcaagctcct                                               20

<210> SEQ ID NO 65
<211> LENGTH: 20
```

```
<212> TYPE: DNA
<213> ORGANISM: Artificial Sequence
<220> FEATURE:
<223> OTHER INFORMATION: oligonucleotide

<400> SEQUENCE: 65
cctaaagact gacaatatcc                                              20

<210> SEQ ID NO 66
<211> LENGTH: 20
<212> TYPE: DNA
<213> ORGANISM: Artificial Sequence
<220> FEATURE:
<223> OTHER INFORMATION: oligonucleotide

<400> SEQUENCE: 66
aattaataac tgataggtca                                              20

<210> SEQ ID NO 67
<211> LENGTH: 20
<212> TYPE: DNA
<213> ORGANISM: Artificial Sequence
<220> FEATURE:
<223> OTHER INFORMATION: oligonucleotide

<400> SEQUENCE: 67
ccagtggcaa catccttaaa                                              20

<210> SEQ ID NO 68
<211> LENGTH: 20
<212> TYPE: DNA
<213> ORGANISM: Artificial Sequence
<220> FEATURE:
<223> OTHER INFORMATION: oligonucleotide

<400> SEQUENCE: 68
cacagttaca tttgccagtg                                              20

<210> SEQ ID NO 69
<211> LENGTH: 20
<212> TYPE: DNA
<213> ORGANISM: Artificial Sequence
<220> FEATURE:
<223> OTHER INFORMATION: oligonucleotide

<400> SEQUENCE: 69
ttatggaaag aactggcaca                                              20

<210> SEQ ID NO 70
<211> LENGTH: 20
<212> TYPE: DNA
<213> ORGANISM: Artificial Sequence
<220> FEATURE:
<223> OTHER INFORMATION: oligonucleotide

<400> SEQUENCE: 70
cctcagcatt gtcagatacc                                              20

<210> SEQ ID NO 71
<211> LENGTH: 20
<212> TYPE: DNA
<213> ORGANISM: Artificial Sequence
<220> FEATURE:
<223> OTHER INFORMATION: oligonucleotide

<400> SEQUENCE: 71
```

|  |  |
|---|---|
| ttcataacct cagcattgtc | 20 |

<210> SEQ ID NO 72
<211> LENGTH: 20
<212> TYPE: DNA
<213> ORGANISM: Artificial Sequence
<220> FEATURE:
<223> OTHER INFORMATION: oligonucleotide

<400> SEQUENCE: 72

|  |  |
|---|---|
| acatttcatt ctcctcactt | 20 |

<210> SEQ ID NO 73
<211> LENGTH: 20
<212> TYPE: DNA
<213> ORGANISM: Artificial Sequence
<220> FEATURE:
<223> OTHER INFORMATION: oligonucleotide

<400> SEQUENCE: 73

|  |  |
|---|---|
| catacatttc attctcctca | 20 |

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74

|  |  |
|---|---|
| ccaaccttct ttataagtac | 20 |

<210> SEQ ID NO 75
<211> LENGTH: 20
<212> TYPE: DNA
<213> ORGANISM: Artificial Sequence
<220> FEATURE:
<223> OTHER INFORMATION: oligonucleotide

<400> SEQUENCE: 75

|  |  |
|---|---|
| aattcaccaa ccttctttat | 20 |

<210> SEQ ID NO 76
<211> LENGTH: 20
<212> TYPE: DNA
<213> ORGANISM: Artificial Sequence
<220> FEATURE:
<223> OTHER INFORMATION: oligonucleotide

<400> SEQUENCE: 76

|  |  |
|---|---|
| ttgagggaat agcttgtgaa | 20 |

<210> SEQ ID NO 77
<211> LENGTH: 20
<212> TYPE: DNA
<213> ORGANISM: Artificial Sequence
<220> FEATURE:
<223> OTHER INFORMATION: oligonucleotide

<400> SEQUENCE: 77

|  |  |
|---|---|
| ttactcagct ccctcagatt | 20 |

<210> SEQ ID NO 78
<211> LENGTH: 20
<212> TYPE: DNA
<213> ORGANISM: Artificial Sequence

```
<220> FEATURE:
<223> OTHER INFORMATION: oligonucleotide

<400> SEQUENCE: 78
aacacttctt tattatagca                                              20

<210> SEQ ID NO 79
<211> LENGTH: 23
<212> TYPE: DNA
<213> ORGANISM: Artificial Sequence
<220> FEATURE:
<223> OTHER INFORMATION: oligonucleotide

<400> SEQUENCE: 79
gtaggtgggg aggagtttag ttt                                          23

<210> SEQ ID NO 80
<211> LENGTH: 23
<212> TYPE: DNA
<213> ORGANISM: Artificial Sequence
<220> FEATURE:
<223> OTHER INFORMATION: oligonucleotide

<400> SEQUENCE: 80
tctaataacc aaccaacccc taa                                          23

<210> SEQ ID NO 81
<211> LENGTH: 20
<212> TYPE: DNA
<213> ORGANISM: Artificial Sequence
<220> FEATURE:
<223> OTHER INFORMATION: oligonucleotide

<400> SEQUENCE: 81
gucutaagct caacatucua                                              20

<210> SEQ ID NO 82
<211> LENGTH: 26
<212> TYPE: DNA
<213> ORGANISM: Artificial Sequence
<220> FEATURE:
<223> OTHER INFORMATION: oligonucleotide

<400> SEQUENCE: 82
cagcaaatta tgggtcatgc ggauug                                       26

<210> SEQ ID NO 83
<211> LENGTH: 26
<212> TYPE: DNA
<213> ORGANISM: Artificial Sequence
<220> FEATURE:
<223> OTHER INFORMATION: oligonucleotide

<400> SEQUENCE: 83
cagcaagtta tgagtcatgc ggauug                                       26

<210> SEQ ID NO 84
<211> LENGTH: 26
<212> TYPE: DNA
<213> ORGANISM: Artificial Sequence
<220> FEATURE:
<223> OTHER INFORMATION: oligonucleotide

<400> SEQUENCE: 84
aaggaagtca tggatgatgc gcauug                                       26
```

```
<210> SEQ ID NO 85
<211> LENGTH: 26
<212> TYPE: DNA
<213> ORGANISM: Artificial Sequence
<220> FEATURE:
<223> OTHER INFORMATION: oligonucleotide

<400> SEQUENCE: 85
aaggaaatca tgaatgatgc gcauug                                          26

<210> SEQ ID NO 86
<211> LENGTH: 26
<212> TYPE: DNA
<213> ORGANISM: Artificial Sequence
<220> FEATURE:
<223> OTHER INFORMATION: oligonucleotide

<400> SEQUENCE: 86
aaggaagtca tgaatgatgc gcauug                                          26

<210> SEQ ID NO 87
<211> LENGTH: 26
<212> TYPE: DNA
<213> ORGANISM: Artificial Sequence
<220> FEATURE:
<223> OTHER INFORMATION: oligonucleotide

<400> SEQUENCE: 87
aaggaaatca tggatgatgc gcauug                                          26

<210> SEQ ID NO 88
<211> LENGTH: 20
<212> TYPE: DNA
<213> ORGANISM: Artificial Sequence
<220> FEATURE:
<223> OTHER INFORMATION: oligonucleotide

<400> SEQUENCE: 88
uucataacct cagcatuguc                                                 20

<210> SEQ ID NO 89
<211> LENGTH: 26
<212> TYPE: DNA
<213> ORGANISM: Artificial Sequence
<220> FEATURE:
<223> OTHER INFORMATION: oligonucleotide

<400> SEQUENCE: 89
cagcaagtta tgggtcatgc ggauug                                          26

<210> SEQ ID NO 90
<211> LENGTH: 26
<212> TYPE: DNA
<213> ORGANISM: Artificial Sequence
<220> FEATURE:
<223> OTHER INFORMATION: oligonucleotide

<400> SEQUENCE: 90
cagcaaatta tgagtcatgc ggauug                                          26
```